United States Patent
Dinnell et al.

(10) Patent No.: US 8,796,283 B2
(45) Date of Patent: Aug. 5, 2014

(54) INDOLE AND AZAINDOLE MODULATORS OF THE ALPHA 7 NACHR

(75) Inventors: Kevin Dinnell, Harlow (GB); Andrew Lightfoot, Harlow (GB); Gillian Elizabeth Lunniss, Harlow (GB)

(73) Assignee: Proximagen Limited, London (GB)

( * ) Notice: Subject to any disclaimer, the term of this patent is extended or adjusted under 35 U.S.C. 154(b) by 45 days.

(21) Appl. No.: 13/501,418

(22) PCT Filed: Oct. 14, 2010

(86) PCT No.: PCT/EP2010/065368
§ 371 (c)(1),
(2), (4) Date: May 15, 2012

(87) PCT Pub. No.: WO2011/045353
PCT Pub. Date: Apr. 21, 2011

(65) Prior Publication Data
US 2012/0283273 A1   Nov. 8, 2012

Related U.S. Application Data

(60) Provisional application No. 61/252,307, filed on Oct. 16, 2009.

(30) Foreign Application Priority Data

Jul. 28, 2010 (GB) .................................... 1012686.0

(51) Int. Cl.
A01N 43/54 (2006.01)
C07D 239/42 (2006.01)
C07D 401/04 (2006.01)

(52) U.S. Cl.
USPC ........................................ 514/256; 544/326

(58) Field of Classification Search
USPC ........................................ 544/326; 514/256
See application file for complete search history.

(56) References Cited

U.S. PATENT DOCUMENTS

| 7,816,353 | B2 * | 10/2010 | Cheng et al. | 514/235.8 |
| 8,377,941 | B2 * | 2/2013 | Dinnell et al. | 514/256 |
| 2011/0028486 | A1 * | 2/2011 | Dinnell et al. | 514/252.06 |
| 2012/0136009 | A1 * | 5/2012 | Dinnell | 514/256 |

FOREIGN PATENT DOCUMENTS

EP   0530149   3/1993

OTHER PUBLICATIONS

I.D. Glick et al., 35 Journal of Psychiatric Research, 187-191, 187 (2001).*
Y. Agid et al., 6 Nature Reviews | Drug Discovery 189-201, 189 (2007).*
R.S. Hurst, 25 The Journal of Neuroscience, 4396-4405 (2005).*
L.F. Martin et al., 174 Psychopharmacology 54-64 (2004).*
P.F. Buckley, 50 Biological Psychiatry, 912-924 (2001).*
I. Collins, Current Signal Transduction Therapy, 1, 13-23, 13 (2006).*
Chen et al., "Elaboration of 2-(Trifluoromethyl)indoles via a cascade coupling/condensation/deacylation process", Organic Letters, 2008, 10(4):625-628.
International Search Report for PCT/EP2010/065368 dated Nov. 22, 2010.

* cited by examiner

*Primary Examiner* — Deepak Rao
*Assistant Examiner* — Alexander R Pagano
(74) *Attorney, Agent, or Firm* — Andrus Intellectual Property Law, LLP

(57) ABSTRACT

This invention relates to modulation of the α7 nicotinic acetylcholine receptor (nAChR) by a compound of formula (I):

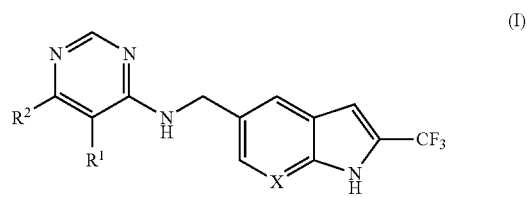

(I)

or a pharmaceutically acceptable salt thereof.

11 Claims, No Drawings

INDOLE AND AZAINDOLE MODULATORS OF THE ALPHA 7 NACHR

CROSS REFERENCE TO RELATED APPLICATION

The present application is the U.S. national stage application of International Application PCT/EP2010/065368, filed Oct. 14, 2010, which international application was published on Apr. 21, 2011, as International Publication WO2011/045353. The International Application claims priority of British Patent Application 1012686.3, filed Jul. 28, 2010, and U.S. Provisional Patent Application No. 61/252,307, filed Oct. 16, 2009, the contents of which are incorporated herein by reference in their entireties.

FIELD OF THE INVENTION

This invention relates to novel indole and azaindole derivatives having activity in modulation of the α7 nicotinic acetylcholine receptor (nAChR). The invention also relates to the use of the derivatives in treating diseases and conditions mediated by modulation of the α7 nAChR. In addition, the invention relates to compositions containing the derivatives and processes for their preparation.

BACKGROUND OF THE INVENTION

The neurotransmitter acetylcholine (ACh), by binding to cholinergic receptors causes the opening of ion channels within the mammalian system. The central nervous system (CNS) contains two types of ACh receptor, muscarinic receptors and nAChRs. nAChRs are ligand-gated ion channels containing five subunits (for reviews, see Colquhon et al. (1997) Advances in Pharmacology 39, 191-220; Williams et al. (1994) Drug News & Perspectives 7, 205-223; Doherty et al. (1995) Annual reports in Medicinal Chemistry 30, 41-50). The nAChR gene family can be divided into two groups: those coding for β subunits and those coding for α subunits (for reviews, see Karlin & Akabas (1995) Neuron 15, 1231-1244; Sargent (1993) Annu. Rev. Neurosci. 16, 403-443). Three of the α subunits, α7, α8 and α9, can form functional receptors when expressed alone and form homooligomeric receptors.

Studies have indicated that neuronal nicotinic receptors play important roles in modulating neurotransmission, cognition, sensory gating, and anxiety (Zarei et al. Neuroscience 1999, 88, 755-764, Frazier et al. J. Neurosci. 1998, 18, 8228-8235, Radcliffe et al. J. Neurosci. 1998, 18, 7075-7083, Minana et al. Neuropharmacology 1998, 37, 847-857, Albuquerque et al. Toxicol. Lett. 1998, 102-103, 211-218, Neubauer, et al. Neurology 1998, 51, 1608-1612, Stevens et al. Psychopharmacology 1998, 136, 320-327, Adler et al. Schizophrenia Bull. 1998, 24, 189-202.); thus, there has been interest in the use of compounds that modulate these receptors for treating CNS diseases.

A role for α7 receptors in the etiology of schizophrenia has been suggested by linkage studies (Freedman et al, Psychopharmacology (2004), 174(1), 54-64) demonstrating an association between the α7 locus and a sensory gating deficit which represents a major schizophrenia endophenotype. Such gating deficits in patients have been transiently reversed by nicotine with a pharmacology consistent with action via α7. In addition in animal models, lesion of forebrain cholinergic afferents or pharmacological blockade of α7 receptors elicits similar sensory gating deficits which are also apparent in in-bred mouse strains expressing reduced levels of the α7 receptor. Nicotine has been reported to normalise the deficits in both lesioned animals and in-bred mouse strains, again with a pharmacology compatible with activity at the α7 receptor. Pharmacological blockade of α7 receptors has been reported to impair rodent short-term working memory, whilst receptor activation has been reported to enhance performance in the same paradigm, thus implicating α7 receptors as a target for cognitive enhancement.

α7 nAChRs are characterised by their fast activation kinetics and high permeability to $Ca^{2+}$ compared to other subtypes (Delbono et al. J. Pharmacol. Exp. Ther. 1997, 280, 428-438.) and exhibit rapid desensitization following exposure to agonists. (Castro et al., Neurosci. Lett. 1993, 164, 137-140, Couturier et al., Neuron 1990, 5, 847-856, Alkondon et al., J. Pharmacol. Exp. Ther. 1994, 271, 494-506). Treatment with α7 agonists may therefore be problematic because both acetylcholine and nicotine both show activation followed by blockade and/or desensitisation of the receptor and hence chronic treatment with an agonist may well result in apparent antagonism. In addition, agonists have been shown to exhibit highest affinity for the desensitised state of the receptor and can, thus, mediate receptor desensitisation at concentrations below the threshold for receptor activation (Briggs and McKenna. Neuropharmacology 1998 37,1095-1102).

This problem may be overcome by treatment with a positive allosteric modulator (PAM). PAMs enhance α7 nAChR activation mediated by endogenous or exogenous agonists without activating the receptor in their own right, i.e. in the absence of agonist. A number of PAMs have been reported (Lightfoot et al. Progress in medicinal chemistry 46:131-71, 2008).

SUMMARY OF THE INVENTION

This invention relates to novel indole and azaindole derivatives having activity in modulation of the α7 nicotinic acetylcholine receptor (nAChR). The invention also relates to the use of the derivatives in treating diseases and conditions mediated by modulation of the α7 nAChR. In addition, the invention relates to compositions containing the derivatives and processes for their preparation.

DETAILED DESCRIPTION OF THE INVENTION

In general, This invention relates to novel indole and azaindole derivatives having activity in modulation of the α7 nicotinic acetylcholine receptor (nAChR). The invention also relates to the use of the derivatives in treating diseases and conditions mediated by modulation of the α7 nAChR. In addition, the invention relates to compositions containing the derivatives and processes for their preparation.

According to a first aspect, the invention provides a compound of formula (I) or a salt thereof:

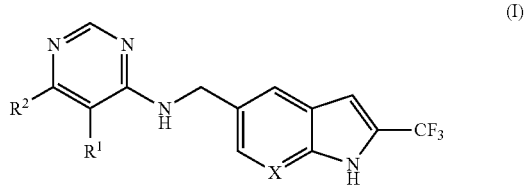

(I)

wherein
  $R^1$ is independently selected from the group consisting of H, $C_{1-6}$alkyl, halo$C_{1-6}$alkyl and halo;

$R^2$ is independently selected from the group consisting of $C_{1-6}$alkyl, halo$C_{1-6}$alkyl, halo, acetyl, cyano, $CH_2CN$ and cyclopropyl; and X is CH or N.

As used herein, a $C_{1-6}$alkyl substituent is a univalent radical derived by removal of a hydrogen atom from an acyclic $C_{1-6}$alkane. Such $C_{1-6}$alkyl substituents include methyl and ethyl, may be straight chain (i.e. n-propyl, n-butyl, n-pentyl and n-hexyl) or branched chain (for example, isopropyl, isobutyl, secbutyl, tert-butyl, isopentyl and neopentyl).

As used herein, a halo substituent refers to fluoro, chloro, bromo and iodo radicals. In an embodiment, unless otherwise indicated, any halo substituent is fluoro, chloro or bromo, for example, chloro or bromo.

As used herein, a halo$C_{1-6}$alkyl substituent is a $C_{1-6}$alkyl group substituted by one or more halo substituents, which halo substituents may be the same or different. Such $C_{1-6}$haloalkyl substituents include monofluoromethyl, difluoromethyl, trifluoromethyl and 1-chloro-2-fluoroethyl. In one embodiment, halo$C_{1-6}$alkyl is fluoro$C_{1-6}$alkyl, such as fluoro $C_{1-3}$alkyl. Examples of fluoro$C_{1-3}$alkyl include monofluoromethyl, difluoromethyl, trifluoromethyl, 1-fluoroethyl, 1,1-difluoroethyl and 1-fluoro-1-methylethyl.

In an embodiment, $R^1$ is H, F or methyl, for example, H.

In an embodiment, $R^2$ is independently selected from the group consisting of $C_{2-6}$alkyl, halo$C_{1-6}$alkyl, halo, acetyl, cyano, $CH_2CN$ and cyclopropyl. In a further embodiment, $R^2$ is independently selected from the group consisting of $C_{2-3}$alkyl, fluoro$C_{1-3}$alkyl, chloro, acetyl, cyano, $CH_2CN$ and cyclopropyl.

In a further embodiment, $R^2$ is halo$C_{1-6}$alkyl. In a further embodiment, $R^2$ is fluoro$C_{1-6}$alkyl. In a yet further embodiment, $R^2$ is fluoro$C_{1-3}$alkyl.

In one embodiment, $R^2$ is independently selected from the group consisting of ethyl, n-propyl, n-butyl, n-pentyl, n-hexyl, isopropyl, isobutyl, sec-butyl, tert-butyl, isopentyl, neopentyl, fluoro$C_{1-6}$alkyl, chloro, bromo, acetyl, cyano, $CH_2CN$ and cyclopropyl.

In an embodiment, X is N.

In an embodiment, the compound is selected from:
6-(trifluoromethyl)-N-{[2-(trifluoromethyl)-1H-pyrrolo[2,3-b]pyridin-5-yl]methyl}-4-pyrimidinamine;
6-(1-methylethyl)-N-{[2-(trifluoromethyl)-1H-pyrrolo[2,3-b]pyridin-5-yl]methyl}-4-pyrimidinamine;
6-({[2-(trifluoromethyl)-1H-pyrrolo[2,3-b]pyridin-5-yl]methyl}amino)-4-pyrimidinecarbonitrile;
6-(1,1-dimethylethyl)-N-{[2-(trifluoromethyl)-1H-pyrrolo[2,3-b]pyridin-5-yl]methyl}-4-pyrimidinamine;
6-ethyl-N-{[2-(trifluoromethyl)-1H-pyrrolo[2,3-b]pyridin-5-yl]methyl}-4-pyrimidinamine;
[6-({[2-(trifluoromethyl)-1H-pyrrolo[2,3-b]pyridin-5-yl]methyl}amino)-4-pyrimidinyl]acetonitrile;
1-[6-({[2-(trifluoromethyl)-1H-pyrrolo[2,3-b]pyridin-5-yl]methyl}amino)-4-pyrimidinyl]ethanone;
6-(1,1-difluoroethyl)-N-{[2-(trifluoromethyl)-1H-pyrrolo[2,3-b]pyridin-5-yl]methyl}-4-pyrimidinamine;
6-(1-fluoroethyl)-N-{[2-(trifluoromethyl)-1H-pyrrolo[2,3-b]pyridin-5-yl]methyl}-4-pyrimidinamine;
6-(difluoromethyl)-N-{[2-(trifluoromethyl)-1H-pyrrolo[2,3-b]pyridin-5-yl]methyl}-4-pyrimidinamine;
6-(fluoromethyl)-N-{[2-(trifluoromethyl)-1H-pyrrolo[2,3-b]pyridin-5-yl]methyl}-4-pyrimidinamine;
6-(trifluoromethyl)-N-{[2-(trifluoromethyl)-1H-indol-5-yl]methyl}-4-pyrimidinamine;
6-chloro-N-{[2-(trifluoromethyl)-1H-indol-5-yl]methyl}-4-pyrimidinamine;
6-cyclopropyl-N-{[2-(trifluoromethyl)-1H-pyrrolo[2,3-b]pyridin-5-yl]methyl}-4-pyrimidinamine;
6-(1-fluoro-1-methylethyl)-N-{[2-(trifluoromethyl)-1H-pyrrolo[2,3-b]pyridin-5-yl]methyl}-4-pyrimidinamine;
6-ethyl-5-fluoro-N-{[2-(trifluoromethyl)-1H-pyrrolo[2,3-b]pyridin-5-yl]methyl}-4-pyrimidinamine;
6-chloro-N-{[2-(trifluoromethyl)-1H-pyrrolo[2,3-b]pyridin-5-yl]methyl}-4-pyrimidinamine;
and
6-ethyl-N-{[2-(trifluoromethyl)-1H-indol-5-yl]methyl}-4-pyrimidinamine;
or a salt thereof.

In a further embodiment, the compound if selected from:
6-ethyl-5-methyl-N-{[2-(trifluoromethyl)-1H-pyrrolo[2,3-b]pyridin-5-yl]methyl}-4-pyrimidinamine;
6-(1-fluoroethyl)-5-methyl-N-{[2-(trifluoromethyl)-1H-pyrrolo[2,3-b]pyridin-5-yl]methyl}-4-pyrimidinamine;
6-(1,1-difluoroethyl)-5-methyl-N-{[2-(trifluoromethyl)-1H-pyrrolo[2,3-b]pyridin-5-yl]methyl}-4-pyrimidinamine;
5-methyl-6-(trifluoromethyl)-N-{[2-(trifluoromethyl)-1H-pyrrolo[2,3-b]pyridin-5-yl]methyl}-4-pyrimidinamine;
6-(difluoromethyl)-5-methyl-N-{[2-(trifluoromethyl)-1H-pyrrolo[2,3-b]pyridin-5-yl]methyl}-4-pyrimidinamine;
6-(fluoromethyl)-5-methyl-N-{[2-(trifluoromethyl)-1H-pyrrolo[2,3-b]pyridin-5-yl]methyl}-4-pyrimidinamine;
and
6-cyclopropyl-5-methyl-N-{[2-(trifluoromethyl)-1H-pyrrolo[2,3-b]pyridin-5-yl]methyl}-4-pyrimidinamine;
or a salt thereof.

In a yet further embodiment, there is provided a compound selected from:
6-(1-fluoroethyl)-N-{[2-(trifluoromethyl)-1H-pyrrolo[2,3-b]pyridin-5-yl]methyl}-4-pyrimidinamine;
and
6-(1-fluoro-1-methylethyl)-N-{[2-(trifluoromethyl)-1H-pyrrolo[2,3-b]pyridin-5-yl]methyl}-4-pyrimidinamine;
or a salt thereof.

It will be appreciated that the present invention is intended to include compounds having any combination of the embodiments defined hereinbefore.

For the avoidance of doubt, unless otherwise indicated, the term "substituted" means substituted by one or more defined groups. In the case where groups may be selected from a number of alternative groups, the selected groups may be the same or different.

For the avoidance of doubt, the term "independently" means that where more than one substituent is selected from a number of possible substituents, those substituents may be the same or different.

The compounds of formula (I) may form pharmaceutically acceptable salts, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In one embodiment the salt of the compound of formula (I) is a pharmaceutically acceptable salt, for example, an HCl salt.

Hereinafter, the compounds of formula (I) and their pharmaceutically acceptable salts, are referred to as "the compounds of the invention".

It will be appreciated by those skilled in the art that certain protected derivatives of the compounds of the invention, which may be made prior to a final deprotection stage, may not possess pharmacological activity as such, but may, in certain instances, be administered orally or parenterally and thereafter metabolised in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compound defined in the first aspect.

The compounds of the invention may exist in solvated or hydrated form.

The compounds of the invention or solvates/hydrates of the compounds or salts, may exist in one or more polymorphic forms.

Therefore, according to a further aspect, the invention provides a solvate, hydrate or prodrug of the compounds of the invention.

Certain compounds of the invention may exist in one or more tautomeric forms. All tautomers and mixtures thereof are included in the scope of the present invention.

Certain compounds of the invention may possess one or more chiral centres and so exist in a number of stereoisomeric forms. Compounds having one chiral centre may exist as enantiomers or a racemic mixture containing enantiomers. Compounds having two or more chiral centres may exist as diastereoisomers or enantiomers. All stereoisomers (for example enantiomers and diastereoisomers) and mixtures thereof are included in the scope of the present invention. Racemic mixtures may be separated to give their individual enantiomer using preparative HPLC using a column with a chiral stationary phase or resolved to yield individual enantiomers utilising methods known to those skilled in the art. In addition, chiral intermediate compounds may be resolved and used to prepare individual enantiomers.

The invention also includes all suitable isotopic variations of the compounds of the invention. An isotopic variation of the compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, sulphur, fluorine and chlorine such as $^2H$, $^3H$, $^{13}C$, $^{14}C$, $^{15}N$, $^{17}O$, $^{18}O$, $^{35}S$, $^{18}F$ and $^{36}Cl$ respectively. Certain isotopic variations of the invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples and Preparations hereafter using appropriate isotopic variations of suitable reagents.

It has been found that incorporating deuterium ($^2H$) isotopes in the methylene group between the amine nitrogen atom and the pyrrolo[2,3-b]pyridinyl or indolyl ring in embodiments of compounds of the formula (I) provides advantageous properties. In particular, deuteration at that position has been found to hinder metabolic pathways that invove deprotonation of the compounds of forumla (I) at that position and lessen the formation of unwanted metabolites. Unless otherwise specified, references herein to compounds of the formula (I), including named compounds of the formula (I), relate to both the non-deuterated and the detuerated compounds. For example, references to 6-(1-fluoroethyl)-N-{[2-(trifluoromethyl)-1H-pyrrolo[2,3-b]pyridin-5-yl]methyl}-4-pyrimidinamine; and 6-(1-fluoro-1-methylethyl)-N-{[2-(trifluoromethyl)-1H-pyrrolo[2,3-b]pyridin-5-yl]methyl}-4-pyrimidinamine relate not only to the In one aspect of the invention, there is provided a compound of formula (Ia) or a salt thereof:

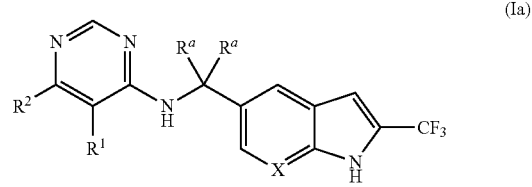

(Ia)

wherein
R$^1$ is independently selected from the group consisting of H, C$_{1-6}$alkyl, haloC$_{1-6}$alkyl and halo;
R$^2$ is independently selected from the group consisting of C$_{1-6}$alkyl, haloC$_{1-6}$alkyl, halo, acetyl, cyano, CH$_2$CN and cyclopropyl;
each R$^a$ is independently selected from H and D; and
X is CH or N.

In a further aspect of the invention, at least one R$^a$ is D. In a yet further aspect of the invention, each R$^a$ is D.

In one embodiment, the invention provides a compound selected from 6-(1-fluoroethyl)-N-{[2-(trifluoromethyl)-1H-pyrrolo[2,3-b]pyridin-5-yl]methyl}-4-pyrimidinamine-d$_2$; 6-cyclopropyl-N-{[2-(trifluoromethyl)-1H-pyrrolo[2,3-b]pyridin-5-yl]methyl}-4-pyrimidinamine-d$_2$ and 6-(1-fluoro-1-methylethyl)-N-{[2-(trifluoromethyl)-1H-pyrrolo[2,3-b]pyridin-5-yl]methyl}-4-pyrimidinamine-d$_2$ or a pharmaceutically acceptable salt thereof.

In a compound of formula (Ia), when a particular position is designated as having deuterium, it is understood that the abundance of deuterium at that position is substantially greater than the natural abundance of deuterium, which is 0.015%. A position designated as having deuterium typically has a minimum isotopic enrichment factor, i.e. ratio between the isotopic abundance and the natural abundance, of at least 3000 (45% deuterium incorporation at each designated deuterium atom). In other embodiments, a compound of formula (Ia) has an isotopic enrichment factor for each designated deuterium atom of at least 3500 (52.5% deuterium incorporation), at least 4000 (60% deuterium incorporation), at least 5000 (75% deuterium incorporation), at least 6000 (90% deuterium incorporation), at least 6333.3 (95% deuterium incorporation), or at least 6600 (99% deuterium incorporation). In the compounds of formula (Ia) any atom not specifically designated as a particular isotope is meant to represent any stable isotope of that atom unless otherwise stated.

For the avoidance of doubt and unless otherwise specified, references herein to compounds of the formula (I), including named compounds of the formula (I), relate to all suitable isotopic variations, including deuterated compounds, such as, for example, compounds of the formula (Ia) wherein each $R^a$ is H and compounds wherein one or more $R^a$ is D. For example, references to 6-(1-fluoroethyl)-N-{[2-(trifluoromethyl)-1H-pyrrolo[2,3-b]pyridin-5-yl]methyl}-4-pyrimidinamine; and 6-(1-fluoro-1-methylethyl)-N-{[2-(trifluoromethyl)-1H-pyrrolo[2,3-b]pyridin-5-yl]methyl}-4-pyrimidinamine encompass the deuterated analogues 6-(1-fluoroethyl)-N-{[2-(trifluoromethyl)-1H-pyrrolo[2,3-b]pyridin-5-yl]methyl}-4-pyrimidinamine-$d_2$; and 6-(1-fluoro-1-methylethyl)-N-{[2-(trifluoromethyl)-1H-pyrrolo[2,3-b]pyridin-5-yl]methyl}-4-pyrimidinamine-$d_2$.

Compounds of the invention may be prepared in a variety of ways. In the following reaction schemes and hereinafter, unless otherwise stated X, $R^1$ and $R^2$ are as defined in the first aspect. These processes form further aspects of the invention.

Throughout the specification, general formulae are designated by Roman numerals (I), (II), (III), (IV) etc. Subsets of these general formulae are defined as (Ia), (Ib), (Ic), etc. . . . (IVa), (IVb), (IVc) etc.

Compounds of formula (I) may be prepared according to scheme 1 by reaction of compounds of formula (II) with compounds of formula (III). Typical conditions comprise treatment with a suitable base such as DIPEA or potassium carbonate in a suitable solvent such as NMP or DMSO at various temperatures ranging from room temperature to 150° C.

Scheme 1

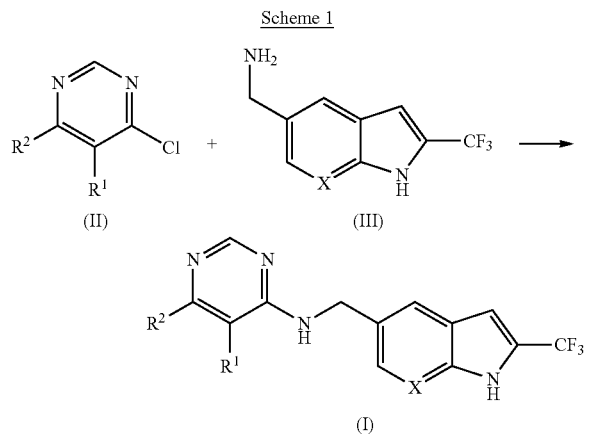

Alternatively, compounds of formula (I) may be prepared from compounds of formula (IV) according to scheme 2. Typical conditions comprise heating at 80° C. in a suitable solvent such as IPA.

Scheme 2

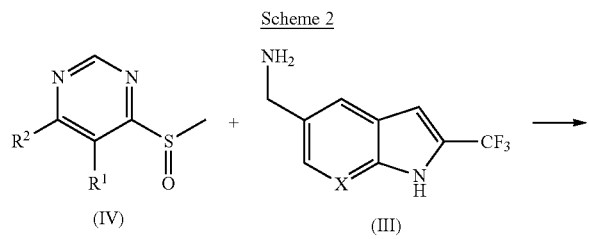

Compounds of formula (IIIa), i.e. compounds of formula (III) where X is nitrogen, may be prepared according to scheme 3. Treatment of compounds of formula (V) with trifluoroacetic anhydride in the presence of a base (such as DIPEA) in a suitable solvent (such as DCM) gives compounds of formula (VI). Coupling of compounds of formula (VI) with a suitable β-keto ester (such as tert-butyl acetoacetate), using a suitable catalyst system (such as copper (I) iodide and L-proline), with a suitable base (such as cesium carbonate) in a suitable solvent (such as DMSO) at a temperature of 80° C. gives compounds of formula (VII) (Chen et al., Org. Lett. 2008, 10, 4, 625-628). Hydrolysis of compounds of formula (VII) using a suitable acid (such as TFA) in a suitable solvent (such as DCM) gives compounds of formula (VIII). Decarboxylation of compounds of formula (VIII) in a suitable mixture of solvents (such as NMP and water) at a temperature of 120° C. gives compounds of formula (IX). Compounds of formula (IIIa) are obtained by reduction of compounds of formula (IX) with borane.

Scheme 3

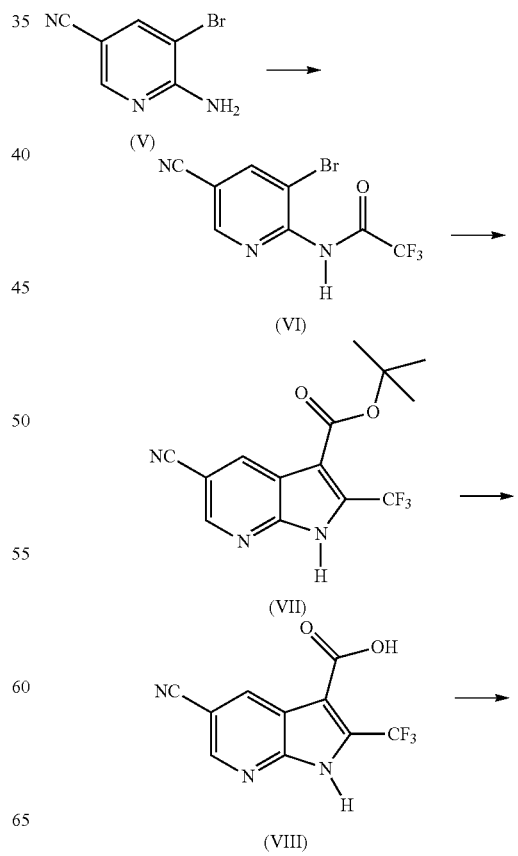

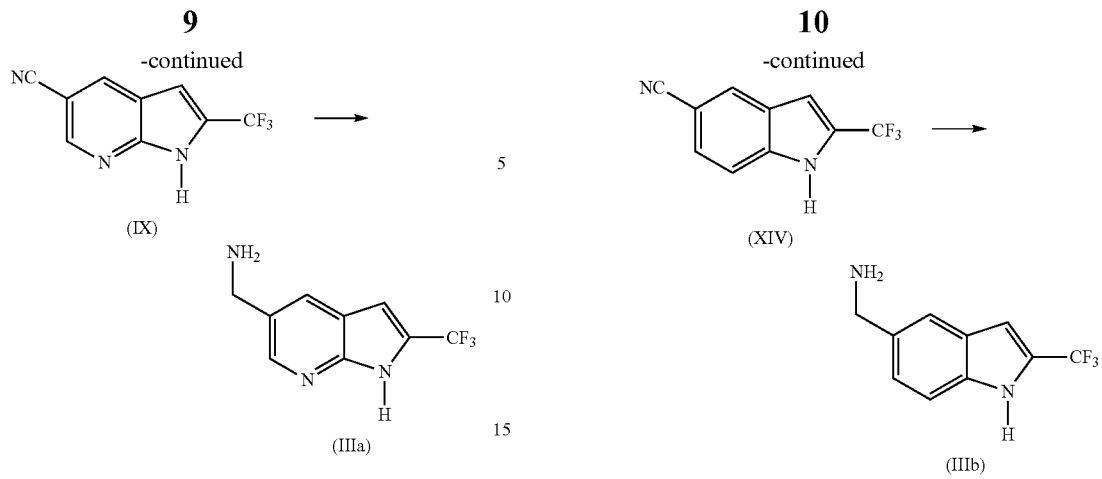

Compounds of formula (IIIb), i.e. compounds of formula (III) where X is carbon, may be prepared according to scheme 4. Treatment of compounds of formula (X) with trifluoroacetic anhydride in the presence of a base (such as triethylamine) in a suitable solvent (such as DCM) gives compounds of formula (XI). Halogenation of compounds of formula (XI) with a suitable radical halogen source such as sulfuryl chloride or N-bromosuccinimide in a suitable solvent (such as carbon tetrachloride) gives compounds of formula (XII). Treating compounds of formula (XII) with a phosphine derivative (such as triphenylphosphine) gives compounds of formula (XIII), which may be cyclised to give compounds of formula (XIV). Typical cyclisation conditions comprise heating in a suitable solvent (such as DMF) to a temperature in excess of 100° C. Compounds of formula (IIIb) are obtained by reduction of compounds of formula (XIV) with borane or nickel borohydride.

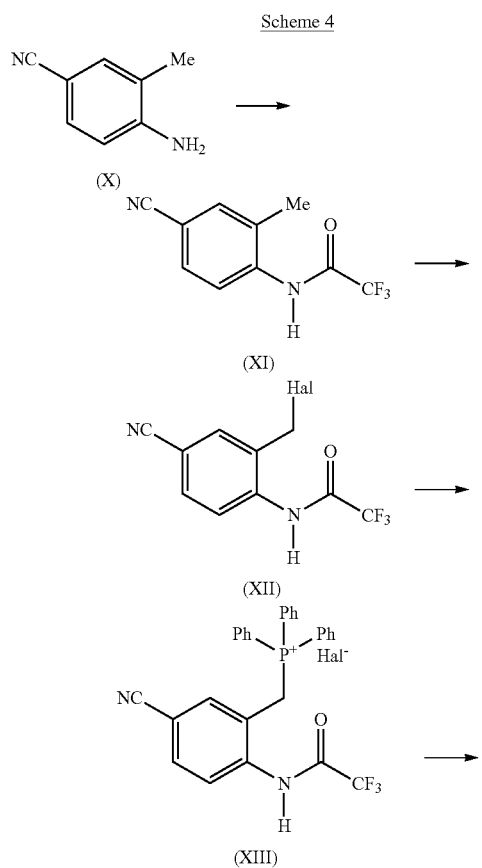

Compounds of formula (II) may be prepared according to scheme 5. Treatment of compounds of formula (XV) with formamidine acetate in the presence of a suitable base (such as sodium methoxide) in a suitable solvent (such as methanol) gives compounds of formula (XVI). Compounds of formula (II) are obtained by treatment of compounds of formula (XVI) with phosphorus oxychloride in the presence of a suitable base (such as triethylamine) with or without a suitable solvent (such as DCM).

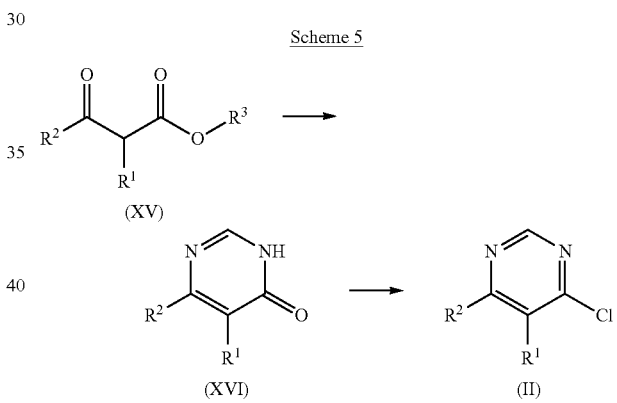

Compounds of formula (IIa), i.e. compounds of formula (II) where $R^1$ is hydrogen and $R^2$ is cyano, may be prepared according to scheme 6. Treatment of compounds of formula (XVII) with formamidine hydrochloride in the presence of a suitable base (such as triethylamine) in a suitable solvent (such as acetonitrile) gives compounds of formula (XVIII). Amidation of compounds of formula (XVIII) using ammonia gives compounds of formula (XIX). Compounds of formula (IIa) are obtained by treatment of compounds of formula (XIX) with phosphorus oxychloride.

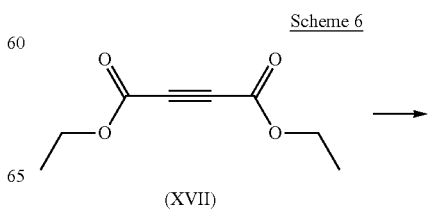

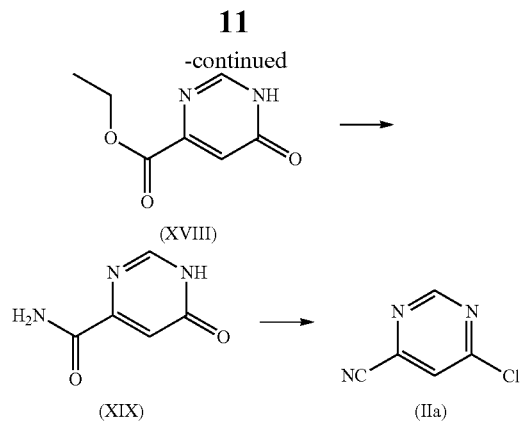

Compounds of formula (IVa), i.e. compounds of formula (IV) where R¹ is hydrogen and R² is methyl cyano, may be prepared according to scheme 7. Displacement of compounds of formula (XX) with sodium thiomethoxide in a suitable solvent (such as THF) gives compounds of formula (XXI). Displacement of compounds of formula (XXI) with methyl cyanoacetate in the presence of a suitable base (such as sodium hydride) in a suitable solvent (such as DMSO) gives compounds of formula (XXII). Decarboxylation of compounds of formula (XXII) in the presence of sodium chloride in a suitable mixture of solvents (such as water and DMSO) gives compounds of formula (XXIII). Compounds of formula (IVa) are obtained by oxidation of compounds of formula (XXIII) using a suitable oxidising agent (such as 3-chloroperoxybenzoic acid) in a suitable solvent (such as DCM).

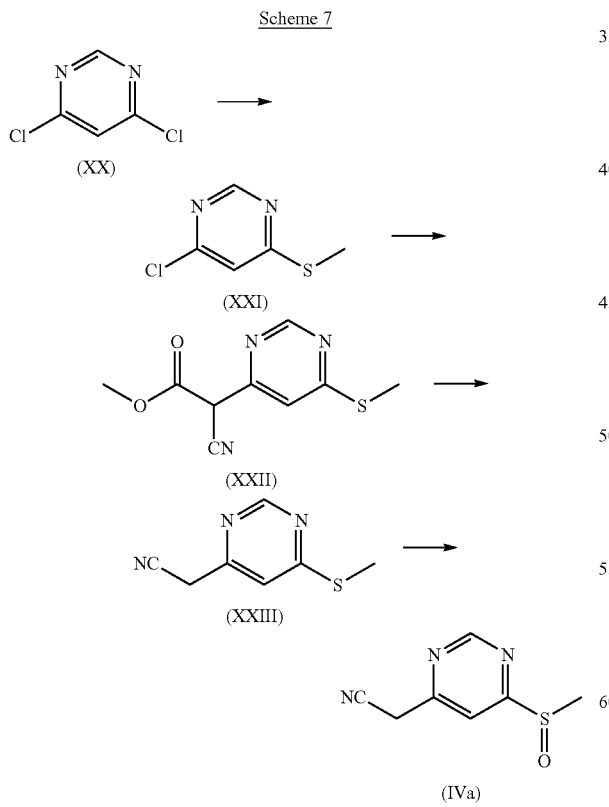

Compounds of formula (IIb), i.e. compounds of formula (II) where R¹ is hydrogen and R² is 1,1-difluoroethyl, may be prepared according to scheme 8. Stille reaction of compounds of formula (XX) with tributyl[1-(ethyloxy)ethenyl]stannane in the presence of a suitable catalyst (such as bis(triphenylphosphine)palladium(II) chloride) in a suitable solvent (such as DMF) at a temperature of 80° C. gives compounds of formula (XXIV). Treatment of compounds of formula (XXIV) with a suitable acid (such as hydrochloric acid) in a suitable solvent (such as acetone) gives compounds of formula (XXV). Compounds of formula (IIb) may be prepared by treatment of compounds of formula (XXV) with (diethylamino)sulphur trifluoride in a suitable solvent (such as DCM).

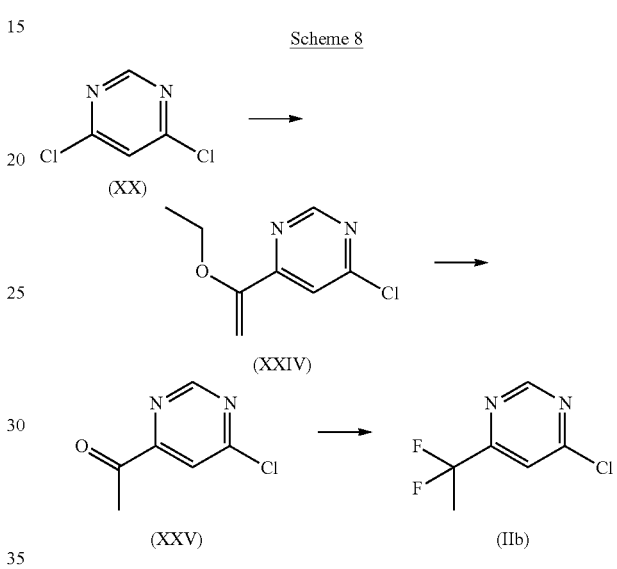

Compounds of formula (IIc), i.e. compounds of formula (II) where R¹ is hydrogen and R² is 1-fluoroethyl, may be prepared according to scheme 9. Reduction of compounds of formula (XXV) using a suitable reducing agent (such as sodium borohydride) in a suitable solvent (such as ethanol) gives compounds of formula (XXVI). Compounds of formula (IIc) may be prepared by treatment of compounds of formula (XXVI) with (diethylamino)sulphur trifluoride in a suitable solvent (such as DCM).

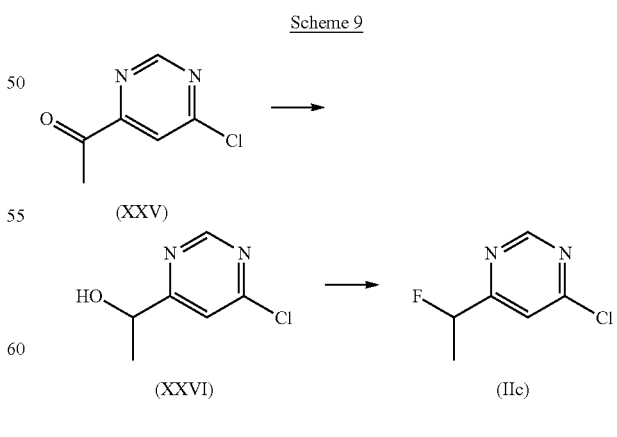

Compounds of formula (IId), i.e. compounds of formula (II) where R¹ is hydrogen and R² is fluoromethyl, may be prepared according to scheme 10. Compounds of formula (XXVII) may be prepared by Negishi coupling of compounds of formula (XX) with iodo{[(phenylcarbonyl)oxy]methyl}zinc in the presence of a suitable catalyst (such as tetrakis(triphenylphosphine)palladium(0)) in a suitable solvent (such as THF). Treatment of compounds of formula (XXVIII) with a suitable base (such as sodium methoxide) in a suitable solvent (such as methanol) gives compounds of formula (XXVIII). Compounds of formula (IId) may be prepared by treatment of compounds of formula (XXVIII) with (diethylamino)sulphur trifluoride in a suitable solvent (such as DCM).

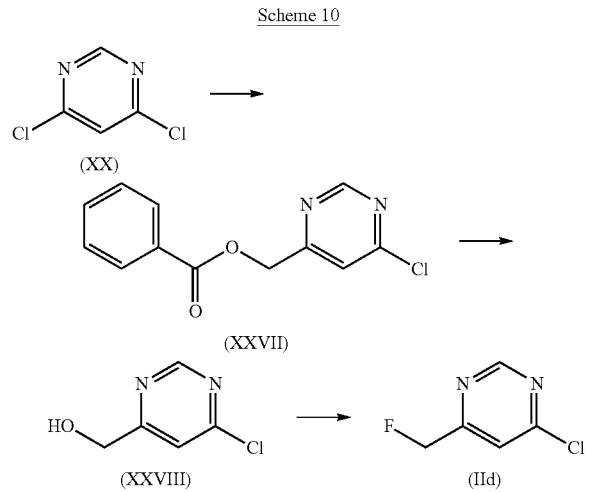

Compounds of formula (IIe), i.e. compounds of formula (II) where $R^1$ is hydrogen and $R^2$ is 1-fluoro-1-methylethyl, may be prepared according to scheme 11. Treatment of compounds of formula (XXV) with methyl magnesium bromide in a suitable solvent (such as THF) gives compounds of formula (XXIX). Compounds of formula (IIe) may be prepared by treatment of compounds of formula (XXIX) with (diethylamino)sulphur trifluoride in a suitable solvent (such as DCM).

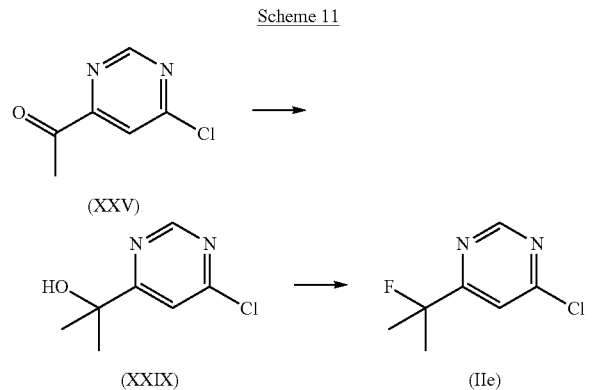

Compounds of formula (IIf), i.e. compounds of formula (II) where $R^1$ is hydrogen and $R^2$ is cyclopropyl, may be prepared according to scheme 12. Suzuki reaction of compounds of formula (XX) with potassium cyclopropyl(trifluoro)borate in the presence of a suitable ligand (such as di(1-adamantyl)-n-butylphosphine), a suitable catalyst (such as palladium(II) acetate) and a suitable base (such as cesium carbonate) in a suitable solvent (such as toluene) at a temperature of 100° C. gives compounds with formula (IIf).

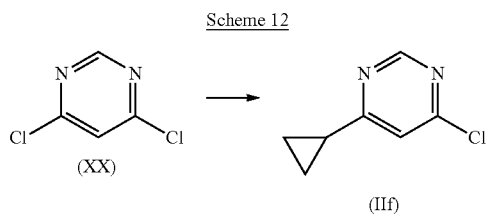

Dueterated compounds of the formula (I) may be prepared by analogous procedures to those used to prepare the non-deuterated compounds. For example, compounds of formula (IIIc) and compounds of the formula (IIId), which are compounds of formula (III) where the hydrogen atoms on the carbon atom between the primary amine group and the biclyclic heterocylic ring system are deuterium and where where X is nitrogen in the case of compounds of the formula (IIIc) and where X is CH in the case of compounds of the formula (IIId), may be prepared according to scheme 13 or scheme 14 respectively. Treatment of compounds of formula (IX) or compounds of the formula (XIV) with nickel (II) chloride hexahydrate and di-t-butyl dicarbonate in a suitable solvent (such as dry methanol), followed by the addition of sodium borodeuteride gives compounds of formula (XXI) and compounds of formula (XXII) respectively. Treatment of compounds of the formula (XXI) and compounds of formula (XXII) with trifluoroacetic acid in a suitable solvent (such as DCM) affords compounds of the formula (IIIc) and compounds of the formula (IIId).

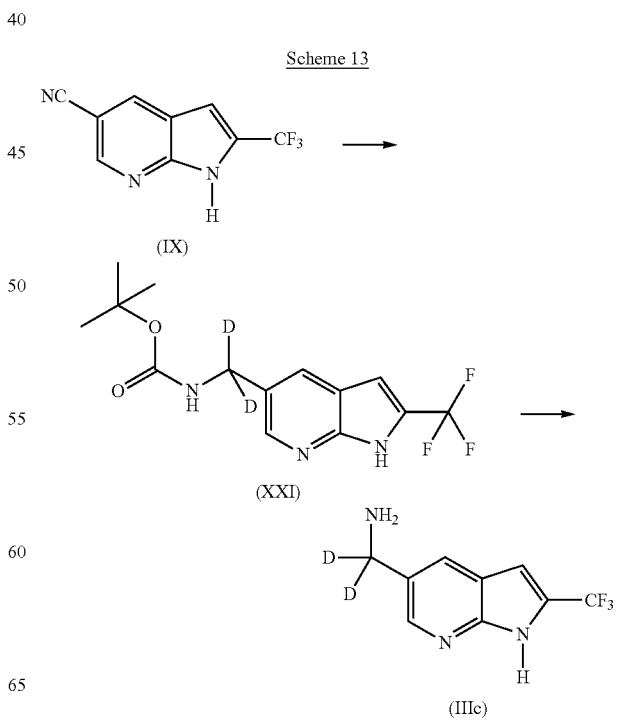

Scheme 14

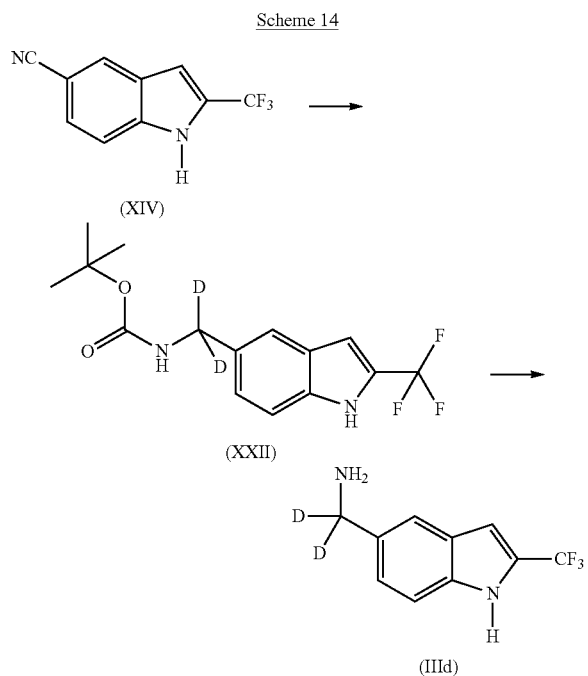

Compounds of the formula (IIIc) and compounds of the formula (IIId) may be used in the procedures described above with reference to schemes 1 and 2 to afford compounds of the formula (Ib).

Salts may be prepared conventionally by reaction with the appropriate acid or acid derivative.

The compounds of the invention may be useful for the treatment of diseases and conditions mediated by positive allosteric modulation of the α7 nAChR or diseases and conditions which are associated with modulation of the α7 nAChR. Diseases or conditions mediated by positive allosteric modulation of the α7 nAChR or diseases and conditions which are associated with modulation of the α7 nAChR include (the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10):

i) Psychotic disorders for example Schizophrenia (including the subtypes Paranoid Type (295.30), Disorganised Type (295.10), Catatonic Type (295.20), Undifferentiated Type (295.90) and Residual Type (295.60)); Schizophreniform Disorder (295.40); Schizoaffective Disorder (295.70) (including the subtypes Bipolar Type and Depressive Type); Delusional Disorder (297.1) (including the subtypes Erotomanic Type, Grandiose Type, Jealous Type, Persecutory Type, Somatic Type, Mixed Type and Unspecified Type); Brief Psychotic Disorder (298.8); Shared Psychotic Disorder (297.3); Psychotic Disorder due to a General Medical Condition (including the subtypes with Delusions and with Hallucinations); Substance-Induced Psychotic Disorder (including the subtypes with Delusions (293.81) and with Hallucinations (293.82)); and Psychotic Disorder Not Otherwise Specified (298.9).

ii) cognitive impairment including for example the treatment of impairment of cognitive functions including attention, orientation, learning disorders, memory (i.e. memory disorders, amnesia, amnesic disorders, transient global amnesia syndrome and age-associated memory impairment) and language function; as well as cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to other diseases such as schizophrenia, bipolar disorder, depression and other psychiatric disorders, and post-electroconvulsive treatment related cognitive disorders; and dyskinetic disorders such as Parkinson's disease, neuroleptic-induced parkinsonism, and tardive dyskinesias.

iii) Depression and mood disorders for example Depressive Episodes (including Major Depressive Episode, Manic Episode, Mixed Episode and Hypomanic Episode); Depressive Disorders (including Major Depressive Disorder, Dysthymic Disorder (300.4), Depressive Disorder Not Otherwise Specified (311)); Bipolar Disorders (including Bipolar I Disorder, Bipolar II Disorder (i.e. Recurrent Major Depressive Episodes with Hypomanic Episodes) (296.89), Cyclothymic Disorder (301.13) and Bipolar Disorder Not Otherwise Specified (296.80)); Other Mood Disorders (including Mood Disorder due to a General Medical Condition (293.83) which includes the subtypes With Depressive Features, With Major Depressive-like Episode, With Manic Features and With Mixed Features); Substance-Induced Mood Disorder (including the subtypes With Depressive Features, With Manic Features and With Mixed Features); and Mood Disorder Not Otherwise Specified (296.90).

iv) Anxiety disorders for example Social Anxiety Disorder; Panic Attack; Agoraphobia, Panic Disorder; Agoraphobia Without History of Panic Disorder (300.22); Specific Phobia (300.29) (including the subtypes Animal Type, Natural Environment Type, Blood-Injection-Injury Type, Situational Type and Other Type); Social Phobia (300.23); Obsessive-Compulsive Disorder (300.3); Posttraumatic Stress Disorder (309.81); Acute Stress Disorder (308.3); Generalized Anxiety Disorder (300.02); Anxiety Disorder Due to a General Medical Condition (293.84); Substance-Induced Anxiety Disorder; and Anxiety Disorder Not Otherwise Specified (300.00).

v) Substance-related disorders for example Substance Use Disorders (including Substance Dependence, Substance Craving and Substance Abuse); Substance-Induced Disorders (including Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders (including Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9)); Amphetamine (or Amphetamine-Like)-Related Disorders (for example Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9)); Caffeine Related Disorders (including Caffeine Intoxication (305.90), Caffeine-Induced Anxiety Disorder, Caffeine-Induced Sleep Disorder and Caffeine-Related Disorder Not Otherwise Specified (292.9)); Cannabis-Related Disorders (including Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9)); Cocaine-Related Disorders (including Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9)); Hallucinogen-Related Disorders (including Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9)); Inhalant-Related Disorders (including Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9)); Nicotine-Related Disorders (including Nicotine Dependence (305.1), Nicotine Withdrawal (292.0) and Nicotine-Related Disorder Not Otherwise Specified (292.9)); Opioid-Related Disorders (including Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9)); Phencyclidine (or Phencyclidine-Like)-Related Disorders (including Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9)); Sedative-, Hypnotic-, or Anxiolytic-Related Disorders (including Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9)); Polysubstance-Related Disorder (including Polysubstance Dependence (304.80)); and Other (or Unknown) Substance-Related Disorders (including Anabolic Steroids, Nitrate Inhalants and Nitrous Oxide).

vi) Sleep disorders for example primary sleep disorders such as Dyssomnias (including Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47)); primary sleep disorders such as Parasomnias (including Nightmare Disorder (307.47), Sleep Terror Disorder (307.46), Sleepwalking Disorder (307.46) and Parasomnia Not Otherwise Specified (307.47)); Sleep Disorders Related to Another Mental Disorder (including Insomnia Related to Another Mental Disorder (307.42) and Hypersomnia Related to Another Mental Disorder (307.44)); Sleep Disorder Due to a General Medical Condition; and Substance-Induced Sleep Disorder (including the subtypes Insomnia Type, Hypersomnia Type, Parasomnia Type and Mixed Type).

vii) Eating disorders such as Anorexia Nervosa (307.1) (including the subtypes Restricting Type and Binge-Eating/Purging Type); Bulimia Nervosa (307.51) (including the subtypes Purging Type and Nonpurging Type); Obesity; Compulsive Eating Disorder; Binge Eating Disorder; and Eating Disorder Not Otherwise Specified (307.50).

viii) Autism Spectrum Disorders including Autistic Disorder (299.00), Asperger's Disorder, Rett's Disorder, Childhood Disintegrative Disorder and Pervasive Developmental Disorder Not Otherwise Specified.

ix) Attention-Deficit/Hyperactivity Disorder (including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9)); Hyperkinetic Disorder; Disruptive Behaviour Disorders such as Conduct Disorder (including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

x) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

xi) Sexual dysfunctions such as Sexual Desire Disorders (including Hypoactive Sexual Desire Disorder (302.71) and Sexual Aversion Disorder (302.79)); sexual arousal disorders (including Female Sexual Arousal Disorder (302.72) and Male Erectile Disorder (302.72)); orgasmic disorders (including Female Orgasmic Disorder (302.73), Male Orgasmic Disorder (302.74) and Premature Ejaculation (302.75)); sexual pain disorder (including Dyspareunia (302.76) and Vaginismus (306.51)); Sexual Dysfunction Not Otherwise Specified (302.70); paraphilias (including Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9)); gender identity disorders (including Gender Identity Disorder in Children (302.6) and Gender Identity Disorder in Adolescents or Adults (302.85)); and Sexual Disorder Not Otherwise Specified (302.9).

The compounds of the invention may also be useful in treating inflammation, inflammatory pain, rheumatoid arthritis and sepsis.

The compounds of the invention may also be useful in treating pain, including inflammatory pain and neuropathic pain, especially neuropathic pain.

In one embodiment, the patient is a human. The term "treatment" includes prophylaxis, where this is appropriate for the relevant condition(s).

Thus in one aspect, the present invention provides a compound of formula (I) as hereinbefore described or a salt thereof for use as a medicament.

In one aspect, the present invention provides a compound of formula (I) as hereinbefore described or a salt thereof for use in treating a disease which is associated with a reduction in function of α7 nicotinic acetyl choline receptor.

In one aspect, the present invention provides a compound of formula (I) as hereinbefore described or a salt thereof for use in treating a disease which benefits from positive allosteric modulation of the α7 nicotinic acetyl choline receptor.

In one aspect, the present invention provides a compound of formula (I) as hereinbefore described or a salt thereof for use as a positive allosteric modulator of the α7 nicotinic acetyl choline receptor.

In another aspect, the invention provides a compound of formula (I) as hereinbefore described or a salt thereof for use in the treatment of a psychotic disorder. In one embodiment, the invention provides a compound of formula (I) as hereinbefore described or a salt thereof for use in the treatment of schizophrenia. In one embodiment, the invention provides a compound of formula (I) as hereinbefore described or a salt thereof for use in the treatment of anxiety or depression.

The invention also provides a compound of formula (I) as hereinbefore described or a salt thereof for use in the treatment of cognitive impairment.

The invention also provides a compound of formula (I) as hereinbefore described or a salt thereof for use in the treatment of Alzheimer's disease.

The invention also provides a compound of formula (I) as hereinbefore described or a salt thereof for use in the treatment of pain, including inflammatory pain and neuropathic pain, especially neuropathic pain.

In another aspect, the invention provides the use of a compound of formula (I) as hereinbefore described or a salt thereof in the manufacture of a medicament for treating a disease which is associated with a reduction in function of α7 nicotinic acetyl choline receptor.

In another aspect, the invention provides the use of a compound of formula (I) as hereinbefore described or a salt thereof in the manufacture of a medicament for use in treating a disease which benefits from positive allosteric modulation of the α7 nicotinic acetyl choline receptor.

In another aspect, the invention provides the use of a compound of formula (I) as hereinbefore described or a salt thereof in the manufacture of a medicament for the positive allosteric modulation of the α7 nicotinic acetyl choline receptor.

In another aspect, the invention provides the use of a compound of formula (I) as hereinbefore described or a salt thereof in the manufacture of a medicament for use in the treatment of a psychotic disorder. In another aspect, the invention provides the use of a compound of formula (I) as hereinbefore described or a salt thereof in the manufacture of a medicament for use in the treatment of schizophrenia. In another aspect, the invention provides the use of a compound of formula (I) as hereinbefore described or a salt thereof in the manufacture of a medicament for use in the treatment of anxiety or depression.

In another aspect, the invention provides the use of a compound of formula (I) as hereinbefore described or a salt thereof in the manufacture of a medicament for use in the treatment of cognitive impairment.

In another aspect, the invention provides the use of a compound of formula (I) as hereinbefore described or a salt thereof in the manufacture of a medicament for use in the treatment of Alzheimer's disease.

In another aspect, the invention provides the use of a compound of formula (I) as hereinbefore described or a salt thereof in the manufacture of a medicament for use in the treatment of pain, including inflammatory pain and neuropathic pain, especially neuropathic pain.

In another aspect, the invention provides a method of treating a disease which is associated with a reduction in function of α7 nicotinic acetyl choline receptor, which comprises administering to a human in need thereof an effective amount of a compound of formula (I) as hereinbefore described or a salt thereof.

In one aspect, the present invention provides a method of treating a disease which benefits from positive allosteric modulation of the α7 nicotinic acetyl choline receptor, which comprises administering to a human in need thereof an effective amount of a compound of formula (I) as hereinbefore described or a salt thereof.

In one aspect, the present invention provides a method for the positive allosteric modulation of the α7 nicotinic acetyl choline receptor, which comprises administering to a human an effective amount of a compound of formula (I) as hereinbefore described or a salt thereof.

In another aspect, the invention provides a method for use in treating a psychotic disorder, which comprises administering to a human in need thereof an effective amount of a compound of formula (I) as hereinbefore described or a salt thereof.

In one embodiment, the invention provides a method for treating schizophrenia, which comprises administering to a human in need thereof an effective amount of a compound of formula (I) as hereinbefore described or a salt thereof.

In one embodiment, the invention provides a method for treating anxiety or depression, which comprises administering to a human in need thereof an effective amount of a compound of formula (I) as hereinbefore described or a salt thereof.

The invention also provides a method for treating cognitive impairment, which comprises administering to a human in need thereof an effective amount of a compound of formula (I) as hereinbefore described or a salt thereof.

The invention also provides a method for treating Alzheimer's disease, which comprises administering to a human in need thereof an effective amount of a compound of formula (I) as hereinbefore described or a salt thereof.

The invention also provides a method for treating pain, including inflammatory pain and neuropathic pain, especially neuropathic pain, which comprises administering to a human in need thereof an effective amount of a compound of formula (I) as hereinbefore described or a salt thereof.

In general, compounds of formula (I) or a salt thereof may be administered in doses ranging from about 0.1 mg to about 1000 mg per day, in single or divided doses (i.e., from 1 to 4 doses per day), although variations will necessarily occur depending upon the weight, age and condition of the patient being treated, as well as the particular route of administration chosen. In an embodiment, the dose is administered once daily. In an embodiment, the dosage level is in the range of about 0.1 mg/kg to about 500 mg/kg body weight per day. In a further embdodiment, the dosage level is in the range of about 0.1 mg/kg to about 100 mg/kg body weight per day.

The compounds of formula (I) and salts thereof may also be suitable for use in combination with other actives, such as typical and atypical antipsychotics, mood stabilisers, antidepressants, anxiolytics, drugs for extrapyramidal side effects and cognitive enhancers to provide improved treatment of psychotic disorders.

The combination therapies of the invention are, for example, administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of a compound of formula (I) or a salt thereof and at least one antipsychotic agent, a mood stabiliser, an antidepressant, an anxiolytic, a drug for extrapyramidal side effects or a cognitive enhancer are within the scope of the current invention. In one embodiment of adjunctive therapeutic administration as described herein, a patient is typically stabilised on a therapeutic administration of one or more of the components for a period of time and then receives administration of another component. The compounds of formula (I) or a salt thereof may be administered as adjunctive therapeutic treatment to patients who are receiving administration of at least one antipsychotic agent, a mood stabiliser, an antidepressant, an anxiolytic, a drug for extrapyramidal side effects or a cognitive enhancer, but the scope of the invention also includes the adjunctive therapeutic administration of at least one antipsychotic agent, a mood stabiliser, an antidepressant, an anxiolytic, a drug for extrapyramidal side effects or a cognitive enhancer to patients who are receiving administration of compounds of formula (I) or a salt thereof.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect therefore, the invention provides a method of treatment of a psychotic disorder by adjunctive therapeutic administration of a compound of formula (I) or a salt thereof to a patient receiving therapeutic administration of at least one antipsychotic agent. In a further aspect, the invention provides the use of a compound of formula (I) or a salt thereof in the manufacture of a medicament for adjunctive therapeutic administration for the treatment of a psychotic disorder in a patient receiving therapeutic administration of at least one antipsychotic agent. The invention further provides a compound of formula (I) or a salt thereof for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of a compound of formula (I) or a salt thereof. In a further aspect, the invention provides the use of at least one antipsychotic agent in the manufacture of a medicament for adjunctive therapeutic administration for the treatment of a psychotic disorder in a patient receiving therapeutic administration of a compound of formula (I) or a salt thereof. The invention further provides at least one antipsychotic agent for adjunctive therapeutic administration for the treatment of a psychotic disorder in a patient receiving therapeutic administration of a compound of formula (I) or a salt thereof.

In a further aspect, the invention provides a method of treatment of a psychotic disorder by simultaneous therapeutic administration of a compound of formula (I) or a salt thereof in combination with at least one antipsychotic agent. The invention further provides the use of a combination of a compound of formula (I) or a salt thereof and at least one antipsychotic agent in the manufacture of a medicament for simultaneous therapeutic administration in the treatment of a psychotic disorder. The invention further provides the use of a compound of formula (I) or a salt thereof in the manufacture of a medicament for simultaneous therapeutic administration with at least one antipsychotic agent in the treatment of a psychotic disorder. The invention further provides a compound of formula (I) or a salt thereof for use for simultaneous therapeutic administration with at least one antipsychotic agent in the treatment of a psychotic disorder. The invention further provides the use of at least one antipsychotic agent in the manufacture of a medicament for simultaneous therapeutic administration with a compound of formula (I) or a salt thereof in the treatment of a psychotic disorder.

In a further aspect, the invention provides a kit-of-parts for use in the treatment of a psychotic disorder comprising a first dosage form comprising a compound of formula (I) or a salt thereof and one or more further dosage forms each comprising an antipsychotic agent for simultaneous therapeutic administration.

In another aspect, the invention provides a method of treatment of a psychotic disorder by adjunctive therapeutic administration of a compound of the present invention to a patient receiving therapeutic administration of an active ingredient selected from the group consisting of: a mood stabiliser, an antidepressant, an anxiolytic, a drug for extrapyramidal side effects and a cognitive enhancer.

In a further aspect, the invention provides the use of a compound of the present invention in the manufacture of a medicament for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

The invention also provides the use of a compound of the present invention in adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

The invention further provides the use of a compound of the present invention for use for adjunctive therapeutic administration for the treatment of a psychotic disorder in a patient receiving therapeutic administration of an active ingredient selected from the group consisting of: a mood stabiliser, an antidepressant, an anxiolytic, a drug for extrapyramidal side effects and a cognitive enhancer.

In a further aspect, the invention provides a method of treatment of a psychotic disorder by adjunctive therapeutic administration of an active ingredient selected from the group consisting of: a mood stabiliser, an antidepressant, an anxiolytic, a drug for extrapyramidal side effects and a cognitive enhancer to a patient receiving therapeutic administration of a compound of the present invention.

In a further aspect, the invention provides the use of an active ingredient selected from the group consisting of: a mood stabiliser, an antidepressant, an anxiolytic, a drug for extrapyramidal side effects and a cognitive enhancer in the manufacture of a medicament for adjunctive therapeutic administration for the treatment of a psychotic disorder in a patient receiving therapeutic administration of a compound of the present invention.

The invention also provides the use of an active ingredient selected from the group consisting of: a mood stabiliser, an antidepressant, an anxiolytic, a drug for extrapyramidal side effects and a cognitive enhancer for adjunctive therapeutic administration for the treatment of a psychotic disorder in a patient receiving therapeutic administration of a compound of the present invention.

In a further aspect, the invention provides a method of treatment of a psychotic disorder by simultaneous therapeutic administration of a compound of the present invention in combination with an active ingredient selected from the group consisting of: a mood stabiliser, an antidepressant, an anxiolytic, a drug for extrapyramidal side effects and a cognitive enhancer.

The invention further provides the use of a combination of a compound of the present invention and an active ingredient selected from the group consisting of: a mood stabiliser, an antidepressant, an anxiolytic, a drug for extrapyramidal side effects and a cognitive enhancer in the manufacture of a medicament for simultaneous therapeutic administration in the treatment of a psychotic disorder.

The invention further provides the use of a combination of a compound of the present invention and an active ingredient selected from the group consisting of: a mood stabiliser, an antidepressant, an anxiolytic, a drug for extrapyramidal side effects and a cognitive enhancer for simultaneous therapeutic administration in the treatment of a psychotic disorder.

The invention further provides the use of a compound of the present invention in the manufacture of a medicament for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides the use of a compound of the present invention for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides a compound of the present invention for use for simultaneous therapeutic administration with an active ingredient selected from the group consisting of: a mood stabiliser, an antidepressant, an anxiolytic, a drug for extrapyramidal side effects and a cognitive enhancer in the treatment of a psychotic disorder.

The invention further provides the use of an active ingredient selected from the group consisting of: a mood stabiliser, an antidepressant, an anxiolytic, a drug for extrapyramidal side effects and a cognitive enhancer in the manufacture of a medicament for simultaneous therapeutic administration with a compound of the present invention in the treatment of a psychotic disorder.

The invention further provides the use of an active ingredient selected from the group consisting of: a mood stabiliser, an antidepressant, an anxiolytic, a drug for extrapyramidal side effects and a cognitive enhancer for simultaneous therapeutic administration with a compound of the present invention in the treatment of a psychotic disorder.

In a further aspect, the invention provides a kit-of-parts for use in the treatment of a psychotic disorder comprising a first dosage form comprising a compound of the present invention and one or more further dosage forms each comprising an active ingredient selected from the group consisting of: a mood stabiliser, an antidepressant, an anxiolytic, a drug for extrapyramidal side effects and a cognitive enhancer for simultaneous therapeutic administration.

Examples of antipsychotic drugs that may be useful in the present invention include, but are not limited to: sodium channel blockers; mixed 5HT/dopamine receptor antagonists; mGluR5 positive modulators; D3 antagonists; 5HT6 angatonists; nicotinic alpha-7 modulators; glycine transporter GlyT1 inhibitors; D2 partial agonist/D3 antagonist/H3 antagonists; AMPA modulators; NK3 antagonists such as osanetant and talnetant; an atypical antipsychotic, for example clozapine, olanzapine, risperidone, quetiapine, aripirazole, ziprasidone and amisulpride; butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs that may be suitable for use in the present invention are as follows: clozapine (available under the tradename CLOZARIL™, from Mylan, Zenith Goldline, UDL, Novartis); olanzapine (available under the tradename ZYPREXA™, from Lilly; ziprasidone (available under the tradename GEODON™, from Pfizer); risperidone (available under the tradename RISPERDAL™, from Janssen); quetiapine fumarate (available under the tradename SEROQUEL™, from AstraZeneca); sertindole (available under the tradename SERLECT™); amisulpride (available under the tradename SOLION™, from Sanofi-Synthelabo); haloperidol (available under the tradename HALDOL™, from Ortho-McNeil); haloperidol decanoate (available under the tradename HALDOL Decanoate™; haloperidol lactate (available under the tradenames HALDOL™ and INTENSOL™); chlorpromazine (available under the tradename THORAZINE™, from SmithKline Beecham (GSK); fluphenazine (available under the tradename PROLIXIN™, from Apothecon, Copley, Schering, Teva, and American Pharmaceutical Partners, Pasadena); fluphenazine decanoate (available under the tradename PROLIXIN Decanoate™); fluphenazine enanthate (available under the tradename PROLIXIN™); fluphenazine hydrochloride (available under the tradename PROLIXIN™); thiothixene (available under the tradename NAVANE™; from Pfizer); thiothixene hydrochloride (available under the tradename NAVANE™); trifluoperazine (10-[3-(4-methyl-1-piperazinyl)propyl]-2-(trifluoromethyl)phenothiazine dihydrochloride, available under the tradename STELAZINE™, from SmithKline Beckman; perphenazine (available under the tradename TRILAFON™; from Schering); perphenazine and amitriptyline hydrochloride (available under the tradename ETRAFON TRILAFON™); thioridazine (available under the tradename MELLARIL™; from Novartis, Roxane, HiTech, Teva, and Alpharma); molindone (available under the tradename MOBAN™, from Endo); molindone hydrochloride (available under the tradename MOBAN™); loxapine (available under the tradename LOXITANE™; from Watson); loxapine hydrochloride (available under the tradename LOXITANE™); and loxapine succinate (available under the tradename LOXITANE™). Furthermore, benperidol (Glianimon™), perazine (Taxilan™) or melperone (Eunerpan™) may be used.

Other suitable antipsychotic drugs include promazine (available under the tradename SPARINE™), triflurpromazine (available under the tradename VESPRIN™) chlorprothixene (available under the tradename TARACTAN™), droperidol (available under the tradename INAPSINE™), acetophenazine (available under the tradename TINDAL™), prochlorperazine (available under the tradename COMPAZINE™), methotrimeprazine (available under the tradename NOZINAN™), pipotiazine (available under the tradename PIPOTRIL™), iloperidone, pimozide and flupenthixol.

The antipsychotic drugs listed above by Tradename may also be available from other suppliers under a different Tradename.

In one further aspect of the invention, suitable antipsychotic agents include olanzapine, risperidone, quetiapine, aripiprazole, haloperidol, clozapine, ziprasidone, talnetant and osanetant.

Mood stabilisers which may be used in the therapy of the present invention include lithium, sodium valproate/valproic acid/divalproex, carbamazepine, lamotrigine, gabapentin, topiramate, oxcarbazepine and tiagabine.

Antidepressant drugs which may be used in the therapy of the present invention include serotonin antagonists, CRF-1 antagonists, Cox-2 inhibitor/SSRI dual antagonists; dopamine/noradrenaline/serotonin triple reuptake inhibitors; NK1 antagonists; NK1 and NK2 dual antagonists; NK1/SSRI dual antagonists; NK2 antagonists; serotonin agonists (such as rauwolscine, yohimbine and metoclopramide); serotonin reuptake inhibitors (such as citalopram, escitalopram, fluoxetine, fluvoxamine, femoxetine, indalpine, zimeldine, paroxetine and sertraline); dual serotonin/noradrenaline reuptake inhibitors (such as venlafaxine, reboxetine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); 5HT3 antagonists (such as example ondansetron and granisetron); and others (such as bupropion, amineptine, radafaxine, mianserin, mirtazapine, nefazodone and trazodone).

Anxiolytics which may be used in the therapy of the present invention include V1b antagonists, $5HT_7$ antagonists and benzodiazepines such as alprazolam and lorazepam.

Drugs for extrapyramidal side effects which may be used in the therapy of the present invention include anticholinergics (such as benztropine, biperiden, procyclidine and trihexyphenidyl), antihistamines (such as diphenhydramine) and dopaminergics (such as amantadine).

Cognitive enhancers which may be used in the therapy of the present invention include example cholinesterase inhibitors (such as tacrine, donepezil, rivastigmine and galantamine), H3 antagonists and muscarinic M1 agonists (such as cevimeline).

In one embodiment, the active ingredient for use in combination with a compound of the present invention, is an atypical antipsychotic, for example clozapine, olanzapine, risperidone, quetiapine, aripirazole, ziprasidone or amisulpride.

In one embodiment, the active ingredient for use in combination with a compound of the present invention is a typical antipsychotic, for example chlorpromazine, thioridazine, mesoridazine, fluphenazine, perphenazine, prochlorperazine, trifluoperazine, thiothixine, haloperidol, thiflurpromazine, pimozide, droperidol, chlorprothixene, molindone or loxapine.

In another embodiment, the active ingredient for use in combination with a compound of the present invention is a mood stabiliser, for example lithium, sodium valproate/valproic acid/divalproex, carbamazepine, lamotrigine, gabapentin, topiramate, oxcarbazepine or tiagabine.

In another embodiment, the active ingredient for use in combination with a compound of the present invention is an antidepressant, for example a serotonin agonist (such as rauwolscine, yohimbine or metoclopramide); a serotonin reuptake inhibitor (such as citalopram, escitalopram, fluoxetine, fluvoxamine, femoxetine, indalpine, zimeldine, paroxetine or sertraline); a dual serotonin/noradrenaline reuptake inhibitor (such as venlafaxine, reboxetine, duloxetine or milnacipran); a noradrenaline reuptake inhibitors (such as reboxetine); a tricyclic antidepressants (such as amitriptyline, clomipramine, imipramine, maprotiline, nortriptyline or trimipramine); a monoamine oxidase inhibitor (such as isocarboxazide, moclobemide, phenelzine or tranylcypromine); or other (such as bupropion, amineptine, radafaxine, mianserin, mirtazapine, nefazodone or trazodone). In another embodiment, the active ingredient for use in combination with a compound of the present invention is an anxiolytic, for example a benzodiazepine such as alprazolam or lorazepam.

For use in medicine, the compounds of the present invention are usually administered as a standard pharmaceutical composition. The present invention therefore provides in a further aspect a pharmaceutical composition comprising a compound of formula (I) as hereinbefore described or a salt thereof and a pharmaceutically acceptable carrier or excipient. The pharmaceutical composition can be for use in the treatment of any of the conditions described herein. In one embodiment, the pharmaceutical composition further comprises an additional therapeutic agent, for example an active ingredient as described above or a second compound of the invention, for use in combination with a compound of the invention.

The compounds of the invention may be administered by any convenient method, for example by oral, parenteral (e.g. intravenous), buccal, sublingual, nasal, rectal or transdermal administration and the pharmaceutical compositions adapted accordingly.

The compounds of the invention which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

The composition may be in unit dose form such as a tablet, capsule or ampoule. Each dosage unit for oral administration may contain, for example, from 1 to 500 mg (and for parenteral administration contains, for example, from 0.1 to 50 mg) of a compound of the formula (I) or a salt thereof calculated as the free base. In an embodiment the unit dose for oral administration contains from 50 to 450 mg. In a further embodiment the unit dose contains from 100 to 400 mg.

In order to obtain consistency of adjunctive administration, the compositions of each of the components, or of the combination of the components is, for example, in the form of a unit dose.

The Examples set forth below are illustrative of the present invention and are not intended to limit, in any way, the scope of the present invention.

EXAMPLES

The preparation of a number of compounds of the invention are exemplified below.

In the procedures that follow, after each starting material, reference to an intermediate is typically provided. This is provided merely for assistance to the skilled chemist. The starting material may not necessarily have been prepared from the batch referred to.

Compounds of the invention and intermediates are named using ACD/Name PRO 6.02 chemical naming software (Advanced Chemistry Development Inc., Toronto, Ontario, M5H2L3, Canada).

Abbreviations
LC/MS Liquid Chromatography/Mass Spectrometry
NMR Nuclear Magnetic Resonance
THF Tetrahydrofuran
DIPEA N,N-Diisopropylethylamine
DAST Diethylaminosulfur trifluoride
DMSO Dimethylsulfoxide
DMF Dimethylformamide
DCM/MDC Dichloromethane/Methylene dichloride
MeCN Acetonitrile
MDAP Mass-directed auto-preparation
EtOAc Ethyl acetate
Min minutes
Me methyl
Et ethyl
hrs hour(s)
NBS N-bromosuccinimide Starting materials were obtained from commercial suppliers (such as Aldrich, Alfa Aesar, Apollo Scientific, Avocado, Frontier Scientific Inc. or Lancaster) and used without further purification unless otherwise stated. Flash chromatography was carried out using pre-packed Isolute Flash™ or Biotage™ silica-gel columns as the stationary phase and analytical grade solvents as the eluent unless otherwise stated.

NMR spectra were obtained at 298K, 303.2K or 300K, at the frequency stated using either a Bruker™ DPX400 or AV400 machine and run as a dilute solution of $CDCl_3$ unless otherwise stated. All NMR spectra were reference to tetramethylsilane (TMS $\delta_H$ 0, $\delta_C$ 0). All coupling constants are reported in hertz (Hz), and multiplicities are labelled s (singlet), bs, (broad singlet), d (doublet), t (triplet), q (quartet), dd (doublet of doublets), dt (doublet of triplets) and m (multiplet).

Purification

A number of the compounds were purified using a Mass Directed Auto-Purification System (MDAP) incorporating HPLC techniques and an appropriate mass spectrometer such as the Waters® ZQ mass spectrometer.

Intermediate 1: N-(3-bromo-5-cyano-2-pyridinyl)-2, 2,2-trifluoroacetamide

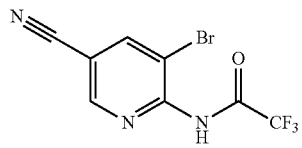 [SMILES: N#Cc1cnc(NC(=O)C(F)(F)F)c(Br)c1]

6-Amino-5-bromo-3-pyridinecarbonitrile (8.09 g, 40.9 mmol) was dissolved in DCM (190 mL), treated with DIPEA (8.56 mL, 49.0 mmol), cooled in an ice bath and treated with trifluoroacetic anhydride (6.92 mL, 49.0 mmol) dropwise. The reaction mixture was stirred for 10 minutes, allowed to warm to room temperature and stirred for 18 hours. The reaction mixture was evaporated under reduced pressure and the residue was purified by column chromatography (Biotage SP4) eluting with a gradient of 0-35% ethyl acetate and isohexane. Product containing fractions were combined and evaporated under reduced pressure to give the title compound as a brown solid (9.53 g);

m/z ($ES^+$) 294 (M), 296 (M+2).

Intermediate 2: 1,1-dimethylethyl 5-cyano-2-(trifluoromethyl)-1H-pyrrolo[2,3-b]pyridine-3-carboxylate

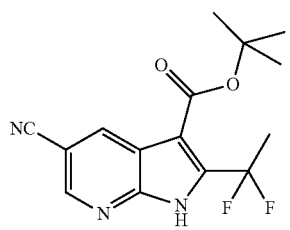 [SMILES: CC(C)(C)OC(=O)c1c(C(C)(F)F)[nH]c2ncc(C#N)cc12]

N-(3-Bromo-5-cyano-2-pyridinyl)-2,2,2-trifluoroacetamide (Intermediate 1, 9.53 g, 32.4 mmol), tert-butyl acetoacetate (10.59 mL, 64.8 mmol), copper(I) iodide (0.617 g, 3.24 mmol), L-proline (0.746 g, 6.48 mmol) and cesium carbonate (42.2 g, 130 mmol) were added together in DMSO (65 mL) and the resulting mixture was heated at 80° C. for 18 hours. The reaction mixture was allowed to cool to room temperature, diluted with ethyl acetate and washed with water and saturated ammonium chloride solution. The organic layer was separated, dried under magnesium sulfate and evaporated under reduced pressure. The residue was purified by column chromatography (Biotage SP4) eluting with a gradient of 0-30% ethyl acetate and iso-hexane. Product containing fractions were combined and evaporated under reduced pressure to give the title compound as a brown solid (2.77 g);

m/z (ES$^-$) 310 (M–1).

Intermediate 3: 5-cyano-2-(trifluoromethyl)-1H-pyrrolo[2,3-b]pyridine-3-carboxylic acid

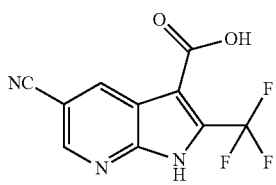 [SMILES: N#Cc1cnc2[nH]c(C(F)(F)F)c(C(=O)O)c2c1]

1,1-Dimethylethyl 5-cyano-2-(trifluoromethyl)-1H-pyrrolo[2,3-b]pyridine-3-carboxylate (Intermediate 2, 2.77 g, 8.90 mmol) was dissolved in DCM (40 mL), treated with TFA (10 mL) and the resulting mixture was stirred at room temperature for 4 hours. The solvent was removed under reduced pressure to give the title compound as a brown solid (2.49 g);

m/z (ES$^+$) 256 (M+1).

Intermediate 4: 2-(trifluoromethyl)-1H-pyrrolo[2,3-b]pyridine-5-carbonitrile

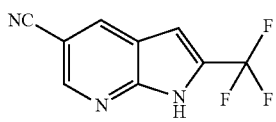 [SMILES: N#Cc1cnc2[nH]c(C(F)(F)F)cc2c1]

5-Cyano-2-(trifluoromethyl)-1H-pyrrolo[2,3-b]pyridine-3-carboxylic acid (Intermediate 3, 2.49 g, 9.76 mmol) was dissolved in water (36 mL) and N-methyl-2-pyrrolidone (48 mL). The resulting mixture was heated at 120° C. for 18 hours. The reaction mixture was allowed to cool to room temperature and diluted with water. The resulting precipitate was collected by filtration, washed with water and dried under high vacuum at 40° C. for 5 hours to give the title compound as a white solid (1.26 g);

m/z (ES$^+$) 212 (M+1).

Intermediate 5: 1-[2-(trifluoromethyl)-1H-pyrrolo[2,3-b]pyridin-5-yl]methanamine

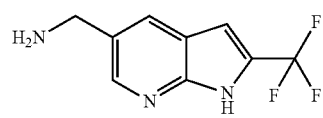 [SMILES: NCc1cnc2[nH]c(C(F)(F)F)cc2c1]

2-(Trifluoromethyl)-1H-pyrrolo[2,3-b]pyridine-5-carbonitrile (Intermediate 4, 1.48 g, 7.01 mmol) was dissolved in THF (59 mL), cooled in an ice bath and treated with a 1M solution of borane tetrahydrofuran complex (35.0 mL, 35.0 mmol) dropwise. The reaction mixture was allowed to warm to room temperature and stirred for 18 hours. Methanol (59 mL) was added dropwise and the reaction mixture was stirred for 20 minutes at room temperature. The solvent was removed under reduced pressure and the residue was dissolved in methanol (177 mL) and heated under reflux for 4 hours. The reaction mixture was allowed to cool to room temperature and passed down an SCX column (20 g) eluting with methanol, followed by 2M ammonia/methanol. Basic fractions were combined and evaporated under reduced pressure. The residue was purified by column chromatography eluting with a gradient of 0-10% 2M ammonia/methanol and DCM. Product containing fractions were combined and evaporated under reduced pressure to give the title compound as a yellow solid (1.1 g);

m/z (ES$^-$) 214 (M–1).

Intermediate 6: ethyl 6-hydroxy-4-pyrimidinecarboxylate

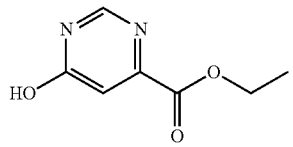

Formamidine hydrochloride (2.0 g, 45.4 mmol) and diethyl 2-butynedioate (7.23 mL, 45.4 mmol) were added together in acetonitrile (85 mL) and the resulting mixture was treated dropwise with triethylamine (6.33 mL, 45.4 mmol). The resulting mixture was heated under reflux for 4 hours. The reaction mixture was allowed to cool to room temperature, further cooled in an ice bath and the resulting solid was collected by filtration and discarded. The filtrate was evaporated under reduced pressure and the residue purified by column chromatography (Biotage SP4) eluting with a gradient of 0-100% ethyl acetate and iso-hexane. Product containing fractions were combined and evaporated under reduced pressure to give the title compound as an off white solid (0.995 g);

m/z (ES$^+$) 169 (M+1).

Intermediate 7: 6-hydroxy-4-pyrimidinecarboxamide

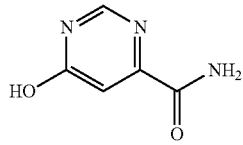

Ethyl 6-hydroxy-4-pyrimidinecarboxylate (Intermediate 6, 0.995 g, 5.92 mmol) was treated with 0.88 ammonia solution (9.95 mL, 460 mmol) at 0° C. The reaction mixture was allowed to warm to room temperature and stirred for 18 hours. The resulting solid was collected by filtration, taken up in toluene and the solvent removed under reduced pressure to give the title compound as a yellow solid (563 mg);

$^1$H NMR (400 MHz, $d_6$-DMSO): δ 12.48 (1H, bs), 8.26 (1H, s), 7.98-7.84 (2H, d), 6.80 (1H, d).

Intermediate 8: 6-chloro-4-pyrimidinecarbonitrile

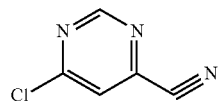

6-Hydroxy-4-pyrimidinecarboxamide (Intermediate 7, 563 mg, 4.05 mmol) was taken up in phosphorus oxychloride (3.9 mL, 41.8 mmol) and the resulting mixture was heated under reflux for 18 hours. The reaction mixture was allowed to cool to room temperature and evaporated under reduced pressure. The residue was poured into ice cooled water, neutralised with 0.88 ammonia solution and extracted with ethyl acetate (×3). The ethyl acetate layers were combined, dried under magnesium sulfate and evaporated under reduced pressure. The residue was purified by column chromatography (Biotage SP4) eluting with a gradient of 0-20% ethyl acetate and iso-hexane. Product containing fractions were combined and evaporated under reduced pressure to give the title compound as a colourless oil (346 mg);

$^1$H NMR (400 MHz, $CDCl_3$): δ 9.15 (1H, s), 7.74 (1H, s).

Intermediate 9: 6-(1,1-dimethylethyl)-4-pyrimidinol

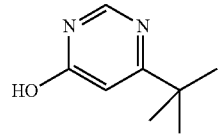

Formamidine acetate (2.172 g, 20.86 mmol) and methyl 4,4-dimethyl-3-oxopentanoate (3.0 g, 18.96 mmol) were added to a mixture of sodium methoxide (2.203 g, 40.8 mmol) in methanol (20 mL) and the resulting mixture was stirred at room temperature under argon for 18 hours. Water (5 mL) and acetic acid (2.2 mL) were added and the solvent was removed under reduced pressure. The residue was diluted with water and extracted with ethyl acetate (×3). The ethyl acetate layers were combined, dried under magnesium sulfate and evaporated under reduced pressure. The resulting solid was triturated with ethyl acetate, filtered and washed with a small volume of ethyl acetate. The solid was dried under high vacuum at 45° C. for 18 hours to give the title compound as a white solid (1.66 g);

m/z (ES$^+$) 153 (M+1).

Intermediate 10: 4-chloro-6-(1,1-dimethylethy)pyrimidine

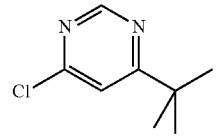

6-(1,1-Dimethylethyl)-4-pyrimidinol (Intermediate 9, 1.66 g, 10.91 mmol) was suspended in DCM (10 mL), treated with triethylamine (1.520 mL, 10.91 mmol), followed by phosphorus oxychloride (1.118 mL, 12.00 mmol) dropwise. An exotherm was observed. The resulting mixture was heated under reflux for 3 hours. LCMS indicates no desired product present and starting material remaining. The reaction mixture was allowed to cool to room temperature and evaporated under reduced pressure. The residue was treated with phosphorus oxychloride (5.08 mL, 54.5 mmol) and the resulting mixture was heated under reflux for 30 minutes. The reaction mixture was allowed to cool to room temperature, evaporated under reduced pressure and the residue was poured into 2M aqueous hydrochloric acid solution (10 mL). This solution was extracted with DCM (×2). The DCM layers were combined, dried under magnesium sulfate and evaporated under reduced pressure. The residue was purified by column chromatography (Biotage SP4) eluting with a gradient of 0-20% ethyl acetate and iso-hexane. Product containing fractions were combined and evaporated under reduced pressure to give the title compound as a colourless oil (1.17 g);

m/z (ES$^+$) 171 (M+1), 173 (M+3).

Intermediate 11: 6-ethyl-4-pyrimidinol

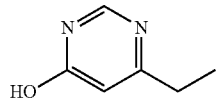

Formamidine acetate (2.64 g, 25.4 mmol) and methyl 3-oxopentanoate (3.0 g, 23.05 mmol) were added to a mixture of sodium methoxide (2.68 g, 49.6 mmol) in methanol (20 mL) and the resulting mixture was stirred at room temperature under argon for 18 hours. Water (6 mL) and acetic acid (3 mL) were added and the solvent was removed under reduced pressure. The residue was diluted with water and extracted with ethyl acetate (×3). The ethyl acetate layers were combined, dried under magnesium sulfate and evaporated under reduced pressure. The resulting solid was triturated with ethyl acetate, filtered and washed with a small volume of ethyl acetate. The solid was dried under high vacuum at 45° C. for 18 hours to give the title compound as a white solid (932 mg);

m/z (ES$^-$) 123 (M−1).

Intermediate 12: 4-chloro-6-ethylpyrimidine

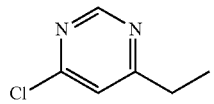

6-Ethyl-4-pyrimidinol (Intermediate 11, 0.93 g, 7.49 mmol) was treated with triethylamine (1.044 mL, 7.49 mmol) and phosphorus oxychloride (3.49 mL, 37.5 mmol) and the resulting mixture was heated under reflux for 2 hours. The reaction mixture was allowed to cool to room temperature, evaporated under reduced pressure and the residue was poured into 2M aqueous hydrochloric acid solution (10 mL). This solution was extracted with DCM (×2). The DCM layers were combined, dried under magnesium sulfate and evaporated under reduced pressure. The residue was purified by column chromatography (Biotage SP4) eluting with a gradient of 0-20% ethyl acetate and iso-hexane. Product containing fractions were combined and evaporated under reduced pressure to give the title compound as a colourless oil (552 mg);

m/z (ES$^+$) 143 (M+1), 145 (M+3).

Intermediate 13: 4-chloro-6-(methylthio)pyrimidine

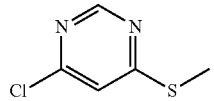

4,6-Dichloropyrimidine (2.0 g, 13.42 mmol) was dissolved in THF (10 mL), treated with sodium thiomethoxide (0.988 g, 14.10 mmol) and the resulting mixture was stirred at room temperature under argon for 18 hours. The solvent was removed under reduced pressure and the residue was partitioned between ethyl acetate and brine. The ethyl acetate layer was separated, dried under magnesium sulfate and evaporated under reduced pressure. The residue was purified by column chromatography (Biotage SP4) eluting with a gradient of 0-20% ethyl acetate and iso-hexane. Product containing fractions were combined and evaporated under reduced pressure to give the desired product as a white solid (623 mg);

$^1$H NMR (400 MHz, CDCl$_3$): δ 8.72 (1H, s), 7.21 (1H, s), 2.58 (3H, s).

Intermediate 14: methyl cyano[6-(methylthio)-4-pyrimidinyl]acetate

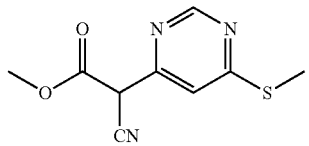

To a suspension of 60% sodium hydride in mineral oil (388 mg, 9.70 mmol) in DMSO (20 mL) was added methyl cyanoacetate (884 mg, 8.92 mmol) at room temperature. After the evolution of hydrogen had ceased, 4-chloro-6-(methylthio)pyrimidine (Intermediate 13, 623 mg, 3.88 mmol) was added. The reaction was heated at 80° C. for 5 hours. The reaction mixtures was then cooled to room temperature and quenched with ice-cooled saturated ammonium chloride solution (50 mL). The solid was filtered and washed with water. Iso-hexane (100 mL) was added to the solid and the resulting mixture was heated at 60° C. for 1 hour and then cooled to room temperature. The solid was filtered and washed with iso-hexane to give the title compound as a yellow solid (700 mg);

m/z (ES$^+$) 224 (M+1).

Intermediate 15: [6-(methylthio)-4-pyrimidinyl]acetonitrile

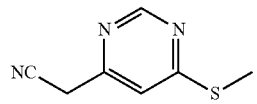

A microwave vial was charged with methyl cyano[6-(methylthio)-4-pyrimidinyl]acetate (Intermediate 14, 700 mg, 3.14 mmol), sodium chloride (1.0 g, 17.11 mmol), water (1 mL) and DMSO (19 mL). The mixture was stirred and heated at 160° C. for 50 minutes in the microwave. The reaction mixture was diluted with ethyl acetate (20 mL) and washed with brine. The organic layer was dried (sodium sulfate), filtered and concentrated under reduced pressure. The residue was dissolved in DCM (10 mL) and purified by column chromatography (Biotage SP4) eluting with a gradient of 0-100% ethyl acetate and iso-hexane. Fractions containing the suspected product were combined and concentrated under reduced pressure to give the title compound (292 mg) as a yellow oil;

m/z (ES$^+$) 166 (M+1).

Intermediate 16: [6-(methylsulfinyl)-4-pyrimidinyl]acetonitrile

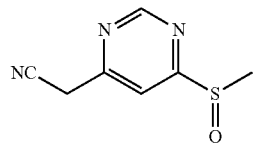

To a suspension of [6-(methylthio)-4-pyrimidinyl]acetonitrile (Intermediate 15, 292 mg, 1.767 mmol) in DCM (15 mL) was added 3-chloroperoxybenzoic acid (457 mg, 2.65 mmol) at 0° C. The reaction mixture was allowed to warm to room temperature and kept stirring for 3 hours. The reaction mixture was quenched with saturated sodium thiosulfate solution (10 mL) and vigorously stirred for 30 minutes, then treated with DCM (75 mL). The reaction mixture was partitioned between DCM and water. The organic layer was washed with saturated ammonium carbonate solution, water and brine sequentially, then dried over sodium sulfate, concentrated under pressure to give the title compound as a brown solid (150 mg);

m/z (ES$^+$) 182 (M+1).

Intermediate 17:
4-chloro-6-[1-(ethyloxy)ethenyl]pyrimidine

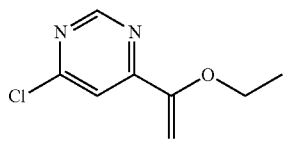

4,6-Dichloropyrimidine (1.0 g, 6.71 mmol), bis(triphenylphosphine)palladium(II) chloride (0.094 g, 0.134 mmol) and tributyl[1-(ethyloxy)ethenyl]stannane (2.449 mL, 7.25 mmol) were added together in DMF (25 mL) and the resulting mixture was heated at 80° C. under argon for 18 hours. The reaction mixture was allowed to cool to room temperature and poured into an aqueous solution of potassium fluoride (5.7 g in 57 mL water). Diethyl ether (80 mL) was added and the solid was filtered, washed with diethyl ether (×2) and discarded. The filtrate was separated and the organic layer was washed with water, dried under magnesium sulfate and evaporated under reduced pressure. The residue was purified by column chromatography (Biotage SP4) eluting with a gradient of 0-20% ethyl acetate and iso-hexane. Product containing fractions were combined and evaporated under reduced pressure to give the title compound as a white solid (564 mg);

m/z (ES$^+$) 185 (M+1), 187 (M+3).

Intermediate 18: 1-(6-chloro-4-pyrimidinyl)ethanone

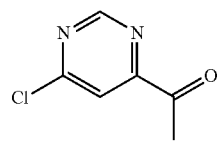

4-Chloro-6-[1-(ethyloxy)ethenyl]pyrimidine (Intermediate 17, 564 mg, 3.05 mmol) was dissolved in acetone (15 mL), treated with 2M aqueous hydrochloric acid solution (2.291 mL, 4.58 mmol) and the resulting mixture was stirred at room temperature for 2.5 hours. A further amount of 2M aqueous hydrochloric acid solution (2.291 mL, 4.58 mmol) was added and the resulting mixture was stirred at room temperature for 18 hours. The solvent was removed under reduced pressure, the residue taken up in DCM and washed with saturated sodium bicarbonate solution. The DCM layer was separated and the aqueous layer was extracted with DCM (×2). The DCM layers were separated, combined, dried under magnesium sulfate and evaporated under reduced pressure. The residue was purified by column chromatography (Biotage SP4) eluting with a gradient of 0-30% ethyl acetate and iso-hexane. Product containing fractions were combined and evaporated under reduced pressure to give the title compound as a white solid (32 mg);

$^1$H NMR (400 MHz, CDCl$_3$): δ 9.13 (1H, s), 7.97 (1H, s), 2.68 (3H, s).

Intermediate 18A:
1-(6-chloro-4-pyrimidinyl)ethanone

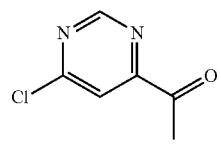

4-Chloro-6-[1-(ethyloxy)ethenyl]pyrimidine (Intermediate 17, 3.54 g, 19.17 mmol) was dissolved in acetone (177 mL), treated with 2M aqueous hydrochloric acid solution (28.8 mL, 57.5 mmol) and the resulting mixture was stirred at room temperature for 18 hours. The solvent was removed under reduced pressure. The residue was neutralised with aqueous saturated sodium bicarbonate solution and extracted with ethyl acetate (×2). The ethyl acetate layers were combined, dried under magnesium sulfate and evaporated under reduced pressure to give the title compound as a white solid (2.30 g);

$^1$H NMR (400 MHz, d$_4$-MeOD): δ 9.13 (1H, s), 7.97 (1H, d), 2.68 (3H, s).

Intermediate 19:
4-chloro-6-(1,1-difluoroethyl)pyrimidine

(Diethylamino)sulphur trifluoride (0.422 mL, 3.19 mmol) was added to DCM (16 mL), cooled to −78° C. and treated dropwise with a solution of 1-(6-chloro-4-pyrimidinyl)ethanone (Intermediate 18A, 0.5 g, 3.19 mmol) in DCM (5 mL) under argon. The resulting mixture was allowed to warm to room temperature and stirred for 18 hours.

The reaction was quenched by adding water (5 mL) and extracted with DCM (×2). The DCM layers were separated, combined, dried under magnesium sulfate and evaporated under reduced pressure. The residue was purified by column chromatography (Biotage SP4) eluting with a gradient of 0-20% ethyl acetate and iso-hexane. Product containing fractions were combined and evaporated under reduced pressure to give the title compound as a colourless oil (137 mg);

$^1$H NMR (400 MHz, CDCl$_3$): δ 9.06 (1H, s), 7.68 (1H, s), 2.05-1.96 (3H, t).

Intermediate 20: 1-(6-chloro-4-pyrimidinyl)ethanol

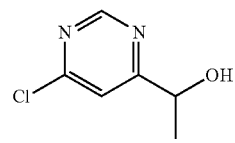

1-(6-Chloro-4-pyrimidinyl)ethanone (Intermediate 18A, 1.0 g, 6.39 mmol) was dissolved in ethanol (21 mL), treated with sodium borohydride (0.242 g, 6.39 mmol) and the resulting mixture was stirred at room temperature under argon for 2 hours. The solvent was removed under reduced pressure and the residue was diluted with water and extracted with ethyl acetate (×3). The ethyl acetate layers were combined, dried under magnesium sulfate and evaporated under reduced pressure to give the title compound as a yellow oil (808 mg);

m/z (ES$^+$) 159 (M+1), 161 (M+3).

Intermediate 21: 4-chloro-6-(1-fluoroethyl)pyrimidine

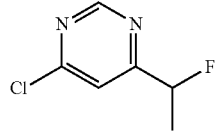

(Diethylamino)sulphur trifluoride (0.337 mL, 2.55 mmol) was added to DCM (13 mL), cooled to −78° C. and treated dropwise with a solution of 1-(6-chloro-4-pyrimidinyl)ethanol (Intermediate 20, 328 mg, 2.068 mmol) in DCM (4 mL) under argon. The resulting mixture was allowed to warm to room temperature and stirred for 4 hours. The reaction was quenched by adding water (5 mL) and extracted with DCM (×2). The DCM layers were separated, combined, dried under magnesium sulfate and evaporated under reduced pressure. The residue was purified by column chromatography (Biotage SP4) eluting with a gradient of 0-25% ethyl acetate and iso-hexane. Product containing fractions were combined and evaporated under reduced pressure to give the title compound as a colourless oil (125 mg);

$^1$H NMR (400 MHz, CDCl$_3$): δ 8.93 (1H, s), 7.56 (1H, m), 5.70-5.53 (1H, m), 1.74-1.65 (3H, dd).

Intermediate 22: 4-chloro-6-(difluoromethyl)pyrimidine

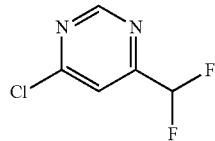

6-(Difluoromethyl)-4(1H)-pyrimidinone (0.50 g, 3.42 mmol) was treated with triethylamine (0.477 mL, 3.42 mmol) and phosphorus oxychloride (1.595 mL, 17.11 mmol) and the resulting mixture was heated under reflux for 2 hours. The reaction mixture was allowed to cool to room temperature, evaporated under reduced pressure and the residue was poured into 2M aqueous hydrochloric acid solution (5 mL). This solution was extracted with DCM (×2). The DCM layers were combined, dried under magnesium sulfate and evaporated under reduced pressure. The residue was purified by column chromatography (Biotage SP4) eluting with a gradient of 0-20% ethyl acetate and iso-hexane. Product containing fractions were combined and evaporated under reduced pressure to give the title compound as a colourless oil (117 mg);

$^1$H NMR (400 MHz, CDCl$_3$): δ 9.09 (1H, s), 7.68 (1H, s), 6.70-6.43 (1H, t).

Intermediate 23: iodomethyl benzoate

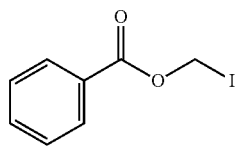 [SMILES: O=C(OCI)c1ccccc1]

Chloromethyl benzoate (2.87 g, 16.82 mmol) was dissolved in acetonitrile (20 mL) and treated portionwise with sodium iodide (5.04 g, 33.6 mmol). The resulting mixture was stirred at room temperature for 18 hours. The reaction mixture was diluted with water and extracted with ethyl acetate (×2). The ethyl acetate layers were combined, dried under magnesium sulfate and evaporated under reduced pressure. The residue was purified by column chromatography (Biotage SP4) eluting with a gradient of 0-20% ethyl acetate and iso-hexane. Product containing fractions were combined and evaporated under reduced pressure to give the title compound as a yellow oil (3.15 g);

$^1$H NMR (400 MHz, CDCl$_3$): δ 8.06-8.03 (2H, m), 7.63-7.59 (1H, m), 7.49-7.44 (2H, m), 6.16 (2H, s).

Intermediate 24: (6-chloro-4-pyrimidinyl)methyl benzoate

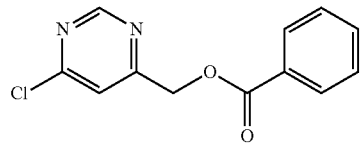 [SMILES: O=C(OCc1cc(Cl)ncn1)c1ccccc1]

Zinc (4.81 g, 73.6 mmol) was suspended in THF (6 mL), treated with 1,2-dibromoethane (0.313 mL, 3.63 mmol) and the resulting mixture was heated at 60° C. under argon for 30 minutes. The reaction mixture was allowed to cool to room temperature, treated with trimethylchlorosilane (0.120 mL, 0.938 mmol) and the resulting mixture was stirred at room temperature for 30 minutes. A solution of iodomethyl benzoate (Intermediate 23, 3.15 g, 12.02 mmol) in THF (6 mL) was added and the resulting mixture was stirred at room temperature for 1 hour. This reaction mixture was added to a solution of 4,6-dichloropyrimidine (1.075 g, 7.21 mmol) and tetrakis(triphenylphosphine)palladium(0) (0.695 g, 0.601 mmol) in THF (11 mL) and the resulting mixture was stirred at room temperature under argon for 18 hours. The reaction mixture was filtered through celite, diluted with saturated ammonium chloride solution and extracted with ethyl acetate (×2). The ethyl acetate layers were combined, dried under magnesium sulfate and evaporated under reduced pressure. The residue was purified by column chromatography (Biotage SP4) eluting with a gradient of 0-20% ethyl acetate and isohexane. Product containing fractions were combined and evaporated under reduced pressure to give the title compound as a yellow solid (394 mg);

m/z (ES$^+$) 249 (M+1).

Intermediate 25: (6-chloro-4-pyrimidinyl)methanol

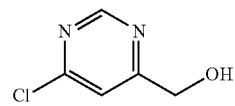

(6-Chloro-4-pyrimidinyl)methyl benzoate (Intermediate 24, 394 mg, 1.584 mmol) was dissolved in methanol (16 mL), cooled to 0° C. and treated with sodium methoxide (8.56 mg, 0.158 mmol). The resulting mixture was stirred for 4 hours. A further quantity of sodium methoxide (8.56 mg, 0.158 mmol) was added and the resulting mixture was stirrred for 18 hours. The reaction mixture was cooled to 0° C. and a further quantity of sodium methoxide (8.56 mg, 0.158 mmol) was added and the reaction mixture was stirred for 3 hours. The reaction mixture was evaporated under reduced pressure and the residue was purified by column chromatography (Biotage SP4) eluting with a gradient of 0-100% ethyl acetate and iso-hexane. Product containing fractions were combined and evaporated under reduced pressure to give the title compound as a white solid (132 mg);

$^1$H NMR (400 MHz, CDCl$_3$): δ 8.94 (1H, s), 7.47 (1H, s), 4.79 (2H, s), 2.90 (1H, bs).

Intermediate 26:
4-chloro-6-(fluoromethyl)pyrimidine

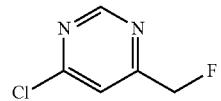

(Diethylamino)sulphur trifluoride (0.145 mL, 1.096 mmol) was added to DCM (5.5 mL), cooled to –78° C. and treated dropwise with a solution of (6-chloro-4-pyrimidinyl) methanol (Intermediate 25, 132 mg, 0.913 mmol) in DCM (2 mL) under argon. The resulting mixture was allowed to warm to room temperature and stirred for 3 hours. The reaction was quenched by adding water (5 mL) and extracted with DCM (×2). The DCM layers were separated, combined, dried under magnesium sulfate and evaporated under reduced pressure. The residue was purified by column chromatography (Biotage SP4) eluting with a gradient of 0-25% ethyl acetate and iso-hexane. Product containing fractions were combined and evaporated under reduced pressure to give the title compound as a colourless oil (40 mg);

$^1$H NMR (400 MHz, CDCl$_3$): δ 8.94 (1H, s), 7.55 (1H, s), 5.53-5.41 (2H, d).

Intermediate 27:
4-Chloro-6-ethyl-5-fluoropyrimidine

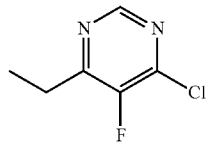

Phosphorus oxychloride (0.787 mL, 8.44 mmol) was added slowly over 10 min to a mixture of 6-ethyl-5-fluoro-pyrimidin-4(1H)-one (1 g, 7.04 mmol) (Apollo Scientific) and triethylamine (0.981 mL, 7.04 mmol) in DCM (15 mL), keeping the reaction temperature below 40° C. The mixture was then heated to reflux for 5 hrs then cooled to room temperature. The reaction mixture was then slowly poured into aqueous HCl (4M, 20 mL), keeping the temp below 20° C. The organic layer was collected and the aqueous layer was further extracted with DCM (20 mL). The organic layers were combined then washed with water (20 mL), dried (MgSO$_4$) filtered and the solvent was removed to give the title compound as a colourless oil (1 g).

$^1$H NMR (400 MHz, d$_6$-DMSO): δ 8.81 (1H, s), 2.91-2.83 (2H, m), 1.25 (2H, t).

Intermediate 28:
2-(6-Chloro-4-pyrimidinyl)-2-propanol

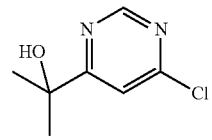

To a stirred solution of 1-(6-chloro-4-pyrimidinyl)etha-none (Intermediate 18, 500 mg, 3.19 mmol)) in THF (5 mL) was added methylmagnesium bromide (1.171 mL, 3.51 mmol), and the resulting mixture stirred under argon at 0° C. for 2 hrs. The reaction was quenched with water (25 mL) with stirring and extracted with ethyl acetate (50 mL). The combined organic layers were dried (MgSO$_4$), filtered and evaporated to dryness to afford the crude residues. Crude residues were then purified on Biotage Isolera on a pre-packed silica cartaridge (25 g) eluting with 0-20% ethyl acetate-isohexane. The appropriate fractions were combined and evaporated in vacuo to give the required product as a yellow oil (218 mg).
m/z (ES$^+$) 173 & 175 (M+1);

Intermediate 29:
4-Chloro-6-(1-fluoro-1-methylethyl)pyrimidine

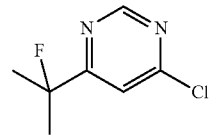

To a stirred solution of DAST (0.153 mL, 1.159 mmol) in DCM (5 mL) was added 2-(6-chloro-4-pyrimidinyl)-2-propanol (Intermediate 28, 100 mg, 0.579 mmol) dissolved in DCM (5 mL) dropwise, and the resulting mixture stirred under argon at –78° C. for 4 hrs. The reaction mixture was quenched with excess saturated sodium bicarbonate solution (50 mL) and extracted with DCM (2×20 mL). The organic layers were collected and solvent was removed gently in vacuo. Crude product in DCM was taken into the next reaction without further purification.

Intermediate 30: 4-Chloro-6-cyclopropylpyrimidine

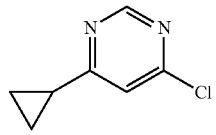

To a stirred solution of 4,6-dichloropyrimidine (200 mg, 1.342 mmol) in toluene (5.00 mL) in a 2 mL microwave vial was added potassium cyclopropyl(trifluoro)borate (219 mg, 1.477 mmol) (Frontier Scientific Inc.), di(1-adamantyl)-n-butylphosphine (14.44 mg, 0.040 mmol), palladium(II) acetate (6.03 mg, 0.027 mmol) and cesium carbonate (1312 mg, 4.03 mmol) and stirred under argon at 100° C. for 24 hrs in a microwave reactor. The reaction mixture was washed with water (50 mL) and extracted with ethyl acetate (3×20 mL). The organic layers were collected, dried (MgSO$_4$) and evaporated to dryness in vacuo to afford a crude residue. Crude residues were then purified on Biotage Isolera Four (25 g pre-packed cartridge) eluting with 0-15% ethyl acetate-isohexane. The appropriate fractions were combined and evaporated in vacuo to give the title compound as a pale yellow solid (80 mg).

m/z (ES$^+$) 155 (M+1);

1H NMR (400 MHz, d$_6$-DMSO): δ 8.81 (1H, s), 7.71 (1H, s), 2.15 (1H, m), 1.14 (2H, m), 1.08 (2H, m).

Intermediate 31: N-(4-cyano-2-methylphenyl)-2,2,2-trifluoroacetamide

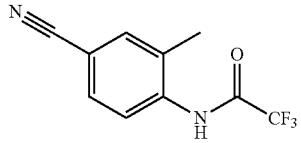 [SMILES: Cc1cc(C#N)ccc1NC(=O)C(F)(F)F]

In a round-bottomed flask 4-amino-3-methylbenzonitrile (Alfa Aesar; 10.88 g, 82 mmol), and Et$_3$N (22.95 mL, 165 mmol) were stirred in DCM (200 mL) at 0° C. TFAA (13.95 mL, 99 mmol) was added slowly via a dropping funnel and the mixture stirred at room temperature for 30 min. The reaction mixture was poured into 2M HCl (150 mL). The organic layer was then collected and then washed with a saturated solution of sodium bicarbonate (150 mL), dried (MgSO$_4$), filtered and the solvent was removed to give a dark yellow solid (19.37 g);

m/z (ES$^-$) 227 (M−1); $^1$H NMR (400 MHz, CDCl$_3$): δ 8.43 (1H, d), 7.91 (1H, bs), 7.59 (1H, dd), 7.56 (1H, s), 2.37 (3H, s).

Intermediate 32: ({5-Cyano-2-[(trifluoroacetyl)amino]phenyl}methyl)(triphenyl)phosphonium chloride

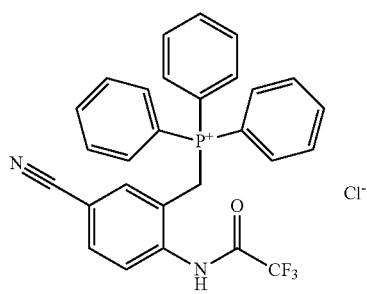 [SMILES: N#Cc1ccc(NC(=O)C(F)(F)F)c(C[P+](c2ccccc2)(c2ccccc2)c2ccccc2)c1 ; [Cl-]]

In a round-bottomed flask N-(4-cyano-2-methylphenyl)-2,2,2-trifluoroacetamide (Intermediate 31, 19.37 g, 85 mmol), sulfuryl dichloride (27.6 mL, 340 mmol) and diphenylperoxyanhydride (1.028 g, 4.24 mmol) were heated in carbon tetrachloride (210 mL) at 100° C. for 3 h. The mixture was cooled to room temperature and then the reaction mixture was poured into 2M HCl (350 mL). The organic layer was then collected and the solvent was removed to give N-[2-(chloromethyl)-4-cyanophenyl]-2,2,2-trifluoroacetamide as an orange oil, (25.54 g) which was used in the next step without further purification. This oil was added to triphenylphosphine (26.2 g, 100 mmol) and the mixture was heated in toluene (300 mL) at 110° C. for 3 h. The mixture was cooled to room temperature overnight and the precipitate was filtered and washed with small amounts of toluene and diethyl ether to give the title compound as an off-white solid (29.91 g);

m/z (ES$^+$) 489; $^1$H NMR (400 MHz, CDCl$_3$): δ 12.32 (1H, s), 7.79-7.57 (16H, m), 7.50 (1H, d), 7.38 (1H, s), 6.18 (2H, d).

Intermediate 33: 2-Trifluoromethyl-1H-indole-5-carbonitrile

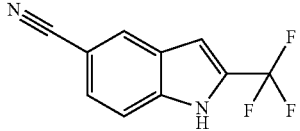 [SMILES: N#Cc1ccc2[nH]c(C(F)(F)F)cc2c1]

({5-Cyano-2-[(trifluoroacetyl)amino]phenyl}methyl)(triphenyl)phosphonium chloride (Intermediate 32, 50.41 g, 95 mmol) was heated in DMF (180 mL) at 140° C. for 7 h. The mixture was cooled to room temperature and the solvents were evaporated. This residue was combined with the corresponding residue from another experiment (wherein Intermediate 32, 7.9 g, 15.05 mmol was heated in DMF (50 mL) at 155° C. for 2 h). The combined residues were azeotroped with toluene (100 mL×2). The resulting residue was treated with diethyl ether (500 mL) and the precipitate filtered and washed with diethyl ether (100 mL). The filtrate was evaporated and the resulting orange oil (~60 g) was dissolved in DCM (200 mL) and stirred at room temperature. Iso-hexane was added until the cloudyness remained (~400 mL) and the mixtured stirred for 3 days. No precipitate was observed so the mixture was evaporated and chromatographed (Biotage 75L, eluting with DCM) to give the title compound as a colourless solid (21.7 g);

m/z (ES$^-$) 209 (M−1); $^1$H NMR (400 MHz, CDCl$_3$): δ 8.85 (1H, bs), 8.08 (1H, s), 7.57 (1H, d), 7.53 (1H, d), 7.03 (1H, s).

Intermediate 33A: 2-(trifluoromethyl)-1H-indole-5-carbonitrile

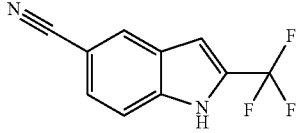 [SMILES: N#Cc1ccc2[nH]c(C(F)(F)F)cc2c1]

5-cyano-2-(trifluoromethyl)-1H-indole-3-carboxylic acid (Intermediate 36 2.09 g) was dissolved in NMP (10 mL) and H$_2$O (1 mL) was then added. The mixture was heated to 130-140° C. overnight under nitrogen. The solution was cooled to room temperature and H$_2$O (30 mL) was added and the solution stirred for 40 min. and then filtered. The cake was washed with H$_2$O. The product is then dried under vacuum at 40° C. to give the title compound (1.42 g);

$^1$H NMR (300 MHz, d6-DMSO) δ 8.26 (1H, s), 7.64 (2H, s), 7.18 (1H, s).

Intermediate 34:
[(2-Trifluoromethyl-1H-indol-5-yl)methyl]amine

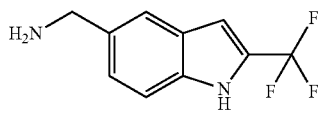

A solution of 2-trifluoromethyl-1H-indole-5-carbonitrile (Intermediate 33, 0.16 g, 0.761 mmol) in tetrahydrofuran (5 mL) cooled in an ice-water bath, was treated with a 1M solution of borane tetrahydrofuran complex (3.05 mL, 3.05 mmol) dropwise via syringe. The reaction mixture was then left to stir under argon for 18 hrs while allowing it to warm to room temperature. The reaction mixture was then quenched with methanol (10 mL) and stirred at room temperature for 10 min. The reaction mixture was then poured onto a SCX cartridge (10 g) and washed well with methanol. The desired product was then eluted using 2M ammonia/methanol solution. Evaporation to dryness gave the title compound which was used in the next step without further purification.

Intermediate 35:
N-(4-cyano-2-iodochenyl)-2,2,2-trifluoroacetamide

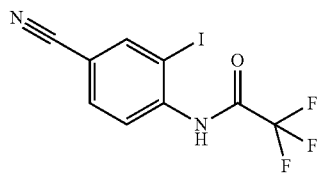 [SMILES: N#Cc1ccc(NC(=O)C(F)(F)F)c(I)c1]

To a round bottomed flask equipped with an addition funnel, thermometer, reflux condenser, and nitrogen inlet were added 4-cyano-2-iodoaniline (7.88 g), acetonitrile (24 mL), and triethylamine (4.5 mL). Trifluoroacetic anhydride (5.0 mL) was added to the suspension while maintaining the temperature below 35-40° C. The reaction was stirred for 30 min, diluted with water (31.5 mL). The slurry was held at 15-20° C. for 60 min. The product was isolated by filtration. The solid was washed with 80% aqueous acetonitrile, and dried in vacuo to give the title compound as a colorless solid (9.9 g);
$^1$H NMR (300 MHz, CDCl$_3$) δ 8.49 (1H, br s), 8.45 (1H, d), 8.15 (1H, s), 7.75 (1H, d).

Intermediate 36:
5-cyano-2-(trifluoromethyl)-1H-indole-3-carboxylic acid

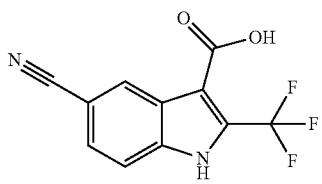 [SMILES: N#Cc1ccc2[nH]c(C(F)(F)F)c(C(=O)O)c2c1]

Cs$_2$CO$_3$ (95.82 g), CuI (3.36 g), and L-proline (9.06 g) were added to a 1L reaction vessel. The vessel was purged with N$_2$. DMSO (80 mL) was then added to the reaction vessel and the contents stirred at 18-23° C. for 10 minutes. N-(4-cyano-2-iodophenyl)-2,2,2-trifluoroacetamide (Intermediate 35, 40 g) was then added to a separate vessel and was dissolved in DMSO (40 mL). The solution of Intermediate 12 was then added to the reaction vessel over a period of at least 15 minutes as to control the CO$_2$ off-gassing. The reaction solution was stirred for 10 minutes. To the reaction mixture was then added tert-butyl acetoacetate (19.5 mL) The reaction solution was heated to 85-90° C. and stirred for 1 hr. To the reaction mixture was then added an additional 0.5 equiv. of the tert-butyl acetoacetate. The reaction was then stirred for an additional 1 hr. To the reaction mixture was then added an additional 0.5 equiv. of the tert-butyl acetoacetate and the reaction was stirred overnight. Upon completion of the reaction, the contents in the vessel were cooled to 18-23° C. Water (160 mL) was added over a period of 15 minutes while maintaining the reaction temperature below 35° C. Then isopropyl acetate (160 mL) and toluene (320 mL) was added followed by water (160 mL). The aqueous layer was drained, and the organic layer washed with saturated NH$_4$Cl solution (200 mL). The organic layer was then reduced to a minimum by vacuum distillation. DCM (160 mL) was added, and the contents were adjusted to 18-23° C. Trifluoroacetic acid (34.95 mL) was added over a period of 15 minutes. The solution was stirred overnight. The solid was filtered and washed with DCM (2×80 mL). The solid was dried in the vacuum oven to give the title compound (15.1 g);
$^1$H NMR (300 MHz, d$_6$-DMSO) δ 8.48 (1H, s), 7.67 (2H, s).

Intermediate 37: {[1,1-dimethylethyl{[2-(trifluoromethyl)-1H-pyrrolo[2,3-b]pyridin-5-yl]methyl}carbamate-d$_2$

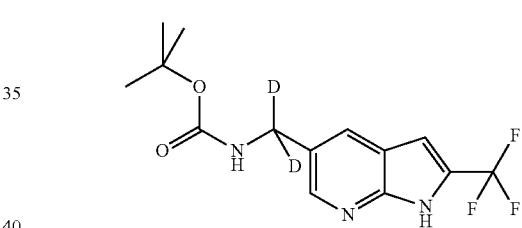

2-(Trifluoromethyl)-1H-pyrrolo[2,3-b]pyridine-5-carbonitrile (Intermediate 4, 1.6 g, 7.58 mmol) was dissolved in dry methanol (200 mL), cooled in an ice bath and treated with nickel (II) chloride hexahydrate (1.981 g, 8.34 mmol) and di-t-butyl dicarbonate (8.8 mL, 37.9 g). This was followed by the portionwise addition of sodium borodeuteride (0.952 g, 22.73 g). The reaction mixture was allowed to warm to room temperature and stirred for 18 hours. The reaction mixture was then quenched with water, filtered through celite and extracted with ethyl acetate (×3). The ethyl acetate layers were combined, dried under magnesium sulfate and evaporated under reduced pressure to give the title compound as a light brown solid (1.19 g);
m/z (ES$^-$) 316 (M−1).

Intermediate 38: 1-[2-(trifluoromethyl)-1H-pyrrolo[2,3-b]pyridin-5-yl]methanamine-d$_2$

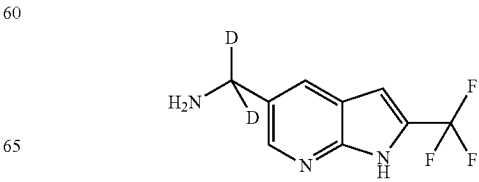

{[1,1-dimethylethyl{[2-(trifluoromethyl)-1H-pyrrolo[2,3-b]pyridin-5-yl]methyl}carbamate-d$_2$ (Intermediate 37, 1.19 g, 3.75 mmol) was dissolved in dry DCM (10 mL). This was treated with trifluoroacetic acid (2.89 mL, 37.5 mmol). The reaction mixture was stirred at room temperature for 3 hours. The solvent was removed under reduced pressure. The resulting solid was redissolved in saturated sodium bicarbonate (pH 7.5) and extracted with ethyl acetate (×3). The ethyl acetate layers were combined, dried under magnesium sulfate and evaporated under reduced pressure. The resulting solid was purified by reverse phase column chromatography eluting with a gradient of 30-80% water and acetonitrile. Product containing fractions were combined and evaporated under reduced pressure to give the title compound as a white solid (459 mg);

m/z (ES$^-$) 216 (M−1); $^1$H NMR (400 MHz, METHANOL-d$_4$) δ ppm 8.34-8.42 (m, 1H) 8.05-8.16 (m, 1H) 6.85-6.98 (m, 1H).

Intermediate 39: methyl 2-methyl-3-oxopentanoate

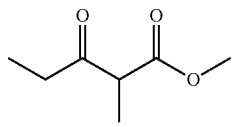

Methyl 3-oxopentanoate (6.27 ml, 50 mmol) in tetrahydrofuran (100 ml) and potassium carbonate (20.73 g, 150 mmol) was heated at reflux under argon for 3 hours, reaction mixture was cooled in an ice bath and and iodomethane (3.75 ml, 60.0 mmol) was added dropwsie. The reaction mixture was stirred at 0° C. for 6 hours, and allowed to warm to room temperature while stirring overnight. The reaction mixture was filtered through a celite and the filtrate was evaporated under reduced pressure to give the title compound as an oil (7.2 g);

$^1$H NMR (400 MHz, CDCl$_3$) δ ppm 3.66-3.80 (3H, m) 3.54 (1H, d) 2.40-2.71 (2H, m) 1.35 (3H, d), 1.08 (3H, t).

Intermediate 40: 6-ethyl-5-methyl-4-pyrimidinol

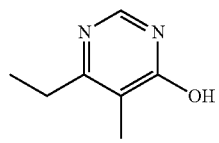

A mixture of 25% sodium methoxide in methanol (24.16 ml, 100 mmol) in methanol was stirred during the addition of formamidine acetate (5.73 g, 55.0 mmol) and methyl 2-methyl-3-oxopentanoate (Intermediate 39, 7.21 g, 50 mmol) and the reaction mixture was stirred at room temperature for 3 hours. Water (20 ml) and acetic acid (20 ml) were then added and the solution was concentrated under reduced pressure removing most of the organic solvent from the reaction mixture which was then washed with brine and extracted with ethyl acetate (×3). The ethyl acetate layers were combined, dried under magnesium sulfate and evaporated under reduced pressure. The resulting yellow residue was purified by trituration with ether, the resulting colourless solid was collected, washed with ether and dried to give the title compound as a clear solid (2.8 g);

m/z (ES$^+$) 139 (M+1).

Intermediate 41:
4-chloro-6-ethyl-5-methylpyrimidine

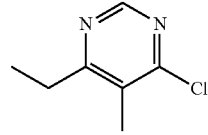

6-Ethyl-5-methyl-4(1H)-pyrimidinone (Intermediate 40, 1.382 g, 10 mmol) was added to a stirred solution of phosphorus oxychloride (4.66 ml, 50.0 mmol) and the reaction mixture was heated under reflux for 2 hours. After this time the reaction mixture was cooled to room temperature, the solvent was removed under reduced pressure. The viscous residue was dissolved in DCM and the resulting residue was poured into a stirred mixture of ice and 2M aqueous hydrochloric acid and the extracted with DCM (×3). The DCM layers were combined dried suing a hydrophobic frit and evaporated under reduced pressure to give the product, 4-chloro-6-ethyl-5-methylpyrimidine (1.32 g, 8.43 mmol) as an oil. m/z (ES$^+$) 157/159 (M+1).

$^1$H NMR (400 MHz, CDCl$_3$) δ ppm 8.74 (1H, s), 2.85 (2H, q), 2.38 (3H, s), 1.30 (3H, t).

Intermediate 42: 4-chloro-6-[1-(ethyloxy)ethenyl]-5-methylpyrimidine

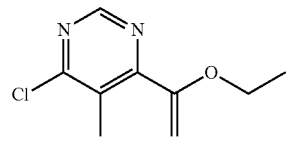

4,6-Dichloro-5-methylpyrimidine (2.0 g, 12.27 mmol), bis(triphenylphosphine)palladium(II) chloride (0.172 g, 0.245 mmol) and tributyl[1-(ethyloxy)ethenyl]stannane (4.48 ml, 13.25 mmol) were added together in N,N-dimethylformamide (DMF) (45.8 ml) and the resulting mixture was heated at 80° C. under argon for 18 hours. The reaction mixture was allowed to cool to room temperature and poured into an aqueous solution of potassium fluoride (10.4 g in 104 ml water). Diethyl ether (146 ml) was added and the solid was filtered, washed with diethyl ether (×2) and discarded. The filtrate was separated and the organic layer was washed with water, dried under magnesium sulfate and evaporated under reduced pressure. The residue was purified by SP4 Biotage column chromatography eluting with a gradient of 0-20% ethyl acetate and iso-hexane. Product containing fractions were combined and evaporated under reduced pressure to give the title compound as a yellow oil (1.49 g);

m/z (ES$^+$) 199 (M+1); $^1$H NMR (400 MHz, CDCl$_3$) δ ppm 8.79 (1H, s), 4.69 (1H, d), 4.56 (1H, d), 3.96 (2H, q), 2.43 (3H, s), 1.41 (3H, t,).

Intermediate 43:
1-(6-chloro-5-methyl-4-pyrimidinyl)ethanone

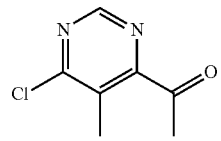

4-Chloro-6-[1-(ethyloxy)ethenyl]-5-methylpyrimidine (Intermediate 42, 1.49 g, 7.50 mmol) was dissolved in acetone (75 ml), treated with 2M aqueous hydrochloric acid solution (11.25 ml, 22.50 mmol) and the resulting mixture was stirred at room temperature for 18 hours. The solvent was removed under reduced pressure. The residue was neutralised with aqueous saturated sodium bicarbonate solution and extracted with ethyl acetate (×2). The ethyl acetate layers were combined, dried under magnesium sulfate and evaporated under reduced pressure to give the title compound as a yellow oil (947 mg);

m/z (ES$^+$) 171 (M+1); $^1$H NMR (400 MHz, CDCl$_3$) δ ppm 8.89 (1H, s), 2.69 (3H, s), 2.56 (3H, s).

Intermediate 44:
1-(6-chloro-5-methyl-4-pyrimidinyl)ethanol

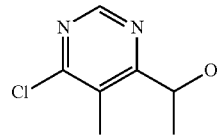

1-(6-Chloro-5-methyl-4-pyrimidinyl)ethanone (Intermediate 43, 500 mg, 2.93 mmol) was dissolved in ethanol (10.0 mL), treated with sodium borohydride (111 mg, 2.93 mmol) and the resulting mixture was stirred at room temperature under argon for 2 hours. The solvent was removed under reduced pressure and the residue was diluted with water and extracted with ethyl acetate (×3). The ethyl acetate layers were combined, dried under magnesium sulfate and evaporated under reduced pressure to give the title compound as a white crude solid (380 mg) which was used without further purification;

m/z (ES$^+$) 173 (M+1).

Intermediate 45:
4-chloro-6-(1-fluoroethyl)-5-methylpyrimidine

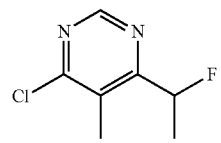

DAST (0.436 mL, 3.30 mmol) was added to dichloromethane (DCM) (11 mL), cooled to −78° C. and treated dropwise with a solution of 1-(6-chloro-5-methyl-4-pyrimidinyl)ethanol (Intermediate 44, 380 mg, 2.201 mmol) in DCM (4 mL) under argon. The resulting mixture was allowed to warm to room temperature and stirred for 4 hours. The reaction was quenched by adding water (7 ml) and extracted with DCM (×2). The DCM layers were separated, combined, dried under magnesium sulfate and evaporated under reduced pressure. The residue was purified by SP4 Biotage column chromatography eluting with a gradient of 0-20% ethyl acetate and iso-hexane. Product containing fractions were combined and evaporated under reduced pressure to give the title compound as a colourless oil (153 mg);

m/z (ES$^+$) 175 (M+1); $^1$H NMR (400 MHz, CDCl$_3$) δ ppm 8.82 (1H, s), 5.68-5.95 (1H, m), 2.33-2.58 (3H, m), 1.64-1.83 (3H, m).

Intermediate 46:
4-chloro-6-(1,1-difluoroethyl)-5-methylpyrimidine

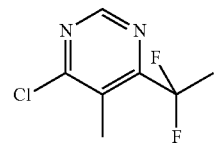

DAST (0.503 mL, 3.81 mmol) was added to DCM (12.5 mL), cooled to −78° C. and treated dropwise with a solution of 1-(6-chloro-5-methyl-4-pyrimidinyl)ethanone (Intermediate 43, 433 mg, 2.54 mmol) in DCM (4 mL) under argon. The resulting mixture was allowed to warm to room temperature and stirred for 5 hours. The reaction mixture was cooled in an ice bath, treated with DAST (0.503 mL, 3.81 mmol), allowed to warm to room temperature and stirred for 42 hours. The reaction was quenched by adding water (14 ml) and extracted with DCM (×2). The DCM layers were separated, combined, dried under magnesium sulfate and evaporated under reduced pressure. The residue was purified by SP4 Biotage column chromatography eluting with a gradient of 0-20% ethyl acetate and iso-hexane. Product containing fractions were combined and evaporated under reduced pressure to give the title compound as a yellow oil, (223 mg);

m/z (ES$^+$) 193 (M+1); $^1$H NMR (400 MHz, CDCl$_3$) δ ppm 8.82 (1H, s), 2.57 (3H, t), 1.97-2.17 (3H, m).

Intermediate 47: methyl
2-methyl-4-(methyloxy)-3-oxobutanoate

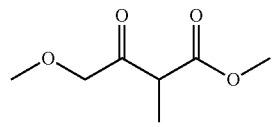

Methyl 4-(methyloxy)-3-oxobutanoate (2.0 g, 13.69 mmol) was dissolved in tetrahydrofuran (THF) (14 mL), cooled in an ice bath and treated portionwise with 60% sodium hydride in mineral oil (0.547 g, 13.69 mmol). The resulting mixture was allowed to warm to room temperature over 25 minutes and then treated dropwise with a solution of methyl iodide (0.856 mL, 13.69 mmol) in tetrahydrofuran (THF) (2 mL). The resulting mixture was stirred at room temperature for 2 hours. The solvent was removed under reduced pressure and the residue was taken up in ethyl acetate and washed with water. The organic layer was separated, dried under magnesium sulfate and evaporated under reduced pressure. The residue was purified by column chromatography (SP4, 40+M) eluting with a gradient of 0-50% ethyl acetate and iso-hexane. Product containing fractions were combined and evaporated under reduced pressure to give the title compound as a colourless oil. (1.01 g);

$^1$H NMR (400 MHz, CDCl$_3$) δ ppm 4.12 (2H, d), 3.73 (3H, s), 3.68 (1H, q), 3.41 (3H, s), 1.35 (3H, d).

Intermediate 48:
5-methyl-6-[(methyloxy)methyl]-4-pyrimidinol

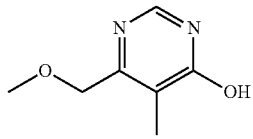

To a solution of methyl 2-methyl-4-(methyloxy)-3-oxobutanoate (Intermediate 47, 1.01 g, 6.31 mmol) in methanol (7 mL) was added formamidine acetate (0.722 g, 6.94 mmol) and 25% sodium methoxide in MeOH (3.0 mL, 6.31 mmol) and the resulting mixture was heated under reflux for 2 hours, cooled to room temperature and left to stand overnight. The reaction mixture was evaporated under reduced pressure. The residue was diluted with water, adjusted to pH 7 using aqueous 2M HCl solution and extracted with chloroform (×3). The chloroform layers were combined, dried under magnesium sulfate and evaporated under reduced pressure to give the title compound as a white solid (597 mg);

m/z (ES$^+$) 155 (M+1); $^1$H NMR (400 MHz, CHLOROFORM-d) δ ppm 12.9 (1H, br s), 8.13 (1H, s), 4.43 (2H, s), 3.47 (3H, s), 2.14 (3H, s).

Intermediate 49:
4-chloro-5-methyl-6-[(methyloxy)methyl]pyrimidine

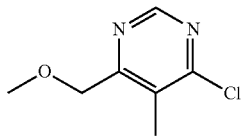

5-Methyl-6-[(methyloxy)methyl]-4-pyrimidinol (Intermediate 48, 2.10 g, 13.62 mmol) was dissolved in DCM (20 ml), treated with phosphorus oxychloride (12.04 ml, 129 mmol) and the resulting mixture was heated under reflux for 3 hours, allowed to cool to room temperature and left to stand overnight. The solvent was removed under reduced pressure, the residue taken up in ice water and the pH was adjusted to 7 using aqueous 2M sodium hydroxide solution. The mixture was extracted with chloroform (×3) and the chloroform layers were separated, combined, dried under magnesium sulfate and evaporated under reduced pressure. The residue was purified by SP4 Biotage column chromatography eluting with a gradient of 0-50% ethyl acetate and iso-hexane. Product containing fractions were combined and evaporated under reduced pressure to give the title compound as a yellow oil (2.14 g);

m/z (ES$^+$) 173 (M+1); $^1$H NMR (400 MHz, CDCl$_3$) δ ppm 8.81 (1H, s), 4.60 (2H, s), 3.47 (3H, s), 2.41 (3H, s).

Intermediate 50:
(6-chloro-5-methyl-4-pyrimidinyl)methanol

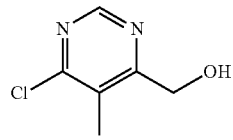

4-Chloro-5-methyl-6-[(methyloxy)methyl]pyrimidine (Intermediate 49, 2.14 g, 12.40 mmol) was dissolved in DCM (105 ml), cooled in an ice bath and treated with 1M boron tribromide in DCM (13.64 ml, 13.64 mmol). The resulting mixture was stirred for 1 hour, allowed to warm to room temperature and stirred for 1 hour. The reaction was quenched by adding water and diluted with DCM. The DCM layer was separated, dried under magnesium sulfate and evaporated under reduced pressure to give the title compound as a yellow solid (1.70 g) m/z (ES$^+$) 159 (M+1), title compound is 49% pure by LCMS. Also contains (6-bromo-5-methyl-4-pyrimidinyl)methanol, m/z (ES$^+$) 203, 205 (M+1) (49% by LCMS)

Intermediate 51:
4-chloro-6-(fluoromethyl)-5-methylpyrimidine

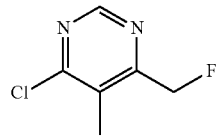

DAST (1.5 mL, 11.35 mmol) was added to dichloromethane (DCM) (64 mL), cooled to −78° C. and treated dropwise with a solution of (6-chloro-5-methyl-4-pyrimidinyl)methanol (Intermediate 50, 1.70 g, 10.72 mmol) in DCM (24 mL) under argon. The resulting mixture was allowed to warm to room temperature and stirred for 3 hours. The reaction was quenched by adding water (45 ml) and extracted with DCM (×2). The DCM layers were separated, combined, dried under magnesium sulfate and evaporated under reduced pressure. The residue was purified by column chromatography (SP4, 40+M) eluting with a gradient of 0-50% ethyl acetate and iso-hexane. Product containing fractions were combined and evaporated under reduced pressure to give the title compound as a yellow oil (1.29 g) m/z (ES$^+$) 161 (M+1), title compound is 42% pure by LCMS. Also contains 4-bromo-6-(fluoromethyl)-5-methylpyrimidine, m/z (ES$^+$) 205, 207 (M+1) (44% by LCMS)

Intermediate 52:
4-chloro-6-cyclopropyl-5-methylpyrimidine

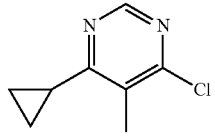

To a stirred solution of 4,6-dichloro-5-methylpyrimidine (1 g, 6.13 mmol) in toluene (38.2 ml) was added potassium cyclopropyl(trifluoro)borate (0.999 g, 6.75 mmol), di(1-adamantyl)-n-butylphosphine (0.066 g, 0.184 mmol), palladium (II) acetate (0.028 g, 0.123 mmol), cesium carbonate (6.00 g, 18.40 mmol) and the reaction mixture stirred under argon at 100° C. for 24 hours. The reaction mixture was washed with water and extracted with ethyl acetate (3×25 mL). The organic layers were collected, dried under magnesium sulphate and evaporated under reduced pressure. Crude residues were purified by Si SP4 column chromatography eluting with a gradient of 0-15% ethyl acetate-isohexane. Product containing fractions were combined and evaporated under reduced pressure to give the title compound as a white solid (491 mg);

m/z (ES+) 169 (M+1); $^1$H NMR (400 MHz, CDCl$_3$) δ ppm 8.59 (1H, s), 2.49 (3H, s), 2.03-2.22 (1H, m), 1.16-1.28 (2H, m), 1.11 (2H, dt).

Example 1

6-(Trifluoromethyl)-N-{[2-(trifluoromethyl)-1H-pyrrolo[2,3-b]pyridin-5-yl]methyl}-4-pyrimidinamine

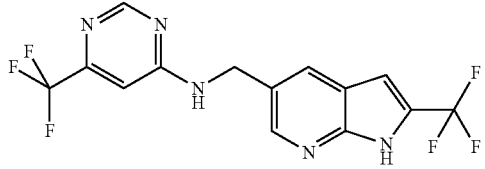 [SMILES: FC(F)(F)c1cc(NCc2cnc3[nH]c(C(F)(F)F)cc3c2)ncn1]

1-[2-(Trifluoromethyl)-1H-pyrrolo[2,3-b]pyridin-5-yl]methanamine (Intermediate 5, 130 mg, 0.604 mmol), 4-chloro-6-(trifluoromethyl)pyrimidine (165 mg, 0.906 mmol) and DIPEA (0.211 mL, 1.208 mmol) in N-methyl-2-pyrrolidone (2 mL) were stirred at 150° C. for 1 hour in the microwave. The reaction mixture was diluted with ethyl acetate (25 mL) and washed with water (10 mL), brine (10 mL), water (10 mL) and brine (10 mL). The organic layer was dried (sodium sulfate), filtered and concentrated under reduced pressure to give a brown oil. This oil was dissolved in a mixture of acetonitrile and DMSO (1:1) (2.7 mL) and purified by MDAP (3 injections). Fractions containing the suspected product were combined and concentrated under reduced pressure to give the title compound as a pale brown solid (72 mg);

m/z (ES+) 362 (M+1); $^1$H NMR (400 MHz, d$_4$-MeOD): δ 8.56 (1H, bs), 8.43 (1H, d), 8.13 (1H, d), 6.93 (1H, d), 6.87 (1H, bs), 4.79 (2H, bs).

Example 2

6-(1-Methylethyl)-N-{[2-(trifluoromethyl)-1H-pyrrolo[2,3-b]pyridin-5-yl]methyl}-4-pyrimidinamine

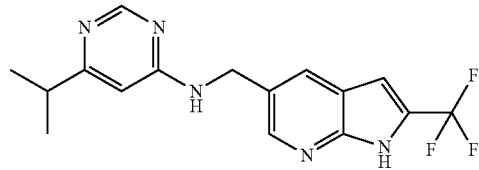 [SMILES: CC(C)c1cc(NCc2cnc3[nH]c(C(F)(F)F)cc3c2)ncn1]

1-[2-(Trifluoromethyl)-1H-pyrrolo[2,3-b]pyridin-5-yl]methanamine (Intermediate 5, 75 mg, 0.349 mmol), 4-chloro-6-(1-methylethyl)pyrimidine (54.6 mg, 0.349 mmol) and DIPEA (0.122 mL, 0.697 mmol) in N-methyl-2-pyrrolidone (1 mL) were stirred in a microwave reactor at 120° C. for 1 hour. The reaction mixture was diluted with ethyl acetate (20 mL) and washed with water (10 mL), brine (10 mL), water (10 mL) and brine (10 mL). The organic layer was dried (sodium sulfate), filtered and concentrated under reduced pressure. This solid was dissolved in a mixture of acetonitrile and DMSO (1:1) (0.9 mL) and purified by MDAP (2 injections). Fractions containing pure product were combined and concentrated under reduced pressure to give the title compound as a yellow oil (28 mg);

m/z (ES+) 336 (M+1); $^1$H NMR (400 MHz, d$_4$-MeOD): δ 8.45-8.42 (2H, m), 8.24 (1H, bs), 8.14 (1H, d), 6.93 (1H, d), 6.48 (1H, bs), 4.77 (2H, bs), 2.86-2.79 (1H, m), 1.26-1.24 (6H, d).

Example 3

6-({[2-(Trifluoromethyl)-1H-pyrrolo[2,3-b]pyridin-5-yl]methyl}amino)-4-pyrimidinecarbonitrile

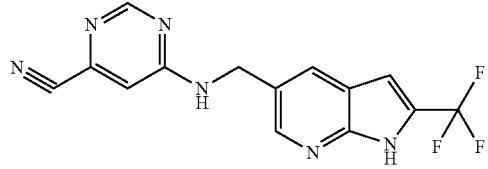 [SMILES: N#Cc1cc(NCc2cnc3[nH]c(C(F)(F)F)cc3c2)ncn1]

1-[2-(Trifluoromethyl)-1H-pyrrolo[2,3-b]pyridin-5-yl]methanamine (Intermediate 5, 100 mg, 0.465 mmol), 6-chloro-4-pyrimidinecarbonitrile (Intermediate 8, 97 mg, 0.697 mmol) and DIPEA (0.162 mL, 0.929 mmol) were added together in N-methyl-2-pyrrolidone (2 mL) and the resulting mixture was heated at 100° C. for 2 hours and allowed to cool to room temperature. The reaction mixture was diluted with ethyl acetate and washed with water and brine. The organic layer was separated, dried under magnesium sulfate and evaporated under reduced pressure. The residue was purified by MDAP. Product containing fractions were combined and evaporated under reduced pressure. The resulting solid was dried under high vacuum at 45° C. for 18 hours to give the title compound as an off-white solid (32 mg);

m/z (ES+) 319 (M+1); $^1$H NMR (400 MHz, d$_6$-DMSO): δ 12.90 (1H, bs), 8.65-8.62 (1H, m), 8.55 (1H, bs), 8.45 (1H, bs), 8.08 (1H, bs), 7.05 (2H, bs), 4.71-4.69 (2H, d).

Example 4

6-(1,1-Dimethylethyl)-N-{[2-(trifluoromethyl)-1H-pyrrolo[2,3-b]pyridin-5-yl]methyl}-4-pyrimidinamine

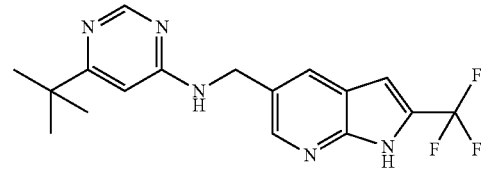 [SMILES: CC(C)(C)c1cc(NCc2cnc3[nH]c(C(F)(F)F)cc3c2)ncn1]

1-[2-(Trifluoromethyl)-1H-pyrrolo[2,3-b]pyridin-5-yl]methanamine (Intermediate 5, 75 mg, 0.349 mmol), 4-chloro-6-(1,1-dimethylethyl)pyrimidine (Intermediate 10, 89 mg, 0.523 mmol) and DIPEA (0.122 mL, 0.697 mmol) were added together in N-methyl-2-pyrrolidone (2 mL) and the resulting mixture was heated at 120° C. for 2 hours and allowed to cool to room temperature. The reaction mixture was diluted with ethyl acetate and washed with water and brine. The organic layer was separated, dried under magnesium sulfate and evaporated under reduced pressure. The residue was purified by MDAP. Product containing fractions were combined and evaporated under reduced pressure. The resulting solid was dried under high vacuum at 45° C. for 18 hours to give the title compound as a white solid (17 mg);

m/z (ES⁺) 350 (M+1); ¹H NMR (400 MHz, d₆-DMSO): δ 12.87 (1H, bs), 8.43 (1H, d), 8.39 (1H, d), 8.16 (1H, s), 8.05 (1H, d), 7.81-7.78 (1H, m), 7.03 (1H, d), 6.47 (1H, d), 4.63-4.61 (2H, d), 1.19 (9H, s).

Example 5

6-Ethyl-N-{[2-(trifluoromethyl)-1H-pyrrolo[2,3-b]pyridin-5-yl]methyl}-4-pyrimidinamine

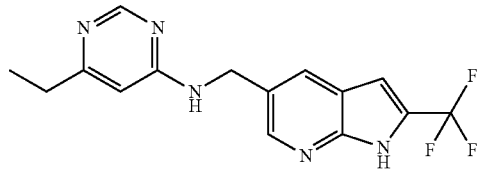 [SMILES: CCc1cc(NCc2cnc3[nH]c(C(F)(F)F)cc3c2)ncn1]

1-[2-(Trifluoromethyl)-1H-pyrrolo[2,3-b]pyridin-5-yl]methanamine (Intermediate 5, 75 mg, 0.349 mmol), 4-chloro-6-ethylpyrimidine (Intermediate 12, 49.7 mg, 0.349 mmol) and DIPEA (0.122 mL, 0.697 mmol) in N-methyl-2-pyrrolidone (1 mL) were stirred in a microwave reactor at 120° C. for 1 hour. The reaction mixture was diluted with ethyl acetate (20 mL) and washed with water (10 mL), brine (10 mL), water (10 mL) and brine (10 mL). The organic layer was dried (sodium sulfate), filtered and concentrated under reduced pressure. This solid was dissolved in a mixture of acetonitrile and DMSO (1:1) (0.9 mL) and purified by MDAP (2 injections). Fractions containing pure product were combined and concentrated under reduced pressure to give the title compound as a yellow oil (21 mg);

m/z (ES⁺) 322 (M+1); ¹H NMR (400 MHz, d₄-MeOD): δ 8.49 (1H, bs), 8.43 (1H, d), 8.28 (1H, s), 8.14-8.12 (1H, d), 6.92 (1H, d), 6.52 (1H, bs), 4.79 (2H, bs), 2.67-2.60 (2H, m), 1.27-1.23 (3H, m).

The hydrochloride salt of the title compound was also obtained.

Example 6

[6-({[2-(Trifluoromethyl)-1H-pyrrolo[2,3-b]pyridin-5-yl]methyl}amino)-4-pyrimidinyl]acetonitrile

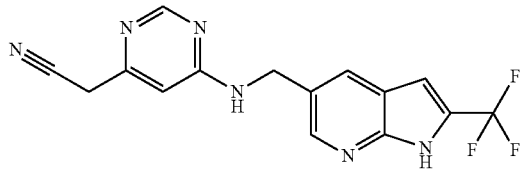 [SMILES: N#CCc1cc(NCc2cnc3[nH]c(C(F)(F)F)cc3c2)ncn1]

A mixture of [6-(methylsulfinyl)-4-pyrimidinyl]acetonitrile (Intermediate 16, 150 mg, 0.828 mmol) and 1-[2-(trifluoromethyl)-1H-pyrrolo[2,3-b]pyridin-5-yl]methanamine (Intermediate 5, 178 mg, 0.828 mmol) in isopropanol (7 mL) was stirred and heated at 80° C. overnight. The reaction mixture was cooled to room temperature and condensed. This solid was dissolved in a mixture of acetonitrile and DMSO (1:1) (2.7 mL) and purified by MDAP (3 injections). Fractions containing the suspected product were combined and concentrated under reduced pressure. The solid was dissolved in a mixture of acetonitrile and DMSO (1:1) (1.8 mL) and purified again by MDAP (2 injections). Fractions containing the suspected product were combined and concentrated under reduced pressure to give the title compound as a solid (23 mg);

m/z (ES⁺) 333 (M+1); ¹H NMR (400 MHz, d₄-MeOD): δ 8.42-8.40 (2H, m), 8.11 (1H, d), 6.92-6.91 (1H, m), 6.63 (1H, d), 4.73 (2H, bs), 3.35 (2H, bs).

Example 7

1-[6-({[2-(Trifluoromethyl)-1H-pyrrolo[2,3-b]pyridin-5-yl]methyl}amino)-4-pyrimidinyl]ethanone

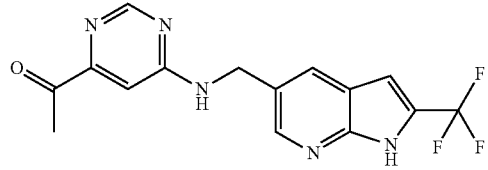 [SMILES: CC(=O)c1cc(NCc2cnc3[nH]c(C(F)(F)F)cc3c2)ncn1]

1-[2-(Trifluoromethyl)-1H-pyrrolo[2,3-b]pyridin-5-yl]methanamine (Intermediate 5, 32 mg, 0.149 mmol), 1-(6-chloro-4-pyrimidinyl)ethanone (Intermediate 18, 34.9 mg, 0.223 mmol) and DIPEA (0.052 mL, 0.297 mmol) were added together in N-methyl-2-pyrrolidone (1 mL) and the resulting mixture was stirred at room temperature for 7 hours. The reaction mixture was diluted with ethyl acetate and washed with water and brine. The organic layer was separated, dried under magnesium sulfate and evaporated under reduced pressure. The residue was purified by MDAP. Product containing fractions were combined and evaporated under reduced pressure. The resulting solid was dried under high vacuum at 45° C. for 18 hours to give the title compound as a white solid (4 mg);

m/z (ES⁺) 336 (M+1); ¹H NMR (400 MHz, d₆-DMSO): δ 12.82 (1H, bs), 8.60 (1H, bs), 8.43 (1H, d), 8.37-8.34 (1H, m), 8.05 (1H, d), 7.03 (1H, bs), 6.99 (1H, bs), 4.70 (2H, m), 2.52 (3H, s).

Example 8

6-(1,1-Difluoroethyl)-N-{[2-(trifluoromethyl)-1H-pyrrolo[2,3-b]pyridin-5-yl]methyl}-4-pyrimidinamine

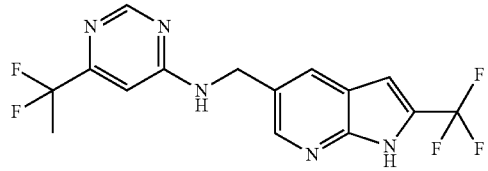 [SMILES: CC(F)(F)c1cc(NCc2cnc3[nH]c(C(F)(F)F)cc3c2)ncn1]

1-[2-(Trifluoromethyl)-1H-pyrrolo[2,3-b]pyridin-5-yl]methanamine (Intermediate 5, 110 mg, 0.511 mmol), 4-chloro-6-(1,1-difluoroethyl)pyrimidine (Intermediate 19, 137 mg, 0.767 mmol) and DIPEA (0.179 mL, 1.022 mmol) were added together in N-methyl-2-pyrrolidone (3 mL) and the resulting mixture was stirred at room temperature for 2 hours. The reaction mixture was diluted with ethyl acetate and washed with water and brine. The organic layer was separated, dried under magnesium sulfate and evaporated under reduced pressure.

The residue was purified by MDAP. Product containing fractions were combined and evaporated under reduced pressure. The resulting solid was dried under high vacuum at 45° C. for 18 hours to give the title compound as a white solid (29 mg);

m/z (ES+) 358 (M+1); $^1$H NMR (400 MHz, d$_6$-DMSO): δ 12.85 (1H, bs), 8.52 (1H, bs), 8.44 (1H, d), 8.34-8.31 (1H, m), 8.07 (1H, d), 7.04 (1H, d), 6.77 (1H, bs), 4.71-4.69 (2H, m), 1.92-1.83 (3H, t).

6-(1-fluoroethyl)-N-{[2-(trifluoromethyl)-1H-pyrrolo[2,3-b]pyridin-5-yl]methyl}-4-pyrimidinamine-d$_2$ the deuterated analogue of Example 8 was also prepared:

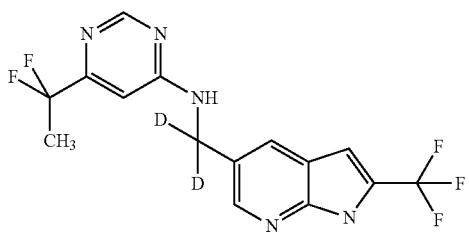 [SMILES: [2H]C([2H])(Nc1cc(C(C)(F)F)ncn1)c1cnc2[nH]c(C(F)(F)F)cc2c1]

1-[2-(Trifluoromethyl)-1H-pyrrolo[2,3-b]pyridin-5-yl] methanamine-d$_2$ (Intermediate 38, 50 mg, 0.230 mmol), 4-chloro-6-(1,1-difluoroethyl)pyrimidine (Intermediate 19, 61.7 mg, 0.345 mmol) and DIPEA (0.080 mL, 0.460 mmol) were added together in dry N-methyl-2-pyrrolidone (5 mL) and the resulting mixture was stirred at room temperature for over the weekend. The reaction mixture was diluted with ethyl acetate and washed with water and brine. The organic layer was separated, dried under magnesium sulfate and evaporated under reduced pressure. The residue was purified by MDAP. Product containing fractions were combined and evaporated under reduced pressure. The resulting solid was dried under high vacuum at 45° C. for 18 hours to give the title compound as a light yellow solid (40 mg).

m/z (ES+) 360; $^1$H NMR (400 MHz, DMSO-d$_6$) δ ppm 12.71-13.01 (1H, m), 8.48-8.60 (1H, m), 8.39-8.48 (1H, m), 8.23-8.34 (1H, m), 8.07 (1H, d), 7.00-7.14 (1H, m), 6.68-6.86 (1H, m), 1.87 (3H, t).

Example 9

6-(1-Fluoroethyl)-N-{[2-(trifluoromethyl)-1H-pyrrolo[2,3-b]pyridin-5-yl]methyl}-4-pyrimidinamine

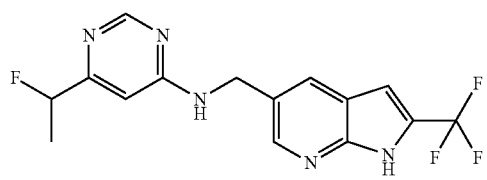 [SMILES: CC(F)c1cc(NCc2cnc3[nH]c(C(F)(F)F)cc3c2)ncn1]

1-[2-(Trifluoromethyl)-1H-pyrrolo[2,3-b]pyridin-5-yl] methanamine (Intermediate 5, 112 mg, 0.521 mmol), 4-chloro-6-(1-fluoroethyl)pyrimidine (Intermediate 21, 125 mg, 0.781 mmol) and DIPEA (0.182 mL, 1.041 mmol) were added together in N-methyl-2-pyrrolidone (3 mL) and the resulting mixture was stirred at room temperature for 1 hour. The reaction mixture was heated at 100° C. for 1 hour and allowed to cool to room temperature. The reaction mixture was diluted with ethyl acetate and washed with water and brine. The organic layer was separated, dried under magnesium sulfate and evaporated under reduced pressure. The residue was purified by MDAP. Product containing fractions were combined and evaporated under reduced pressure. The resulting solid was dried under high vacuum at 45° C. for 18 hours to give the title compound as a white solid (25 mg);

m/z (ES+) 340 (M+1); $^1$H NMR (400 MHz, d$_6$-DMSO): δ 12.82 (1H, bs), 8.44 (1H, d), 8.41 (1H, bs), 8.12-8.08 (1H, m), 8.06 (1H, d), 7.04 (1H, d), 6.58 (1H, bs), 5.53-5.36 (1H, m), 4.66 (2H, bs), 1.55-1.47 (3H, dd).

Example 10

6-(Difluoromethyl)-N-{[2-(trifluoromethyl)-1H-pyrrolo[2,3-b]pyridin-5-yl]methyl}-4-pyrimidinamine

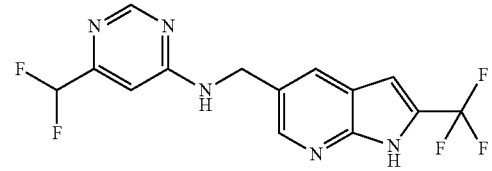 [SMILES: FC(F)c1cc(NCc2cnc3[nH]c(C(F)(F)F)cc3c2)ncn1]

1-[2-(Trifluoromethyl)-1H-pyrrolo[2,3-b]pyridin-5-yl] methanamine (Intermediate 5, 100 mg, 0.465 mmol), 4-chloro-6-(difluoromethyl)pyrimidine (Intermediate 22, 117 mg, 0.711 mmol) and DIPEA (0.162 mL, 0.929 mmol) were added together in N-methyl-2-pyrrolidone (3 mL) and the resulting mixture was stirred at room temperature for 2 hours. The reaction mixture was diluted with ethyl acetate and washed with water and brine. The organic layer was separated, dried under magnesium sulfate and evaporated under reduced pressure. The residue was purified by MDAP. Product containing fractions were combined and evaporated under reduced pressure. The resulting solid was dried under high vacuum at 45° C. for 18 hours to give the title compound as a white solid (30 mg);

m/z (ES+) 344 (M+1); $^1$H NMR (400 MHz, d$_6$-DMSO): δ 12.82 (1H, bs), 8.53 (1H, bs), 8.45 (1H, d), 8.37-8.34 (1H, m), 8.07 (1H, d), 7.04 (1H, d), 6.86-6.59 (1H, m), 6.77 (1H, bs), 4.71-4.69 (2H, d).

Example 11

6-(Fluoromethyl)-N-{[2-(trifluoromethyl)-1H-pyrrolo[2,3-b]pyridin-5-yl]methyl}-4-pyrimidinamine

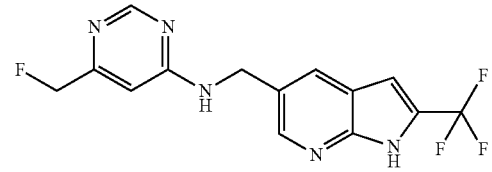

1-[2-(Trifluoromethyl)-1H-pyrrolo[2,3-b]pyridin-5-yl] methanamine (Intermediate 5, 65 mg, 0.211 mmol), 4-chloro-6-(fluoromethyl)pyrimidine (Intermediate 26, 40 mg, 0.232 mmol) and DIPEA (0.074 mL, 0.423 mmol) were added together in N-methyl-2-pyrrolidone (2 mL) and the resulting mixture was stirred at room temperature for 3 hours. The reaction mixture was heated at 100° C. for 3 hours, allowed to cool to room temperature and diluted with ethyl acetate and washed with water and brine. The organic layer was separated, dried under magnesium sulfate and evaporated under reduced pressure. The residue was purified by MDAP. Product containing fractions were combined and evaporated under reduced pressure. The resulting solid was dried under high vacuum at 45° C. for 18 hours to give the title compound as a white solid (6 mg);

m/z (ES$^+$) 326 (M+1); $^1$H NMR (400 MHz, d$_6$-DMSO): δ 12.83 (1H, bs), 8.44 (1H, d), 8.41 (1H, bs), 8.22 (1H, bs), 8.12-8.08 (1H, m), 8.05 (1H, d), 7.04 (1H, d), 6.57 (1H, bs), 5.32-5.20 (2H, d), 4.69-4.65 (2H, bs).

Example 12

6-(Trifluoromethyl)-N-{[2-(trifluoromethyl)-1H-indol-5-yl]methyl}-4-pyrimidinamine

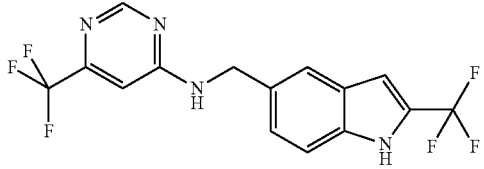 [SMILES: FC(F)(F)c1cc(NCc2ccc3[nH]c(C(F)(F)F)cc3c2)ncn1]

{[2-(Trifluoromethyl)-1H-indol-5-yl]methyl}amine (Intermediate 34, 100 mg, 0.467 mmol), 4-chloro-6-(trifluoromethyl)pyrimidine (Intermediate 26, 128 mg, 0.700 mmol) and potassium carbonate (142 mg, 1.027 mmol) were dissolved in DMSO (1 mL). The reaction mixture was stirred in the microwave for 1 hour at 130° C. The LC/MS showed product. The reaction mixture was poured into water and the product was extracted with ethyl acetate. Traces of water were removed with a phase separator. The solvent was removed under reduced pressure. Purification was done by MDAP. The most pure fractions were combined and diluted with DCM and washed with aqueous sodium bicarbonate. Traces of water were removed with a phase separator. The solvent was removed under reduced pressure to give the title compound (20 mg);

m/z (ES$^+$) 361 (M+1); $^1$H NMR (400 MHz, d$_6$-DMSO): δ 12.23 (1H, bs), 8.60 (1H, bs), 8.50 (1H, m), 7.63 (1H, bs), 7.49-7.43 (1H, d), 7.30-7.27 (1H, d), 7.00 (1H, m), 6.91 (1H, s), 4.70 (2H, d).

Example 13

6-Chloro-N-{[2-(trifluoromethyl)-1H-indol-5-yl]methyl}-4-pyrimidinamine

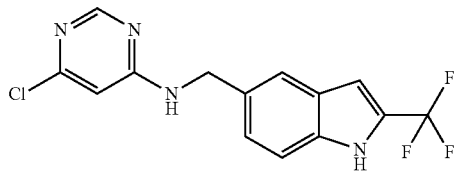 [SMILES: FC(F)(F)c1cc2cc(CNc3cc(Cl)ncn3)ccc2[nH]1]

{[2-(Trifluoromethyl)-1H-indol-5-yl]methyl}amine (Intermediate 34, 600 mg, 2.394 mmol), 4,6-dichloropyrimidine (357 mg, 2.394 mmol) and potassium carbonate (993 mg, 7.18 mmol) were added to DMSO (13 mL). The reaction mixture was heated in the microwave for 1.5 hours at 140° C. The LC/MS showed product. The reaction mixture was poured into water and extracted with ethyl acetate. Traces of water were removed with a phase separator and the solvent removed under reduced pressure to give the title compound (580 mg);

m/z (ES$^+$) 327 (M+1), 329 (M+3); $^1$H NMR (400 MHz, d$_6$-DMSO): δ 12.22 (1H, bs), 8.30 (1H, bs), 8.20 (1H, m), 7.61 (1H, bs), 7.43 (1H, d), 7.27 (1H, d), 7.00 (1H, bs), 6.57 (1H, m), 4.62-4.48 (2H, m).

Example 14

6-Cyclopropyl-N-{[2-(trifluoromethyl)-1H-pyrrolo[2,3-b]pyridin-5-yl]methyl}-4-pyrimidinamine

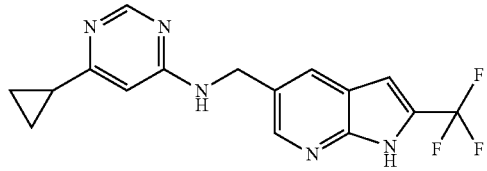 [SMILES: FC(F)(F)c1cc2cc(CNc3cc(C4CC4)ncn3)cnc2[nH]1]

To a stirred solution of 4-chloro-6-cyclopropylpyrimidine (Intermediate 30, 75 mg, 0.485 mmol) in NMP (2 mL) in a 2 mL microwave vial was added and 1-[2-(trifluoromethyl)-1H-pyrrolo[2,3-b]pyridin-5-yl]methanamine (Intermediate 5, 104 mg, 0.485 mmol), DIPEA (0.169 mL, 0.970 mmol), vial de-gassed with argon and heated in a microwave at 120° C. for 2 hrs. The reaction mixture was poured into water (25 mL) and extracted with ethyl acetate (2×20 mL). The organic layers were combined, dried (MgSO$_4$) and evaporated to dryness in vacuo to afford the crude residues. Resulting residues were then purified via MDAP. The appropriate fractions were collected, residue washed with methanol and evaporated to dryness in vacuo to give the title compound as a brown solid (40 mg).

m/z (ES$^+$) 332 (M+1);

$^1$H NMR (400 MHz, d$_6$-DMSO): δ 12.85 (1H, brs), 8.43 (1H, d), 8.25 (1H, s), 8.04 (1H, d), 7.74 (3H, t), 7.03 (1H, d), 6.42 (1H, d), 4.61 (2H, d), 1.86-1.78 (1H, m), 0.90-0.83 (4H, m).

6-Cyclopropyl-N-{[2-(trifluoromethyl)-1H-pyrrolo[2,3-b]pyridin-5-yl]methyl}-4-pyrimidinamine-d2, the deuterated analogues of Example 14 was also prepared as the hydrochloride salt:

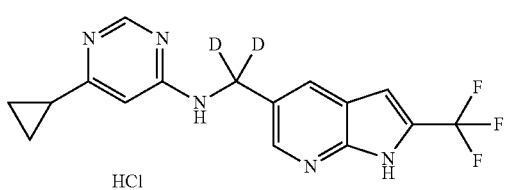 [SMILES: [2H]C([2H])(Nc1cc(C2CC2)ncn1)c1cnc2[nH]c(C(F)(F)F)cc2c1 ; Cl]

To a stirred solution of 4-chloro-6-cyclopropylpyrimidine (Intermediate 30, 110 mg) in N-methyl-2-pyrrolidone (NMP) (2.691 mL) was added {[2-(trifluoromethyl)-1H-pyrrolo[2,3-b]pyridin-5-yl]methyl}amine-d2 (Intermediate 38 155 mg), DIPEA (0.249 mL). The reaction mixture stirred at 120° C. for 4 hrs. DIPEA (1 mL) was then added and the reaction mixture stirred for a further 4 hrs. The reaction mixture was diluted with water (20 mL) and extracted with ethyl acetate (3×20 mL). The organic layers were combined, dried under magnesium sulfate and evaporated to dryness in vacuo to afford the crude residues. Crude residues were purified on SP4 column chromatography (Si, 25+M) eluting with a gradient of 0-5% DCM/2M NH$_3$ in MeOH. Product containing fractions were combined and evaporated under reduced pressure to give 42 mg compound. The compound was then dissolved in methanol (2 mL) and 1M HCl in diethyl ether (0.15 mL) was added. The solution was evaporated in vacuo to give the title compound as a brown solid (36 mg);

m/z (ES$^+$) 334 (M+1); $^1$H NMR (400 MHz, METHANOL-d$_4$) δ ppm 8.38-8.67 (3H, m), 7.07-7.21 (1H, m), 6.35-6.70 (1H, m), 1.91-2.18 (1H, m), 1.24-1.41 (2H, m), 1.02-1.16 (2H, m).

Example 15

6-(1-Fluoro-1-methylethyl)-N-{[2-(trifluoromethyl)-1H-pyrrolo[2,3-b]pyridin-5-yl]methyl}-4-pyrimidinamine

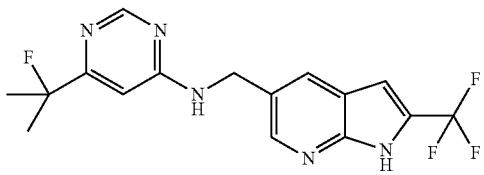 [SMILES: CC(C)(F)c1cc(NCc2cnc3[nH]c(C(F)(F)F)cc3c2)ncn1]

Prepared from 4-Chloro-6-(1-fluoro-1-methylethyl)pyrimidine (Intermediate 29) and 1-[2-(trifluoromethyl)-1H-pyrrolo[2,3-b]pyridin-5-yl]methanamine (Intermediate 5) according to the method as described in Example 14;

m/z (ES$^+$) 354 (M+1); $^1$H NMR (400 MHz, d6-DMSO): δ 12.80 (1H, brs), 8.45-8.41 (2H, m), 8.08-8.04 (2H, m), 7.04 (1H, d), 6.63 (1H, s), 4.66 (2H, d), 1.55 (6H, d).

6-(1-Fluoro-1-methylethyl)-N-{[2-(trifluoromethyl)-1H-pyrrolo[2,3-b]pyridin-5-yl]methyl}-4-pyrimidinamine-d$_2$, the deuterated analogue of Example 15 was also prepared:

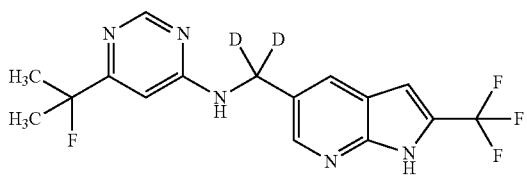 [SMILES: [2H]C([2H])(Nc1cc(C(C)(C)F)ncn1)c1cnc2[nH]c(C(F)(F)F)cc2c1]

1-[2-(Trifluoromethyl)-1H-pyrrolo[2,3-b]pyridin-5-yl]methanamine-d$_2$ (Intermediate 38, 50 mg, 0.230 mmol), chloro-6-(1-fluoro-1-methylethyl)pyrimidine (Intermediate 29, 60.3 mg, 0.345 mmol) and DIPEA (0.080 mL, 0.460 mmol) were added together in dry N-methyl-2-pyrrolidone (5 mL) and the mixture was stirred and heated at 160° C. for 60 minutes in the microwave. The reaction mixture was diluted with ethyl acetate and washed with water and brine. The organic layer was separated, dried under magnesium sulfate and evaporated under reduced pressure. The residue was purified by MDAP. Product containing fractions were combined and evaporated under reduced pressure. The resulting solid was dried under high vacuum at 45° C. for 18 hours to give the title compound as a white solid (11 mg).

m/z (ES$^+$) 356 (M+1); $^1$H NMR (400 MHz, METHANOL-d$_4$) δ ppm 8.41-8.43 (1H, m), 8.38-8.40 (1H, M), 8.11-8.13 (1H, m), 6.92-6.94 (1H, m), 6.67-6.69 (1H, m), 1.59 (6H, d).

Example 16

6-Ethyl-5-fluoro-N-{[2-(trifluoromethyl)-1H-pyrrolo[2,3-b]pyridin-5-yl]methyl}-4-pyrimidinamine Hydrochloride salt

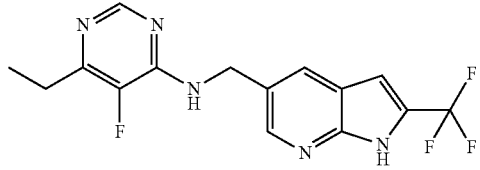 [SMILES: CCc1ncnc(NCc2cnc3[nH]c(C(F)(F)F)cc3c2)c1F]

A solution of 1-[2-(trifluoromethyl)-1H-pyrrolo[2,3-b]pyridin-5-yl]methanamine (Intermediate 5, 50 mg, 0.232 mmol) in dry NMP (2 mL) was treated with 4-chloro-6-ethyl-5-fluoropyrimidine (Intermediate 27, 74.6 mg, 0.465 mmol) and DIPEA (0.081 mL, 0.465 mmol). The reaction mixture was then stirred at room temperature over the weekend. The reaction mixture was poured into water (20 mL) and extracted with ethyl acetate (20 mL). The organic extract was then washed with water (20 mL×2), dried (MgSO$_4$), filtered and the solvent was removed. The resulting residues were then purified on the MDAP and fractions containing desired product were combined and evaporated to dryness. The resulting residues were then dissolved in methanol (10 mL) and 4M HCl in dioxane (1 mL) was added. The mixture was then evaporated to dryness to give the title compound as an off white solid (45 mg).

m/z (ES$^+$) 340 (M+1); $^1$H NMR (400 MHz, d6-DMSO): δ 12.95 (1H, brs), 9.72 (1H, brs), 8.66 (1H, s), 8.48 (1H, d), 8.11 (1H, d), 7.05 (1H, s), 4.84 (2H, d), 2.76 (2H, q), 1.22 (3H, t).

Example 17

6-Chloro-N-{[2-(trifluoromethyl)-1H-pyrrolo[2,3-b]pyridin-5-yl]methyl}-4-pyrimidinamine

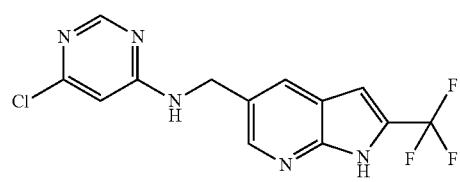

Potassium carbonate (106 mg, 0.767 mmol) was added to 1-[2-(trifluoromethyl)-1H-pyrrolo[2,3-b]pyridin-5-yl]methanamine (Intermediate 5, 75 mg, 0.349 mmol) and 4,6-dichloropyrimidine (104 mg, 0.697 mmol) in DMSO (2 mL). The mixture was heated at 120° C. for 1 hour in the microwave. Crude LCMS showed desired product and no starting material left so the reaction mixture was diluted with ethyl acetate (20 mL) and washed with water (10 mL), brine (10 mL), water (10 mL) and brine (10 mL). The organic layer was dried (sodium sulfate), filtered and concentrated under reduced pressure. This solid was dissolved in a mixture of acetonitrile and DMSO (1:1, 1.8 mL) and purified by MDAP. Fractions containing pure product were combined and concentrated under reduced pressure to give the title compound as a brown solid (24 mg);

m/z (ES⁺) 328 (M+1), 330 (M+3); ¹H NMR (400 MHz, d₄-MeOD): δ 8.41-8.40 (1H, d), 8.27 (1H, bs), 8.11-8.10 (1H, d), 6.93 (1H, d), 6.56 (1H, s), 4.73 (2H, bs).

Example 18

6-Ethyl-N-{[2-(trifluoromethyl)-1H-indol-5-yl]methyl}-4-pyrimidinamine

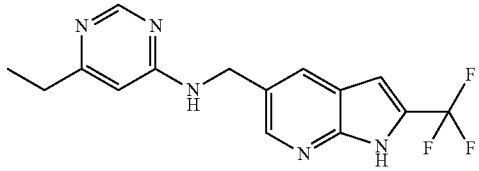

A stirred mixture of {[2-(trifluoromethyl)-1H-indol-5-yl]methyl}amine (Intermediate 34, 171 mg, 0.8 mmol), 4-chloro-6-ethylpyrimidine (Intermediate 12, 171 mg, 1.200 mmol) and DI PEA (0.279 mL, 1.600 mmol) in N-methyl-2-pyrrolidone (1 mL) was heated at 100° C. for 2 hours. After cooling to room temperature the reaction mixture was diluted with ethyl acetate. The solution was washed with water and brine, dried and evaporated. The residue was purified by silica gel chromatography eluting with 50-100% ethyl acetate in isohexane to give the crude product which was triturated with ether/isohexane and the resulting colourless solid was collected, washed with cold ether and dried to give the title compound (89 mg).

m/z (ES⁺) 321 (M+1); ¹H NMR (400 MHz, d₆-DMSO): δ 12.20 (1H, bs), 8.32 (1H, s), 7.76-7.72 (1H, m), 7.59 (1H, s), 7.44-7.42 (1H, d), 7.28-7.25 (1H, d), 6.98 (1H, s), 6.34 (1H, s), 4.58 (2H, bs), 2.48-2.42 (2H, q), 1.15-1.10 (3H, t).

Example 19

6-Ethyl-5-methyl-N-{[2-(trifluoromethyl)-1H-pyrrolo[2,3-b]pyridin-5-yl]methyl}-4-pyrimidinamine

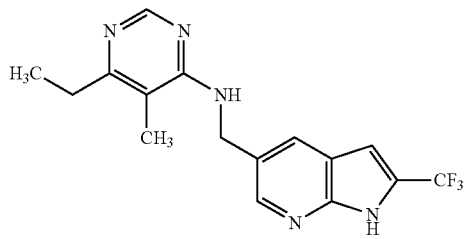 [SMILES: CCc1ncnc(NCc2cnc3[nH]c(C(F)(F)F)cc3c2)c1C]

1-[2-(Trifluoromethyl)-1H-pyrrolo[2,3-b]pyridin-5-yl]methanamine (Intermediate 5, 129 mg, 0.6 mmol), 4-chloro-6-ethyl-5-methylpyrimidine (Intermediate 41, 141 mg, 0.900 mmol) and DIPEA (0.210 mL, 1.200 mmol) were added together with N-methyl-2-pyrrolidone (1 mL) and the resulting mixture was stirred and heated to 120° C. for 6 hours. The reaction mixture was diluted with ethyl acetate and washed with sodium hydrogen carbonate solution, water and brine. The organic layer was separated, dried under magnesium sulfate and evaporated under reduced pressure. The residue was purified by MDAP. Product containing fractions were combined and evaporated under reduced pressure. The resulting solid was triturated with ether/isohexane (1:1) and the resulting solid was collected and dried affording the title compound (60 mg);

m/z (ES⁺) 335 (M+1); ¹H NMR (400 MHz, CDCl₃) δ ppm 8.73 (1H, s), 8.52 (1H, s), 7.67 (1H, s), 6.80-6.99 (1H, m), 4.79 (2H, s), 4.12 (2H, d), 2.75-2.93 (3H, m), 2.71 (2H, d), 1.10-1.27 (3H, m).

Example 20

6-(1-fluoroethyl)-5-methyl-N-{[2-(trifluoromethyl)-1H-pyrrolo[2,3-b]pyridin-5-yl]methyl}-4-pyrimidinamine hydrochloride

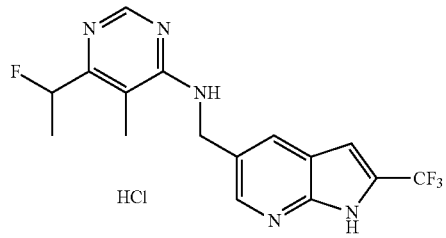 [SMILES: Cc1c(NCc2cnc3[nH]c(C(F)(F)F)cc3c2)ncnc1C(C)F ; Cl]

1-[2-(Trifluoromethyl)-1H-pyrrolo[2,3-b]pyridin-5-yl]methanamine (Intermediate 5, 100 mg, 0.465 mmol), 4-chloro-6-(1-fluoroethyl)-5-methylpyrimidine (Intermediate 45, 153 mg, 0.874 mmol) and DIPEA (0.162 mL, 0.929 mmol) were added together in N-methyl-2-pyrrolidone (NMP) (3 mL) and the resulting mixture was heated at 100° C. for 2 hours and allowed to cool to room temperature. The reaction mixture was diluted with ethyl acetate and washed with water and brine. The organic layer was separated, dried under magnesium sulfate and evaporated under reduced pressure. The residue was purified by column chromatography (Biotage SP4, 25+M) eluting with a gradient of 0-100% ethyl acetate and iso-hexane. Product containing fractions were combined and evaporated under reduced pressure. The residue (26 mg) was dissolved in methanol (2 mL), treated with 1M HCl in diethyl ether (0.1 mL, 0.100 mmol) and the resulting mixture was evaporated under reduced pressure. The resulting solid was dried under high vacuum at 40° C. for 18 hours to give the title compound as a white solid (23 mg);

m/z (ES⁺) 354 (M+1); ¹H NMR (400 MHz, DMSO-d₆) δ ppm 12.76-13.13 (1H, bs), 9.16-9.47 (1H, bs), 8.71 (1H, s), 8.49 (1H, d,), 8.11 (1H, d), 7.03 (1H, s), 6.12 (1H, m), 4.87 (2H, dd), 2.14 (3H, s), 1.50-1.72 (3H, m).

Example 21

6-(1,1-difluoroethyl)-5-methyl-N-{[2-(trifluoromethyl)-1H-pyrrolo[2,3-b]pyridin-5-yl]methyl}-4-pyrimidinamine hydrochloride

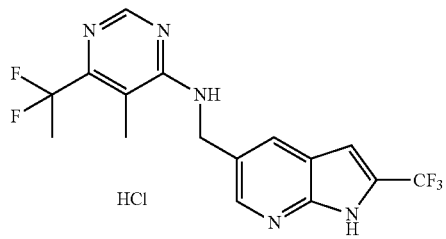 [SMILES: Cc1c(NCc2cnc3[nH]c(C(F)(F)F)cc3c2)ncnc1C(C)(F)F ; Cl]

1-[2-(Trifluoromethyl)-1H-pyrrolo[2,3-b]pyridin-5-yl] methanamine (Intermediate 5, 100 mg, 0.465 mmol), 4-chloro-6-(1,1-difluoroethyl)-5-methylpyrimidine (Intermediate 46, 134 mg, 0.697 mmol) and DIPEA (0.162 mL, 0.929 mmol) were added together in N-methyl-2-pyrrolidone (NMP) (3 mL) and the resulting mixture was stirred at room temperature for 2 hours. The reaction mixture was heated at 100° C. for 1 hour, allowed to cool to room temperature, diluted with ethyl acetate and washed with water and brine. The organic layer was separated, dried under magnesium sulfate and evaporated under reduced pressure. The residue was purified by column chromatography (Biotage SP4, 25+M, collect all) eluting with a gradient of 0-100% ethyl acetate and iso-hexane. Product containing fractions were combined and evaporated under reduced pressure. The residue was triturated with DCM and the solid collected by filtration (53 mg), dissolved in methanol (2 mL), treated with 1M HCl in diethyl ether (0.16 mL, 0.160 mmol) and the resulting mixture was evaporated under reduced pressure. The resulting solid was dried under high vacuum at 40° C. for 18 hours to give the title compound as a white solid (53 mg);

m/z (ES$^+$) 372 (M+1); $^1$H NMR (400 MHz, DMSO-d$_6$) δ ppm 12.72-13.10 (1H, m), 8.49 (3H, m), 8.10 (1H, s), 7.03 (1H, s), 4.81 (2H, d), 2.21 (3H, s), 1.98 (3H, t).

Example 22

5-methyl-6-(trifluoromethyl)-N-{[2-(trifluoromethyl)-1H-pyrrolo[2,3-b]pyridin-5-yl]methyl}-4-pyrimidinamine hydrochloride salt

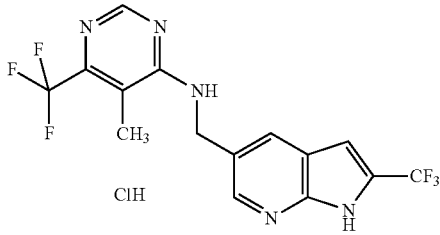 [SMILES: Cc1c(NCc2cnc3[nH]c(C(F)(F)F)cc3c2)ncnc1C(F)(F)F ; Cl]

1-[2-(Trifluoromethyl)-1H-pyrrolo[2,3-b]pyridin-5-yl] methanamine (Intermediate 5, 100 mg, 0.465 mmol), 4-chloro-5-methyl-6-(trifluoromethyl)pyrimidine (ANICHEM CAS425394-59-8, 83 mg, 0.465 mmol) and triethylamine (0.130 mL, 0.929 mmol) were added together in N,N-dimethylformamide (5 mL) and the resulting mixture was stirred at room temperature for overnight. The reaction mixture was diluted with ethyl acetate and washed with water and brine. The organic layer was separated, dried under magnesium sulfate and evaporated under reduced pressure. The resulting solid was purified by trituration in diethyl ether. The resulting solid was dissolved in 1:1 ethyl acetate:methanol and 4M HCl in 1,4-dioxane was added. The mixture was then evaporated under reduced pressure, the resulting residue was triturated again in diethyl ether the mixture was allowed to cool to room temperature and the white solid was collected to give the titled compound as a white solid (175 mgs);

m/z (ES$^+$) 374/375 (M+1); $^1$H NMR (400 MHz, DMSO-d$_6$) δ ppm 12.70-13.02 (1H, m), 8.34-8.60 (2H, m), 7.97-8.23 (2H, m), 7.02 (1H, d), 4.77 (2H, d), 2.19 (3H, d).

Example 23

6-(difluoromethyl)-5-methyl-N-{[2-(trifluoromethyl)-1H-pyrrolo[2,3-b]pyridin-5-yl]methyl}-4-pyrimidinamine

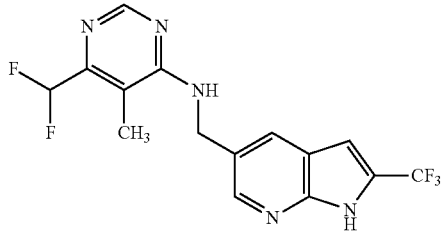 [SMILES: Cc1c(NCc2cnc3[nH]c(C(F)(F)F)cc3c2)ncnc1C(F)F]

1-[2-(Trifluoromethyl)-1H-pyrrolo[2,3-b]pyridin-5-yl] methanamine (Intermediate 5, 100 mg, 0.465 mmol), 4-chloro-6-(difluoromethyl)-5-methylpyrimidine (ANICHEM CAS425394-59-8, 83 mg, 0.465 mmol) and DIPEA (0.162 mL, 0.929 mmol) were added together in N,N-dimethylformamide (5 mL) and the resulting mixture was stirred at room temperature for overnight. The reaction mixture was diluted with ethyl acetate and washed with water and brine. The organic layer was separated, dried under magnesium sulfate and evaporated under reduced pressure. The residue was purified by MDAP. Product containing fractions were combined and evaporated under reduced pressure. The resulting solid was dried under high vacuum at 45° C. for 18 hours to give the title compound as a white solid (38 mg);

m/z (ES$^+$) 358/359 (M+1); $^1$H NMR (400 MHz, CD$_3$OD) δ ppm 8.65-8.87 (3H, m), 7.02-7.65 (2H, m), 5.12 (2H, s), 2.33 (3H, s), 2.05 (1H, s).

Example 24

6-(fluoromethyl)-5-methyl-N-{[2-(trifluoromethyl)-1H-pyrrolo[2,3-b]pyridin-5-yl]methyl}-4-pyrimidinamine hydrochloride

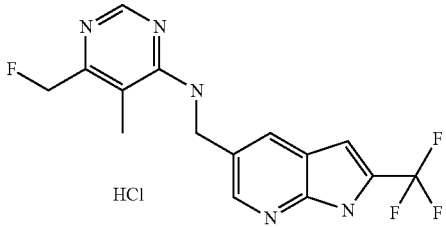 [SMILES: Cc1c(CF)ncnc1NCc1cnc2[nH]c(C(F)(F)F)cc2c1 ; Cl]

A solution of 1-[2-(trifluoromethyl)-1H-pyrrolo[2,3-b]pyridin-5-yl]methanamine (Intermediate 5, 300 mg, 1.394 mmol) in dry N,N-dimethylformamide (DMF) (15.000 mL) was treated with 4-chloro-6-(fluoromethyl)-5-methylpyrimidine (Intermediate 51, 336 mg, 2.091 mmol) and triethylamine (0.389 mL, 2.79 mmol). The reaction mixture was heated at 100° C. and stirred for 28 hours. The reaction mixture was poured into water (20 mL) and extracted with ethyl acetate (2×20 mL). The organic extract was then dried under magnesium sulphate, filtered and the solvent removed under reduced pressure. The residue was purified on SP4 column chromatography (25+M) eluting with 0-100% iso-hexane-ethyl acetate. Product containing fractions were combined and evaporated under reduced pressure. The white residue was then dissolved in 1:1 ethyl acetate:methanol (2 mL) and 1M HCl in diethylether (0.05 mL, 0.543 mmol) was added. The mixture was then evaporated to dryness to give the title compound as a white solid (15 mg);

m/z (ES+) 340 (M+1); ¹H NMR (400 MHz, METHANOL-d₄) δ ppm 8.68-8.70 (1H, m), 8.57-8.60 (1H, m), 8.44-8.47 (1H, m), 7.06-7.12 (1H, m), 5.72-5.76 (1H, m), 5.60-5.64 (1H, m), 4.97-5.11 (2H, m), 2.16 (3H, s).

Example 25

6-cyclopropyl-5-methyl-N-{[2-(trifluoromethyl)-1H-pyrrolo[2,3-b]pyridin-5-yl]methyl}-4-pyrimidinamine hydrochloride

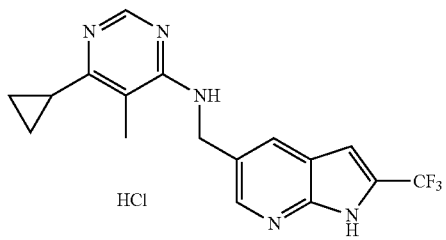 [SMILES: Cc1c(NCc2cnc3[nH]c(C(F)(F)F)cc3c2)ncnc1C1CC1 ; Cl]

1-[2-(Trifluoromethyl)-1H-pyrrolo[2,3-b]pyridin-5-yl] methanamine (Intermediate 5, 185 mg, 0.516 mmol), 4-chloro-6-cyclopropyl-5-methylpyrimidine (Intermediate 52, 122 mg, 0.722 mmol) and DIPEA (0.180 ml, 1.032 mmol) were added together in N-methyl-2-pyrrolidone (NMP) (2 ml) and the resulting mixture was heated at 120° C. for 18 hours and allowed to cool to room temperature. The reaction mixture was diluted with ethyl acetate and washed with water and brine. The organic layer was separated, dried under magnesium sulfate and evaporated under reduced pressure. The residue was purified by SP4 column chromatography eluting with a gradient of 0-100% ethyl acetate and iso-hexane. Product containing fractions were combined and evaporated under reduced pressure. The residue, contaminated with NMP, was dissolved in methanol and passed down an SCX column (1 g) eluting with methanol, followed by 2M ammonia/methanol. Product containing fractions were combined and evaporated under reduced pressure. The resulting residue was dissolved in methanol (1 mL), treated with 1M hydrochloric acid in ether (0.05 ml, 0.050 mmol), the solvent removed under reduced pressure and the residue dried under high vacuum at 40° C. for 4 hours to give the title compound as a yellow solid, (10 mg);

m/z (ES+) 348 (M+1); ¹H NMR (400 MHz, METHANOL-d₄) δ ppm 8.53-8.57 (1H, m), 8.47-8.50 (1H, m), 8.39-8.42 (1H, m), 7.05-7.08 (1H, m), 4.98-5.01 (2H, m), 2.31 (3H, s), 2.24-2.28 (1H, m), 1.23-1.30 (2H, m), 1.01 (2H, m).

Hydrochoride salts of the compounds of Examples 5, 8, 9, 10, 11 and 14 were prepared in addition to the free base. Hydrochoride salts can, for example, be prepared by dissolving the free base in methanol followed by treatment with 4M HCl in dioxane as described in the preparation of the salt of Example 16.

Biological Assay

The PAM activity of the compounds of the invention at the α7 nAChR may be determined using the following cell-based calcium flux assay which uses a Fluorimetric Image Plate Reader (FLIPR) (see Schroeder et al.; J. Biomolecular Screening, 1(2), p 75-80, 1996). GH4C1 cell line stably transfected with human α7 nAChR was suspended in a 384 well plate and incubated at 30° C. for 48 h in a 5% carbon dioxide atmosphere. The growth media was removed and the cells washed three times with a solution of Hanks' balanced salt solution (HBSS), 20 mM HEPES and 2.5 mM probenecid leaving 20 µl washing solution in each well. A loading solution (20 µl) containing HBSS, probenecid, 1-4 µM Fluo4 AM (a calcium indicator dye) and pluronic acid was added and the plate incubated for 45 min at 37° C. under an atmosphere free from carbon dioxide. The cells were washed three times leaving 30 µl in each well. The plate containing the cells and calcium indicator dye were then transferred to the FLIPR. The assay was initiated by collecting baseline datapoints at 10 second intervals followed by addition of the test compound in buffer solution (0.33% DMSO) and diluted to a final concentration of 10 µM and serial dilution of the wells, 1:2 or 1:3, gave a low concentration of <1 nM. Following a further 5-10 mins 10 µl of 50 µM nicotine was added and data collected for 2-3 mins. Nicotine produced a rapid, transient and reproducible calcium flux which could be potentiated with the positive allosteric modulator test compounds.

Supporting compounds 1 to 25, and/or hydrochloride salts thereof, were screened using the assay described above and gave a $pEC_{50}$ of equal to or greater than 5.0 with a maximum potentiation of the response area to approximately 1200% relative to nicotine control. The compound of Example 8 and the HCl salt thereof gave a $pEC_{50}$ of 6 and the deuterated analogue of Example 8 gave a $pEC_{50}$ of 5.9. The compound of Example 15 gave a $pEC_{50}$ of 6.4 and the deuterated analogue of Example 15 gave a $pEC_{50}$ of 6.2. The assay results of the supporting compounds are presented in Table 1 below:

TABLE 1

| Example | Structure | Name | $pEC_{50}$ Mean |
|---|---|---|---|
| 1 | 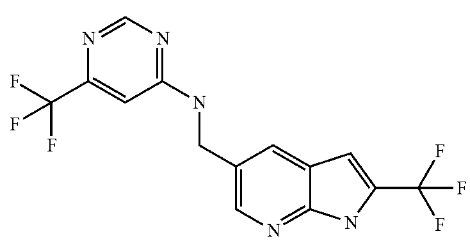 [SMILES: FC(F)(F)c1cc(NCc2cnc3[nH]c(C(F)(F)F)cc3c2)ncn1] | 6-(Trifluoromethyl)-N-{[2-(trifluoromethyl}-1H-pyrrolo[2,3-b]pyridin-5-yl]methyl}-4-pyrimidinamine | *** |

TABLE 1-continued

| Example | Structure | Name | pEC$_{50}$ Mean |
|---|---|---|---|
| 2 | 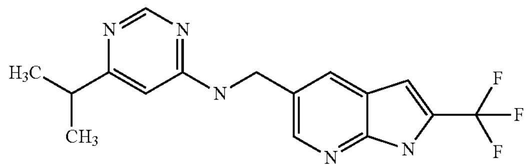 [SMILES: CC(C)c1cc(NCc2cnc3[nH]c(C(F)(F)F)cc3c2)ncn1] | 6-(1-Methylethyl)-N-{[2-(trifluoromethyl)-1H-pyrrolo[2,3-b]pyridin-5-yl]methyl}-4-pyrimidinamine | * |
| 3 | 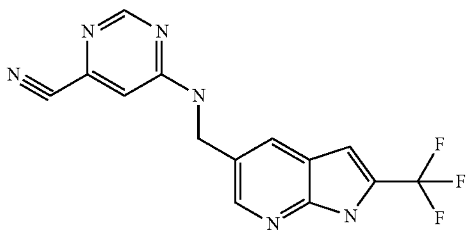 [SMILES: N#Cc1cc(NCc2cnc3[nH]c(C(F)(F)F)cc3c2)ncn1] | 6-({[2-(Trifluoromethyl)-1H-pyrrolo[2,3-b]pyridin-5-yl]methyl}amino)-4-pyrimidinecarbonitrile | ** |
| 4 | 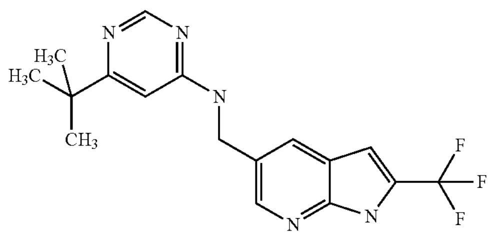 [SMILES: CC(C)(C)c1cc(NCc2cnc3[nH]c(C(F)(F)F)cc3c2)ncn1] | 6-(1,1-Dimethylethyl)-N-{[2-(trifluoromethyl)-1H-pyrrolo[2,3-b]pyridin-5-yl]methyl}-4-pyrimidinamine | ** |
| 5 | 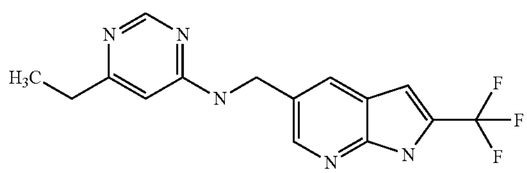 [SMILES: CCc1cc(NCc2cnc3[nH]c(C(F)(F)F)cc3c2)ncn1] | 6-Ethyl-N-{[2-(trifluoromethyl)-1H-pyrrolo[2,3-b]pyridin-5-yl]methyl}-4-pyrimidinamine | * |
| 5 HCl | 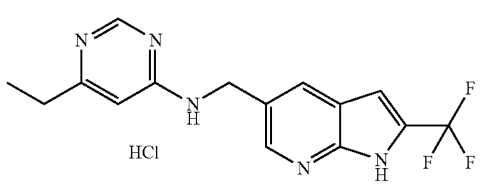 [SMILES: CCc1cc(NCc2cnc3[nH]c(C(F)(F)F)cc3c2)ncn1 ; Cl] | 6-Ethyl-N-{[2-(trifluoromethyl)-1H-pyrrolo[2,3-b]pyridin-5-yl]methyl}-4-pyrimidinamine HCl | * |
| 6 | 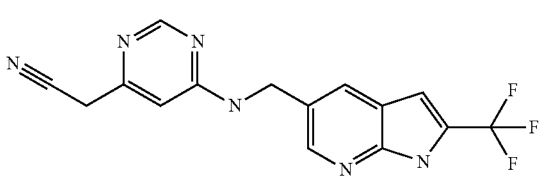 [SMILES: N#CCc1cc(NCc2cnc3[nH]c(C(F)(F)F)cc3c2)ncn1] | [6-({[2-(Trifluoromethyl)-1H-pyrrolo[2,3-b]pyridin-5-yl]methyl}amino)-4-pyrimidinyl]acetonitrile | * |
| 7 | 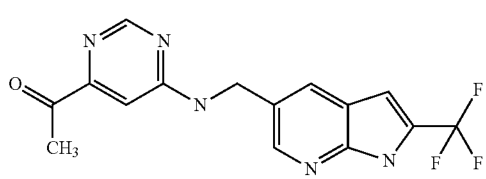 [SMILES: CC(=O)c1cc(NCc2cnc3[nH]c(C(F)(F)F)cc3c2)ncn1] | 1-[6-({[2-(Trifluoromethyl)-1H-pyrrolo[2,3-b]pyridin-5-yl]methyl}amino)-4-pyrimidinyl]ethanone | * |

TABLE 1-continued

| Example | Structure | Name | pEC$_{50}$ Mean |
|---|---|---|---|
| 8 | 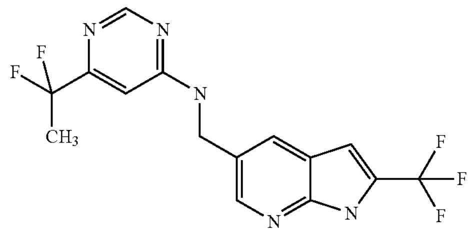 [SMILES: CC(F)(F)c1cc(NCc2cnc3[nH]c(C(F)(F)F)cc3c2)ncn1] | 6-(1,1-Difluoroethyl)-N-{[2-(trifluoromethyl)-1H-pyrrolo[2,3-b]pyridin-5-yl]methyl}-4-pyrimidinamine | *** |
| 8 HCl | 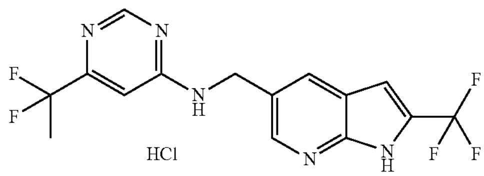 [SMILES: CC(F)(F)c1cc(NCc2cnc3[nH]c(C(F)(F)F)cc3c2)ncn1 ; Cl] | 6-(1,1-Difluoroethyl)-N-{[2-(trifluoromethyl)-1H-pyrrolo[2,3-b]pyridin-5-yl]methyl}-4-pyrimidinamine hydrochloride | *** |
| 8-d | 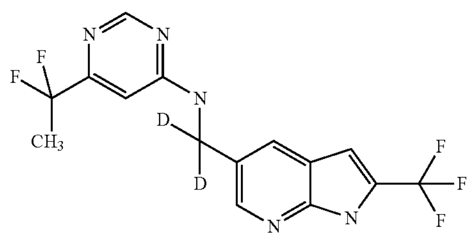 [SMILES: [2H]C([2H])(Nc1cc(C(C)(F)F)ncn1)c1cnc2[nH]c(C(F)(F)F)cc2c1] | 6-(1-Fluoroethyl)-N-{[2-(trifluoromethyl)-1H-pyrrolo[2,3-b]pyridin-5-yl]methyl}-4-pyrimidinamine-d$_2$ | ** |
| 9 | 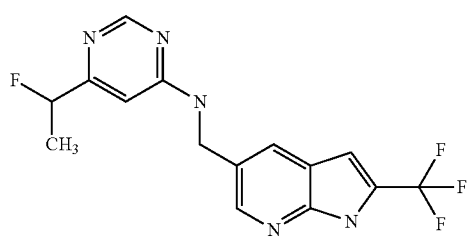 [SMILES: CC(F)c1cc(NCc2cnc3[nH]c(C(F)(F)F)cc3c2)ncn1] | 6-(1-Fluoroethyl)-N-{[2-(trifluoromethyl)-1H-pyrrolo[2,3-b]pyridin-5-yl]methyl}-4-pyrimidinamine | * |
| 9 HCl | 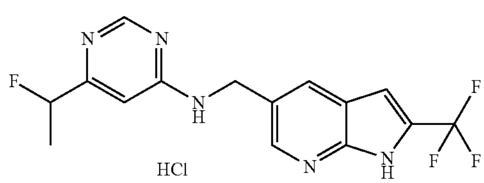 [SMILES: CC(F)c1cc(NCc2cnc3[nH]c(C(F)(F)F)cc3c2)ncn1 ; Cl] | 6-(1-Fluoroethyl)-N-{[2-(trifluoromethyl)-1H-pyrrolo[2,3-b]pyridin-5-yl]rnethyl}-4-pyrimidinamine hydrochloride | ** |
| 10 | 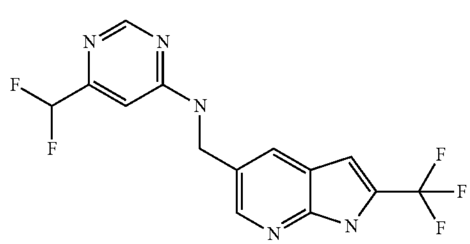 [SMILES: FC(F)c1cc(NCc2cnc3[nH]c(C(F)(F)F)cc3c2)ncn1] | 6-(Difluoromethyl)-N-{[2-(trifluoromethyl)-1H-pyrrolo[2,3-b]pyridin-5-yl]methyl}-4-pyrimidinamine | ** |
| 10 HCl | 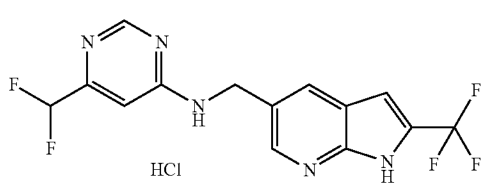 [SMILES: FC(F)c1cc(NCc2cnc3[nH]c(C(F)(F)F)cc3c2)ncn1 ; Cl] | 6-(Difluoromethyl)-N-{[2-(trifluoromethyl)-1H-pyrrolo[2,3-b]pyridin-5-yl]methyl}-4-pyrimidinamine hydrochloride | ** |

TABLE 1-continued

| Example | Structure | Name | pEC$_{50}$ Mean |
|---|---|---|---|
| 11 | 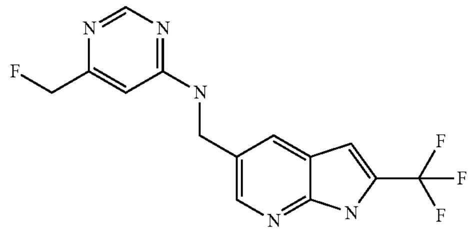 [SMILES: FCc1cc(NCc2cnc3[nH]c(C(F)(F)F)cc3c2)ncn1] | 6-(Fluoromethyl)-N-{[2-(trifluoromethyl)-1H-pyrrolo[2,3-b]pyridin-5-yl]methyl}-4-pyrimidinamine | ** |
| 11 HCl | 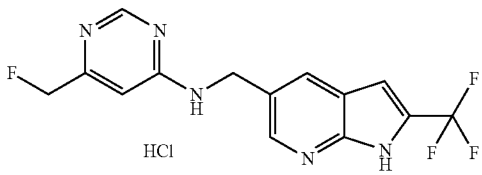 [SMILES: FCc1cc(NCc2cnc3[nH]c(C(F)(F)F)cc3c2)ncn1 ; Cl] | 6-(Fluoromethyl)-N-{[2-(trifluoromethyl)-1H-pyrrolo[2,3-b]pyridin-5-yl]methyl}-4-pyrimidinamine hydrochloride | * |
| 12 | 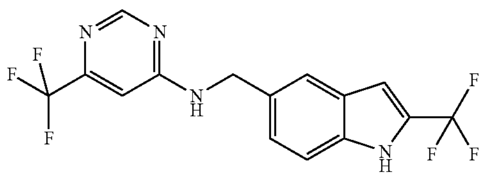 [SMILES: FC(F)(F)c1cc(NCc2ccc3[nH]c(C(F)(F)F)cc3c2)ncn1] | 6-(Trifluoromethyl)-N-{[2-(trifluoromethyl)-1H-indol-5-yl]methyl}-4-pyrimidinamine | ** |
| 13 | 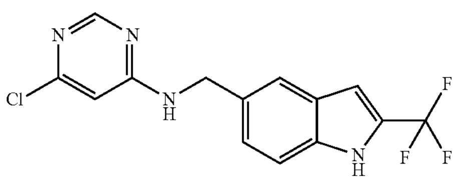 [SMILES: FC(F)(F)c1cc2cc(CNc3cc(Cl)ncn3)ccc2[nH]1] | 6-Chloro-N-{[2-(trifluoromethyl)-1H-indol-5-yl]methyl}-4-pyrimidinamine | * |
| 14 | 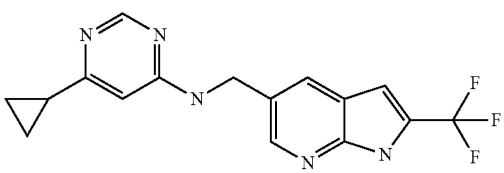 [SMILES: FC(F)(F)c1cc2cc(CNc3cc(C4CC4)ncn3)cnc2[nH]1] | 6-Cyclopropyl-N-{[2-(trifluoromethyl)-1H-pyrrolo[2,3-b]pyridin-5-yl]methyl}-4-pyrimidinamine | * |
| 14 HCl | 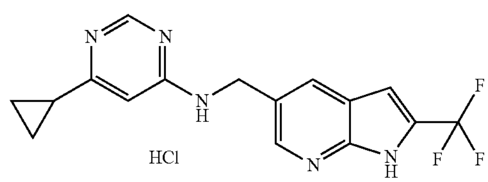 [SMILES: FC(F)(F)c1cc2cc(CNc3cc(C4CC4)ncn3)cnc2[nH]1 ; Cl] | 6-Cyclopropyl-N-{[2-(trifluorornethyl)-1H-pyrrolo[2,3-b]pyridin-5-yl]methyl}-4-pyrimidinamine hydrochloride | * |
| 14-d HCl | 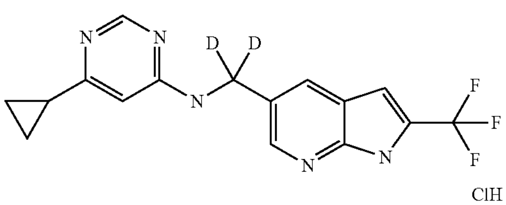 [SMILES: [2H]C([2H])(Nc1cc(C2CC2)ncn1)c1cnc2[nH]c(C(F)(F)F)cc2c1 ; Cl] | 6-Cyclopropyl-N-{[2-(trifluorornethyl)-1H-pyrrolo[2,3-b]pyridin-5-yl]methyl}-4-pyrimidinamine-d$_2$ hydrochloride | ** |
| 15 | 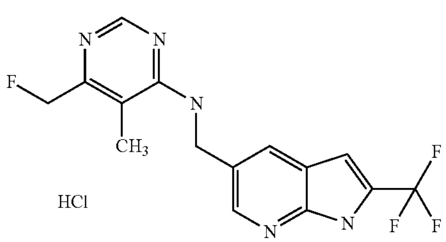 [SMILES: Cc1c(CF)ncnc1NCc1cnc2[nH]c(C(F)(F)F)cc2c1 ; Cl] | 6-(1-Fluoro-1-methylethyl)-N-{[2-(trifluoromethyl)-1H-pyrrolo[2,3-b]pyridin-5-yl]methyl}-4-pyrimidinamine | *** |

TABLE 1-continued

| Example | Structure | Name | pEC$_{50}$ Mean |
|---|---|---|---|
| 15-d | 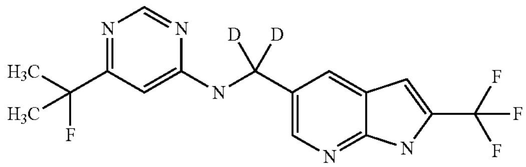 [SMILES: [2H]C([2H])(Nc1cc(C(C)(C)F)ncn1)c1cnc2[nH]c(C(F)(F)F)cc2c1] | 6-(1-Fluoro-1-methylethyl)-N-{[2-(trifluoromethyl)-1H-pyrrolo[2,3-b]pyridin-5-yl]methyl}-4-pyrimidinamine-d$_2$ | *** |
| 16 HCl | 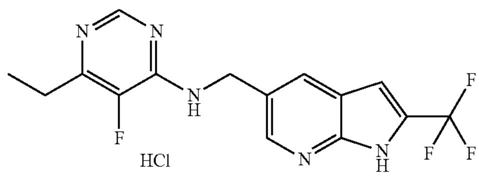 [SMILES: CCc1ncnc(NCc2cnc3[nH]c(C(F)(F)F)cc3c2)c1F ; Cl] | 6-Ethyl-5-fluoro-N-{[2-(trifluoromethyl)-1H-pyrrolo[2,3-b]pyridin-5-yl]methyl}-4-pyrimidinamine hydrochloride | *** |
| 17 | 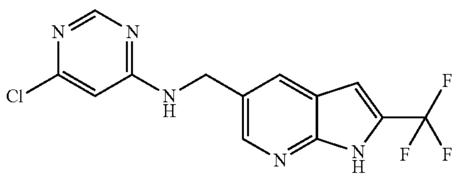 [SMILES: FC(F)(F)c1cc2cc(CNc3cc(Cl)ncn3)cnc2[nH]1] | 6-Chloro-N-{[2-(trifluoromethyl)-1H-pyrrolo[2,3-b]pyridin-5-yl]methyl}-4-pyrimidinamine | ** |
| 18 | 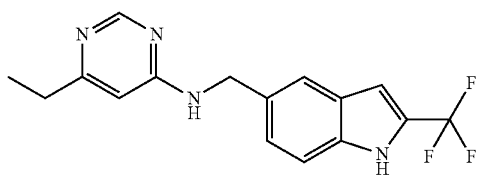 [SMILES: CCc1cc(NCc2ccc3[nH]c(C(F)(F)F)cc3c2)ncn1] | 6-Ethyl-N-{[2-(trifluoromethyl)-1H-indol-5-yl]methyl}-4-pyrimidinamine | * |
| 19 | 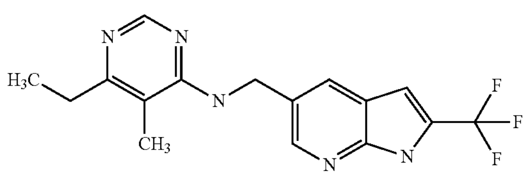 [SMILES: CCc1ncnc(NCc2cnc3[nH]c(C(F)(F)F)cc3c2)c1C] | 6-Ethyl-5-methyl-N-{[2-(trifluoromethyl)-1H-pyrrolo[2,3-b]pyridin-5-yl]methyl}-4-pyrimidinamine | * |
| 20 HCl | 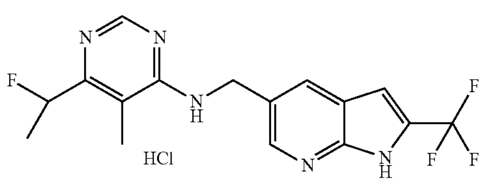 [SMILES: Cc1c(NCc2cnc3[nH]c(C(F)(F)F)cc3c2)ncnc1C(C)F ; Cl] | 6-(1-Fluoroethyl)-5-methyl-N-{[2-(trifluoromethyl)-1H-pyrrolo[2,3-6]pyridin-5-yl]methyl}-4-pyrimidinamine hydrochloride | *** |
| 21 HCl | 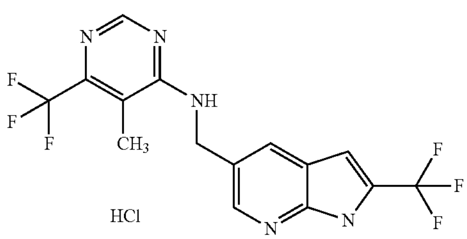 [SMILES: Cc1c(NCc2cnc3[nH]c(C(F)(F)F)cc3c2)ncnc1C(F)(F)F ; Cl] | 6-(1,1-Difluoroethyl)-5-methyl-N-{[2-(trifluoromethyl)-1H-pyrrolo[2,3-6]pyridin-5-yl]methyl}-4-pyrimidinamine hydrochloride | *** |
| 22 HCl | 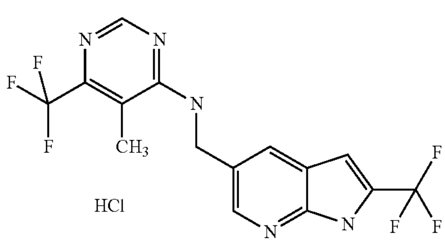 [SMILES: Cc1c(NCc2cnc3[nH]c(C(F)(F)F)cc3c2)ncnc1C(F)(F)F ; Cl] | 5-Methyl-6-(trifluoromethyl)-N-{[2-(trifluoromethyl)-1H-pyrrolo[2,3-b]pyridin-5-yl]methyl}-4-pyrimidinamine hydrochloride | *** |

TABLE 1-continued

| Example | Structure | Name | pEC₅₀ Mean |
|---|---|---|---|
| 23 | 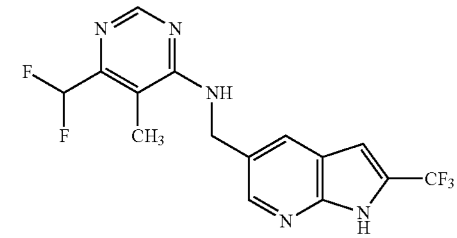 [SMILES: Cc1c(NCc2cnc3[nH]c(C(F)(F)F)cc3c2)ncnc1C(F)F] | 6-(Difluoromethyl)-5-methyl-N-{[2-(trifluoromethyl)-1H-pyrrolo[2,3-b]pyridin-5-yl]methyl}-4-pyrimidinamine | ** |
| 24 HCl | 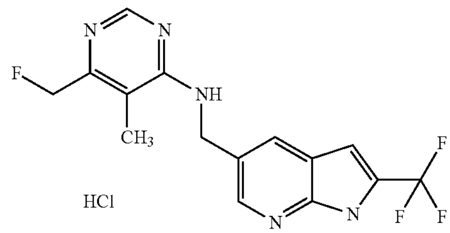 [SMILES: Cc1c(CF)ncnc1NCc1cnc2[nH]c(C(F)(F)F)cc2c1 ; Cl] | 6-(Fluoromethyl)-5-methyl-N-{[2-(trifluoromethyl)-1H-pyrrolo[2,3-6]pyridin-5-yl]methyl}-4-pyrimidinamine hydrochloride | * |
| 25 HCl | 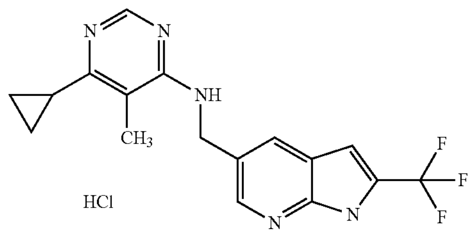 [SMILES: Cc1c(NCc2cnc3[nH]c(C(F)(F)F)cc3c2)ncnc1C1CC1 ; Cl] | 6-Cyclopropyl-5-methyl-N-{[2-(trifluoromethyl)-1H-pyrrolo[2,3-b)pyridin-5-yl]methyl}-4-pyrimidinamine hydrochloride | ** |

Key to table 1:
* = pEC50 mean of at least 5.0
** = pEC50 mean of at least 5.5
*** = pEC50 mean of at least 6.0

In vivo assays with utility for the evaluation of activity of nicotinic α7 receptor positive modulators include, but are not limited to: cognition assays in both naïve and pharmacologically-impaired animals including delayed matching and non-matching to position, passive avoidance, novel object recognition, Morris water maze (or variants thereof), radial arm maze, five choice serial reaction time task, and cued/contextual fear conditioning; sensory gating assays in both naïve and pharmacologically-impaired animals including pre-pulse inhibition of the startle reflex and auditory gating; and assays of drug-(e.g. amphetamine, morphine, phencyclidine) induced locomotor activity.

The invention claimed is:
1. A compound of formula (I):

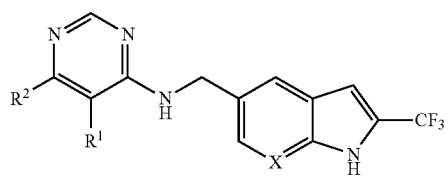

wherein:
R¹ is independently selected from the group consisting of H, C₁₋₆alkyl, haloC₁₋₆alkyl and halo;
R² is independently selected from the group consisting of C₁₋₆alkyl, haloC₁₋₆alkyl, halo, acetyl, cyano, CH₂CN and cyclopropyl; and
X is CH or N;
or a pharmaceutically acceptable salt thereof.

2. The compound according to claim 1 or a pharmaceutically acceptable salt thereof, wherein R¹ is H, fluoro or methyl.
3. The compound according to claim 1 or a pharmaceutically acceptable salt thereof, wherein R² is haloC₁₋₆alkyl.
4. The compound according to claim 1 or a pharmaceutically acceptable salt thereof, wherein R² is selected from C₂₋₃alkyl, fluoroC₁₋₃alkyl, chloro, acetyl, cyano, CH₂CN and cyclopropyl.
5. The compound according to claim 1 or a pharmaceutically acceptable salt thereof, wherein X is N.
6. A compound which is:
6-(trifluoromethyl)-N-{[2-(trifluoromethyl)-1H-pyrrolo[2,3-b]pyridin-5-yl]methyl}-4-pyrimidinamine;
6-(1-methylethyl)-N-{[2-(trifluoromethyl)-1H-pyrrolo[2,3-b]pyridin-5-yl]methyl-4-pyrimidinamine;
6-({[2-(trifluoromethyl)-1H-pyrrolo[2,3-b]pyridin-5-yl]methyl}amino)-4-pyrimidinecarbonitrile;
6-(1,1-dimethylethyl)-N-{[2-(trifluoromethyl)-1H-pyrrolo[2,3-b]pyridin-5-yl]methyl}-4-pyrimidinamine;
6-ethyl-N-([2-(trifluoromethyl)-1H-pyrrolo[2,3-b]pyridin-5-yl]methyl}-4-pyrimidinamine;
[6-({[2-(trifluoromethyl)-1H-pyrrolo[2,3-b]pyridin-5-yl]methyl}amino)-4-pyrimidinyl]acetonitrile;
1-[6-({[2-(trifluoromethyl)-1H-pyrrolo[2,3-b]pyridin-5-yl]methyl}) amino)-4-pyrimidinyl]ethanone;
6-(1,1-difluoroethyl)-N-{[2-(trifluoromethyl)-1H-pyrrolo[2,3-b]pyridin-5-yl]methyl}-4-pyrimidinamine;
6-(1-fluoroethyl)-N-{[2-(trifluoromethyl)-1H-pyrrolo[2,3-b]pyridin-5-yl]methyl}-4-pyrimidinamine;

6-(difluoromethyl)-N-{[2-(trifluoromethyl)-1H-pyrrolo[2,3-b]pyridin-5-yl]methyl}-4-pyrimidinamine;

6-(fluoromethyl)-{[2-(trifluoromethyl)-1H-pyrrolo[2,3-b]pyridin-5-yl]methyl}-4-pyrimidinamine;

6-(trifluoromethyl)-N-{[2-(trifluoromethyl)-1H-indol-5-yl]methyl}-4-pyrimidinanmine;

6-chloro-N-{[2-(trifluoromethyl)-1H-indol-5-yl]methyl}-4-pyrimidinamine;

6-cyclopropyl-N-{[2-(trifluoromethyl)-1H-pyrrolo[2,3-b]pyridin-5-yl]methyl)}4-pyrimidinamine;

6-(1-fluoro-1-methylethyl)-N-{[2-(trifluoromethyl)-1H-pyrrolo[2,3-b]pyridin-5-yl]methyl}-4-pyrimidinamine;

6-ethyl-5-fluoro-N-{[2-(trifluoromethyl)-1H-pyrrolo[2,3-b]pyridin-5-yl]methyl}-4-pyrimidinamine;

6-chloro-N-{[2-(trifluoromethyl)-1H-pyrrolo[2,3-b]pyridin-5-yl]methyl}-4-pyrimidinamine; or 6-ethyl-N-{[2-(trifluoromethyl)-1H-indol-5-yl]methyl}-4-pyrimidinamine;

6-ethyl-5-methyl-N-{[2-(trifluoromethyl)-1H-pyrrolo[2,3-b]pyridin-5-yl]methyl}-4-pyrimidinamine;

6-(1-fluoroethyl)-5-methyl-N-{[2-(trifluoromethyl)-1H-pyrrolo[2,3-b]pyridin-5-yl]methyl}-4-pyrimidinamine;

6-(1,1-difluoroethyl)-5-methyl-N-{[2-(trifluoromethyl)-1H-pyrrolo[2,3-b]pyridin-5-yl]methyl)}-4-pyrimidinamine;

5-methyl-6-(trifluoromethyl)-N-{[2-(trifluoromethyl)-1H-pyrrolo[2,3-b]pyridin-5-yl]methyl}-4-pyrimidinamine;

6-(difluoromethyl)-5-methyl-N-{[2-(trifluoromethyl)-1H-pyrrolo[2,3-b]pyridin-5-yl]methyl}-4-pyrimidinamine;

6-(fluoromethyl)-5-methyl-N-{[2-(trifluoromethyl)-1H-pyrrolo[2,3-b]pyridin-5-yl]methyl}-4-pyrimidinamine; or 6-cyclopropyl-5-methyl-N-{[2-(trifluoromethyl)-1H-pyrrolo[2,3-b]pyridin-5-yl]methyl}-4-pyrimidinamine;

or a pharmaceutically acceptable salt thereof.

7. A compound according to claim 6 which is:

6-(1-fluoroethyl)-N-{[2-(trifluoromethyl)-1H-pyrrolo[2,3-b]pyridin-5-yl]methyl}-4-pyrimidinamine; or 6-(1-fluoro-1-methylethyl)-N-{[2-(trifluoromethyl)-1H-pyrrolo[2,3-b]pyridin-5-yl]methyl}-4-pyrimidinamine;

or a pharmaceutically acceptable salt thereof.

8. The compound according to claim 1 or a pharmaceutically acceptable salt thereof, wherein the compound is of the formula (Ib):

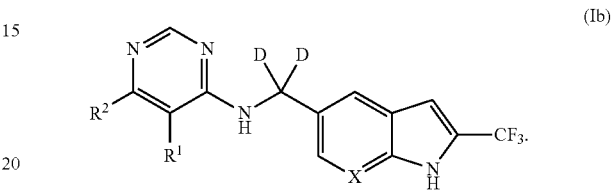

(Ib)

9. A method of treating schizophrenia in a human comprising administering an effective amount of a compound of claim 1 or a pharmaceutically acceptable salt thereof.

10. A pharmaceutical composition comprising:

a) a compound as defined in claim 1 or a pharmaceutically acceptable salt thereof; and b) one or more pharmaceutically acceptable carriers or excipients.

11. The pharmaceutical composition of claim 10 further comprising:

c) an additional therapeutic agent.

* * * * *